United States Patent [19]
Nie et al.

[11] Patent Number: 6,060,242
[45] Date of Patent: May 9, 2000

[54] PNA DIAGNOSTIC METHODS

[75] Inventors: Eileen Xiao-Feng Nie; Yuan Min Wu, both of Thornhill, Canada

[73] Assignee: Lorne Park Research, Inc., Toronto, Canada

[21] Appl. No.: 08/870,370

[22] Filed: Jun. 6, 1997

Related U.S. Application Data

[63] Continuation-in-part of application No. 08/807,901, Feb. 27, 1997, abandoned.

[51] Int. Cl.$^7$ ...................................................... C12Q 1/68
[52] U.S. Cl. ................................................ 435/6; 436/501
[58] Field of Search ........................ 435/6, 810; 436/501; 530/300, 350; 536/23.1, 24.1, 24.3–24.33; 935/77, 78

[56] References Cited

U.S. PATENT DOCUMENTS

| | | | |
|---|---|---|---|
| 4,220,450 | 9/1980 | Maggio | 23/230 B |
| 4,963,477 | 10/1990 | Tchen | 435/6 |
| 5,217,866 | 6/1993 | Summerton et al. | 435/6 |
| 5,332,659 | 7/1994 | Kidwell | 435/6 |
| 5,503,980 | 4/1996 | Cantor | 435/6 |
| 5,538,848 | 7/1996 | Livak et al. | 435/5 |
| 5,539,082 | 7/1996 | Nielsen et al. | 530/300 |
| 5,594,138 | 1/1997 | Dykstra et al. | 540/596 |
| 5,674,698 | 10/1997 | Zarling et al. | 435/7.92 |

FOREIGN PATENT DOCUMENTS

| | | |
|---|---|---|
| 0 232 967 | 8/1987 | European Pat. Off. . |
| 512334 | 11/1992 | European Pat. Off. . |
| 599337 | 6/1994 | European Pat. Off. . |
| 92 18650 | 10/1992 | WIPO . |
| 93 24652 | 12/1993 | WIPO . |
| 94/12665 | 6/1994 | WIPO . |
| 94 25477 | 11/1994 | WIPO . |
| 96/34983 | 11/1996 | WIPO . |
| 97 12995 | 4/1997 | WIPO . |

OTHER PUBLICATIONS

Perry–O'Keefe et al., "Peptide Nucleic Acid Pre–Gel Hybridization: An Alternative to Southern Hybridization," 93 Proc. Natl. Acad. Sci. USA 14670 (Dec. 1996).

Smulevitch et al., "Enhancement of Strand Inversion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996)).

Lansdorp, "Close Encounters of the PNA Kind," 14 Nature Biotechnology 1653 (Dec. 1996).

Egholm et al., "PNA Hybridizes to Complementary Oligonucleotides Obeying the Watson–Crick Hydrogen–Bonding Rules," 365 Nature 566 (1993).

Tomac et al., "Ionic Effects on the Stability and Conformation of Peptide Nucleic Acid Complexes," 118 J.Am.Chem.Soc. 5544 (1996).

Coghlan, "One–step DNA test in a tube," New Scientist, p. 21 (Nov. 5, 1994).

Heppel–Parton, "Gene Mapping by Fluorescence in Situ Hybridization," pp. 350–354, in *Molecular Biology and Biotechnology: A Comprehensive Desk Reference* (Myers, ed. 1995).

Rawls, "Optimistic About Antisense," 75(22) Chem. Eng. News 35, 39 (Jun. 2, 1997).

Matthews et al., "Analytical Strategies for the Use of DNA Probes," 169 Analytical Biochemistry 1 (1988).

Jensen et al., "Kinetics for Hybridization of Peptide Nucleic Acids (PNA) with DNA and RNA Studied with the BIAcore Technique," 36(16) Biochem. 5072 (Apr. 1997).

(List continued on next page.)

*Primary Examiner*—Ardin H. Marschel
*Attorney, Agent, or Firm*—Caesar, Rivise, Bernstein, Cohen & Pokotilow, Ltd.

[57] ABSTRACT

The invention provides a method for rapidly, economically and efficiently sequencing and assaying nucleotides in a liquid medium using a plurality of PNA probes. The method is particularly advantageous in not requiring the use of a solid support to bind the probe or the target sequence.

67 Claims, 48 Drawing Sheets

DIAGRAM OF FLUORESCENCE DETECTION SYSTEM

OTHER PUBLICATIONS

Cooper et al., "Analysis of fluorescent energy transfer in duplex and branched DNA molecules," 29 Biochemistry 9261 (1990).

Cardullo et al., "Detection of nucleic acid hybridization by nonradiative fluorescence resonance energy transfer," 85(23) PNAS USA 8790 (1988).

Uhlmann et al., Chemical Reviews, vol. 90, No. 4, pp. 543–584, 1990.

Carlsson et al., Nature, vol. 380, p. 207, 1996.

"PNA Oligomers As Hybridization Probes", Per Septive Biosystems, vol. 1, Issue 2, 1995.

Matthews et al., Analytical Chem, vol. 169, pp. 1–25.

DIAGRAM OF FLUORESCENCE DETECTION SYSTEM

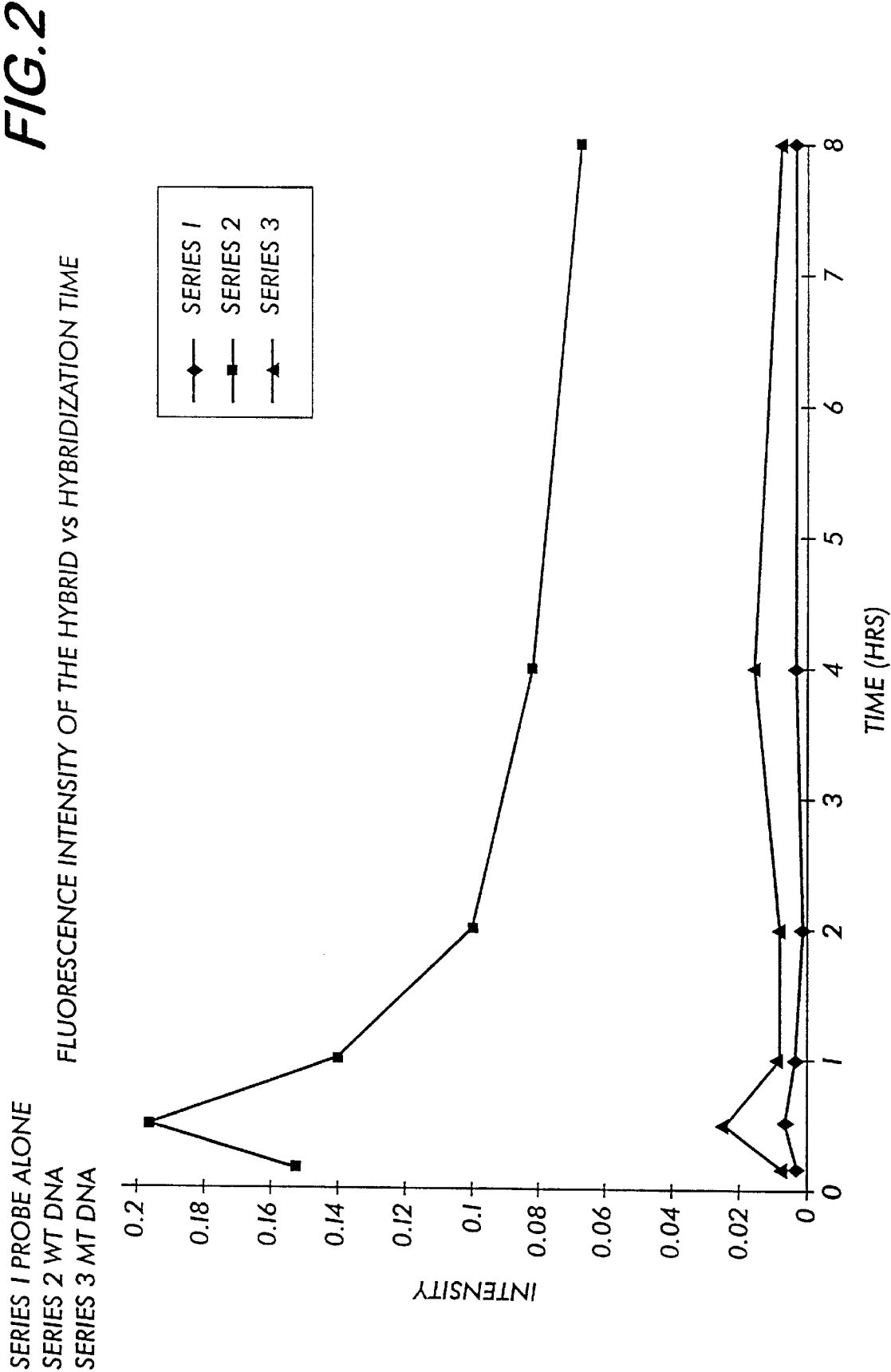

FLUORESCENCE SPECTRUM OF PROBE ALONE

FLUORESCENCE SPECTRUM OF WT DNA HYBRIDIZATION
AT 30C FOR 1 HOUR

FLUORESCENCE SPECTRUM OF MUTATED DNA (Q) HYBRIDIZATION
AT 30C FOR 1 HOUR

PROBE ALONE

FLUORESCENCE SPECTRUM OF WT DNA HYBRIDIZATION
AT 25C FOR 30 MINUTES

FLUORESCENCE SPECTRUM OF MUTATED DNA (R) HYBRIDIZATION
AT 25C FOR 30 MINUTES

FLUORESCENCE SPECTRUM OF WT DNA HYBRIDIZATION
AT 45C FOR 20 MINUTES

FLUORESCENCE SPECTRUM OF MUTATED DNA (AAG) HYBRIDIZATION AT 45C FOR 20 MINUTES

FLUORESCENCE SPECTRUM OF WT DNA HYBRIDIZATION
AT 50C FOR 2 HOURS

FLUORESCENCE SPECTRUM OF MUTATED DNA (GCG) HYBRIDIZATION
AT 50C FOR 2 HOURS

FLUORESCENCE SPECTRUM OF WT DNA HYBRIDIZATION AT 25C FOR 1 HOUR

FLUORESCENCE SPECTRUM OF MUTATED DNA (TAC) HYBRIDIZATION AT 25C FOR 1 HOUR

FLUORESCENCE SPECTRUM OF WT DNA (Seq ID No.1) RECORDED AT 525nm
WHEN ELECTRIC POWER SWITCHED ON OR OFF

FLUORESCENCE SPECTRUM OF MUTATED DNA (Seq ID No.2) RECORDED AT 525nm WHEN ELECTRIC POWER SWITCHED ON OR OFF

FLUORESCENCE SPECTRUM OF MUTATED DNA (Seq ID No.3) RECORDED AT 525nm WHEN ELECTRIC POWER SWITCHED ON OR OFF

FLUORESCENCE SPECTRUM OF WILD TYPE DNA (Seq ID No.7)
HYBRIDIZATION AT 25C FOR 1 HOUR

FLUORESCENCE SPECTRUM OF MUTATED DNA (Seq ID No.8)
HYBRIDIZATION AT 25C FOR 1 HOUR

FLUORESCENCE SPECTRUM OF MUTATED DNA (Seq ID No.9)
HYBRIDIZATION AT 25C FOR 1 HOUR

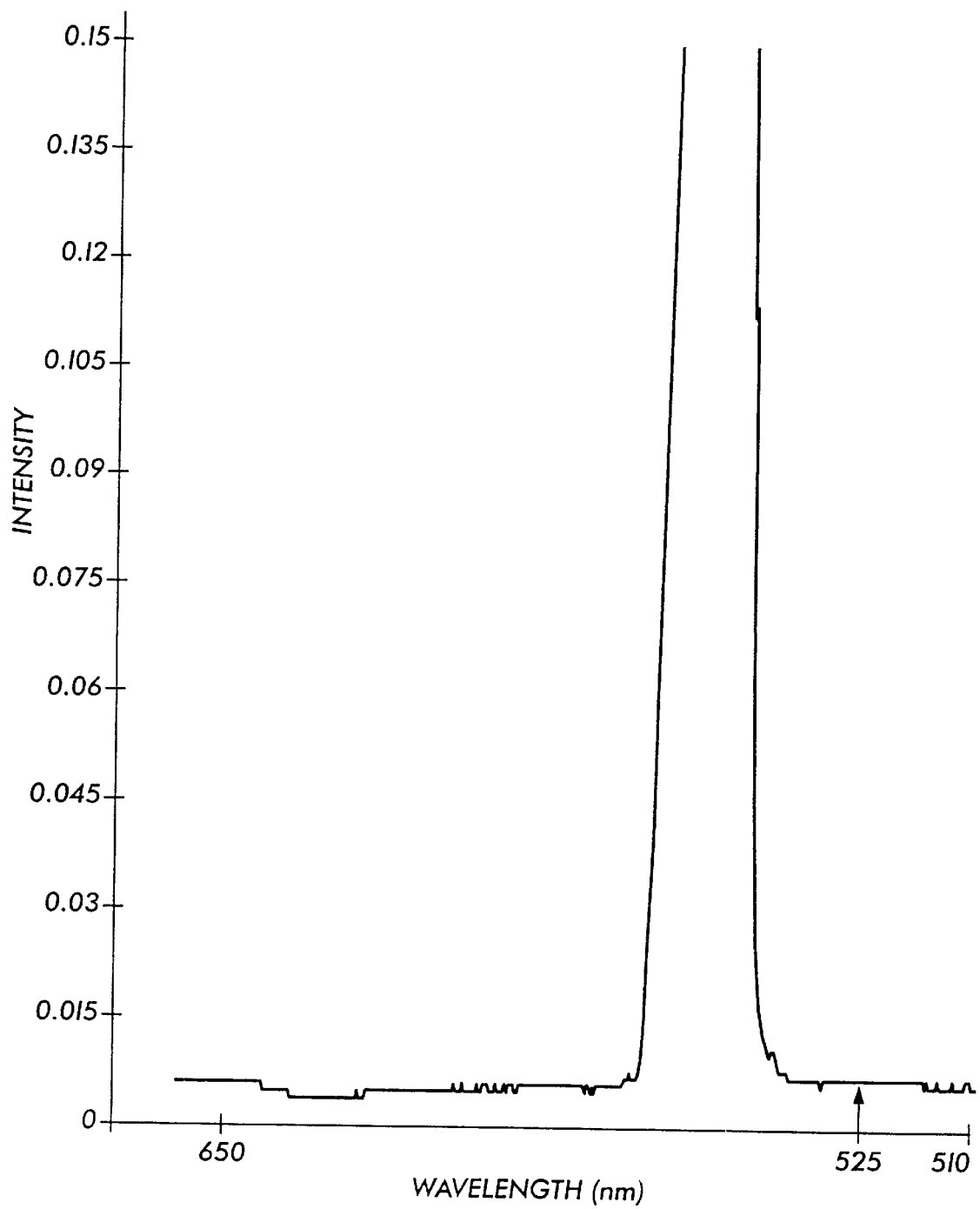
FLUORESCENCE SPECTRUM OF NEGATIVE CONTROL DNA (Seq ID No.10)
HYBRIDIZATION AT 25C FOR I HOUR A PROBE (5' CAT TCC GCT CTC) HYBRIDIZED WITH DNA (Seq ID No.3)
SAMPLE I AT 25C FOR I HOUR A PROBE (5' CAT TCC GCT CTC) HYBRIDIZED WITH DNA (Seq ID No.1)
SAMPLE 2 AT 25C FOR 1 HOUR

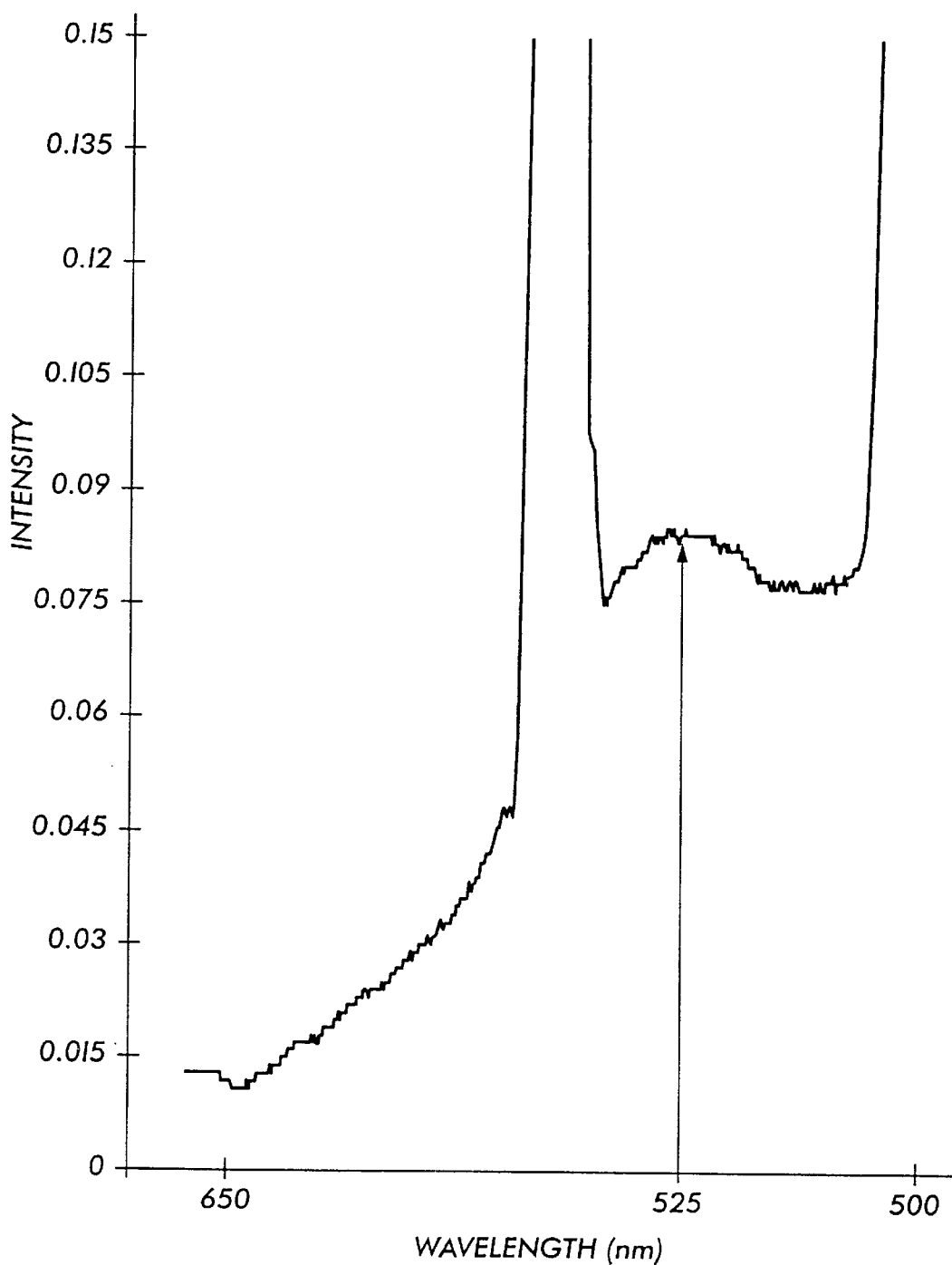
FIG.IIA
FLUORESCENCE SPECTRUM OF WT SINGLE STRANDED DNA (Seq ID No.1)
HYBRIDIZATION AT 25C FOR I HOUR FLUORESCENCE SPECTRUM OF MUTATED SINGLE STRANDED
DNA (Seq ID No.2) HYBRIDIZATION AT 25C FOR 1 HOUR

A PROBE (5' CAT TCA GCT CTC) HYBRIDIZED WITH SAMPLE I
AT 25C FOR I HOUR

A PROBE (5' CAT TCA GCT CTC) HYBRIDIZED WITH SAMPLE I
AT 25C FOR I HOUR

PNA DIAGNOSTIC METHODS

CROSS-REFERENCE TO RELATED APPLICATION

This application is a continuation-in-part of our earlier U.S. application Ser. No. 08/807,901, filed Feb. 27, 1997, and now abandoned, and entitled "ASSAYING NUCLEOTIDES IN SOLUTION USING PNA PROBES".

BACKGROUND OF THE INVENTION

1. Field of Invention

The invention relates to probes comprising peptide nucleic acids (PNAs), and to a method of using PNA probes to sequence or to assay nucleotides in solution, without solid support or adjacent double stranded nucleotide construct.

2. Description of Related Art

PNAs are polyamide analogs of DNA and RNA. See, e.g., U.S. Pat. No. 5,539,082 to Nielsen et al. Nielsen et al. discloses that PNAs mimic natural polynucleotides by binding complementary single stranded (ss) DNA and RNA strands. PNAs generally comprise ligands linked to a peptide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker.

Probes comprising PNA sequences have been employed to detect target nucleotide sequences. U.S. Pat. No. 5,503,980 to Cantor suggests employing PNA probes in a method of sequencing a nucleic acid by hybridizing the nucleic acid with a set of PNA probes containing random, but determinable, base sequences within the single stranded portion adjacent to a double stranded portion, wherein the single stranded portion of the set preferably comprises every possible combination of sequences over a predetermined range. Hybridization occurs by complementary recognition of the single stranded portion of a target with the single stranded portion of the probe and is thermodynamically favored by the presence of adjacent double strandedness of the probe.

However, although Cantor discloses that the nucleic acids can be PNAs, it does not disclose or suggest utilizing such probes in the absence of a solid support. Moreover, the present invention does not require the adjacent construct of DNA material being tested.

In addition to teaching the use of a solid support like Cantor, Perry-O'Keefe et al., "Peptide Nucleic Acid Pre-Gel Hybridization: An Alternative to Southern Hybridization," 93 Proc. Natl. Acad. Sci. USA 14670 (December 1996) also teaches that PNA does not generally bind well to double stranded DNA (dsDNA). See Perry-O'Keefe et al. at page 14673, footnote. Moreover, the homopyrimidine PNA constructs which have been found to bind dsDNA well would not be useful as probes. Applicants have discovered that the qualification which suggests that only homopyrimidine can bind with dsDNA by strand inversion is incorrect and arises from the hybridization conditions employed.

Smulevitch et al., "Enhancement of Strand Inversion by Oligonucleotides Through Manipulation of Backbone Charge," 14 Nature Biotechnology 1700 (Dec. 1996) (disclosed in Landsdorp, "Close Encounters of the PNA Kind," 14 Nature Biotechnology 1653 (Dec. 1996)) discloses using PNA primers to hybridize with dsDNA. However, Smulevitch et al. teaches the use of gels in detecting hybridization, and does not suggest the use of fluorescent markers.

Many types of sample analysis rely upon the fluorescent properties of a stain. Fluorescence occurs when a molecule excited by light of one wavelength returns to the unexcited (ground) state by emitting light of a longer wavelength. The exciting and emitted light, being of different wavelengths, can be separated from one another using optical filters, a camera or a CCD. Fluorescence has been used to visualize certain molecules (and hence structures) by light microscopy for many years, and is also used in other analytical techniques, such as flow cytometry. Further, the emission of fluorescence showing different colors can be detected by a human eye, a camera or a charge coupled device (CCD).

For example, U.S. Pat. No. 5,594,138 to Dykstra et al. discloses a method of fluorescent detection of a nucleic acid. The method comprises contacting the nucleic acid with a fluorescent marker that is a bis-dicationic aryl furan compound and exposing the nucleic acid to light at a frequency inducing fluorescence of the fluorescent marker. The fluorescent marker may be conjugated to a nucleotide sequence as a probe for hybridization studies, or it may be conjugated to numerous reagents for in situ labeling studies.

U.S. Pat. No. 4,963,477 to Tchen discloses a probe of high sensitivity containing a modified nucleic acid, which can be recognized by specific antibodies.

Fluorescent In Situ Hybridization (FISH) is a technique comprising detecting fluorescent probe binding to human chromosomes by attaching DNA to a solid support, such as a glass slide. See, e.g., K. H. Andy Choo, Ed., "In Situ Hybridization Protocols," Chapters 2 and 4 (Humana Press, Totowa, N.J., 1994). Like all other conventional detection methods comprising hybridization with probes, this method relies on the solid support to keep the two complementary strands of DNA apart while the probe hybridizes with one of the strands. In addition, FISH requires a complicated buffer and temperature control protocol, with overnight incubation.

Until the present invention, however, it has not been possible to rapidly test for the presence of nucleotide sequences in solution using a method which does not destroy the sample, is less hazardous to laboratory personnel than radiation based assays, does not require the cost and delay of preparing solid supports, and is readily automated. Time and cost efficient detection of mutant genetic sequences has been the rate limiting step in correlating mutant genotypes with altered phenotypes. Although conventional DNA sequencing methods have been considered to be the most accurate means of identifying mutations, these methods have been relatively slow and labor intensive, and are not particularly well-suited to rapidly screening large numbers of samples of genomic DNA.

All references cited herein are incorporated herein by reference in their entireties.

SUMMARY OF THE INVENTION

The present invention provides methods for detecting nucleic acid sequences and/or determining sequence information from nucleic acids. Probes according to the present invention include PNA.

The invention provides a method for detecting at least one single stranded or double stranded nucleotide sequence in a liquid medium, the method comprising adding to the liquid medium at least two different PNA probes having at least one marker each to form at least one hybridization complex with at least one nucleotide sequence in the medium, detecting the at least one nucleotide sequence by detecting at least one signal correlated with an amount of the at least one hybridization complex in the liquid medium, wherein the method is entirely conducted in the liquid medium without binding the PNA probes, the at least one nucleotide sequence or the at least one hybridization complex to a solid support or gel.

BRIEF DESCRIPTION OF THE DRAWINGS

The invention will be described in conjunction with the following drawings in which like reference numerals designate like elements and wherein:

FIGS. 2, 3A, 3B, 3C, 4A, 4B, 4C, 5A, 5B, 6A, 6B, 7A, 7B, 8A, 8B, 8C, 9A, 9B, 9C, 9D, 10A, 10B, 11A, 11B, 12A, 12B, 13A, 13B, 13C, 14A, 14B, 15A, 15B, 16A, 16B, 16C, 16D, 17A, 17B, 17C, 18A, 18B, 19A, 19B, 19C, 19D and 19E are fluorescent spectra.

DETAILED DESCRIPTION OF PREFERRED EMBODIMENTS

Figure 1:
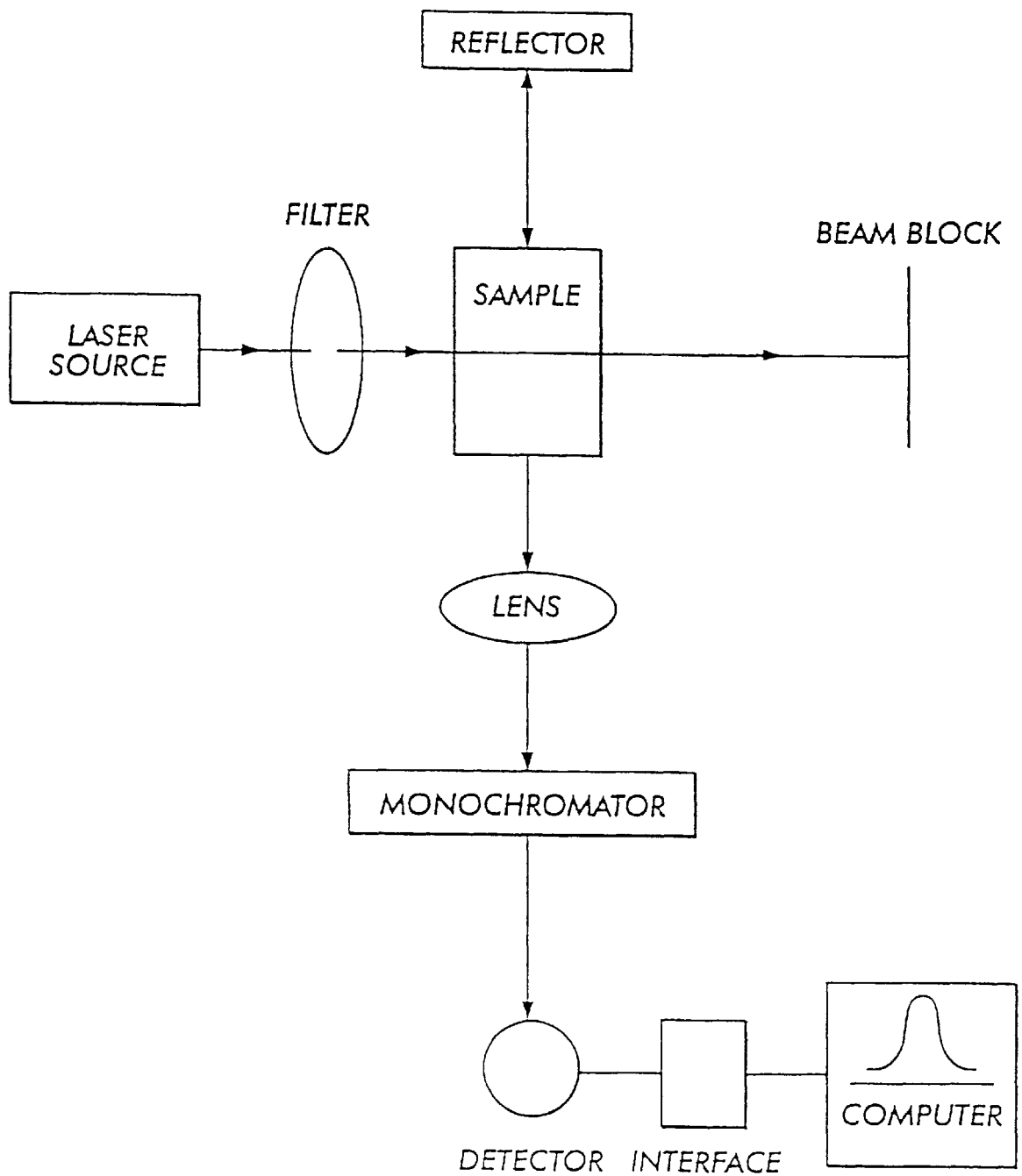
FIG. 1 is a schematic depiction of an apparatus according to the invention.

The invention utilizes PNA probes to detect and/or characterize nucleotide sequences in a sample. PNA probes are able to recognize dsDNA by binding one strand, thereby presumably hybridizing with the other strand to generate a PNA-DNA complex. Such recognition can take place to dsDNA target sequences 20 or more base pairs long. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. However, a plurality of shorter probes can be used to detect a nucleotide sequence having a plurality of non-unique target sequences therein, which combine to uniquely identify the nucleotide sequence.

The probes of the invention are able to form triplex complexes with dsDNA and duplex complexes with RNA or ssDNA. The compounds of the invention are also able to form triplex complexes wherein a first PNA probe binds with RNA or ssDNA and a second ssDNA strand binds with the resulting duplex complex. See, e.g., Egholm et al., "PNA Hybridizes to Complementary Oligonucleotides Obeying the Watson-Crick Hydrogen-Bonding Rules," 365 Nature 566 (1993), and Tomac et al., "Ionic Effects on the Stability and Conformation of Peptide Nucleic Acid Complexes," 118 J.Am.Chem.Soc. 5544 (1996).

In the PNA probes according to the invention, the bases attached to the polyamide backbone are primarily naturally occurring nucleobases attached at the position required by probe manufacture. Alternatively, the bases may be non-naturally occurring nucleobases (nucleobase analogs), other base-binding moieties, aromatic moieties, (C1–C4) alkanoyls, hydroxyls or even hydrogens. It will be understood that the term nucleobase includes nucleobases bearing removable protecting groups. Furthermore, at least one base on the polyamide skeleton can be replaced with, or substituted with, a DNA intercalator, a reporter ligand such as, for example, a fluorophore, radio label, spin label, hapten, or a protein-recognizing ligand such as biotin. Preferred detectable labels include a radioisotope, a stable isotope, an enzyme, a fluorescent chemical, a luminescent chemical, a chromatic chemical, a metal, an electric charge, or a spatial structure.

In particularly preferred embodiments, the PNA probe comprises a PNA sequence covalently bonded to a fluorescent marker, which fluoresces when irradiated with a laser. Preferred fluorescent markers include biotin, rhodamine and fluorescein.

It is preferred to provide the fluorescent marker at the 5' terminal of the PNA with a short linker to minimize interaction with the PNA.

In order to distinguish a mutant nucleotide sequence from a reference nucleotide sequence, wherein the two sequences differ by as little as a single base, it is preferred to design the PNA probe so that the mutant portion of the mutant nucleotide corresponds to the center of the PNA probe. This design results in a higher hybridization yield and a more stable hybrid than when the mutant portion of the nucleotide corresponds to a terminus of the probe, since the bonding mismatch between probe and nucleotide is located centrally within the probe.

PNA probes are added to a liquid medium suspected of containing at least one nucleotide sequence, and/or a mutant version of the at least one sequence. The liquid medium can be any conventional medium known to be suitable for preserving nucleotides. See, e.g., Sambrook et al., "Molecular Cloning: A Lab Manual," 2d (1989). For example, the liquid medium can comprise nucleotides, water, buffers and surfactants.

The nucleotides in the liquid medium can be obtained from clinical samples by any conventional method, including an automated method. Examples of such methods are summarized in, e.g., Sambrook et al., Vol. 2, pp. 9.16–9.19 and 7.6 to 7.7. An example of an automated nucleic acid purifying apparatus is the BioRobot 9600 manufactured by Quiagen.

For example, a variety of diseases are known to be linked with the presence of mutant DNA in an individual's genome. If the sequences of the wild type DNA and the mutant DNA are known, it is possible to isolate these nucleotide sequences from clinical samples using conventional technology. PCR is the preferred method of isolating nucleotides from clinical samples. PCR is conducted using a primer which is capable of amplifying the wild type DNA and the mutant DNA.

The nucleotide sequences are added to the liquid medium in a known concentration, since the concentration can affect the magnitude of the signal (e.g., fluorescent intensity) generated in subsequent steps in the inventive method. The nucleotide concentration can be determined by, e.g., measuring the UV absorption at 260 nm.

The isolated nucleotides are added to the liquid medium and denatured prior to being detected. Preferably, the denaturation is conducted at about 90° C. to about 100° C. from about 30 seconds to about 5 hours in the presence of PNA probe.

Preferably, PNA probes are added to the liquid medium in a concentration 1 to 20 times the concentration of the nucleotide sequence to be detected.

Hybridization between complementary bases occurs under a wide variety of conditions having variations in temperature, salt concentration, electrostatic strength, and buffer composition. Examples of these conditions and methods for applying them are known in the art. See, e.g., Perry-O'Keefe et al., Egholm et al., Tomac et al., Sambrook et al., Vol. 2 pp. 9.47–9.55 and the Pre-Gel Hybridization Technique taught in Vol. 4, No. 3 of PerSeptive Biosystems Magazine.

It is preferred that hybridization complexes be formed at a temperature of about 4° C. to about 75° C. for about 2 minutes to about 24 hours. It is particularly preferred to conduct denaturing for no more than 60 minutes in the presence of PNA probe, after which the temperature is passively cooled to room temperature without quenching.

It is possible to facilitate hybridization in solution by using certain reagents. Preferred examples of these reagents include single stranded binding proteins such as Rec A protein, T4 gene 32 protein, *E. coli* single stranded binding protein, major or minor nucleic acid groove binding proteins, divalent ions, polyvalent ions, and intercalating substances such as ethidium bromide, actinomycin D, psoralen, and angelicin.

In embodiments of the inventive method, hybridization complexes are separated from unhybridized PNA probes prior to detecting the signal of the hybridized PNA probes. The separation is accomplished by at least one of filtration, centrifugation, precipitation, ion exchange resin separation and free solution electrophoresis (i.e., electrophoresis in a liquid medium as opposed to gel electrophoresis).

Separation can be accomplished by G50 column. After hybridization, the mixture of hybridization complexes and unhybridized DNA and PNA is transferred into a G50 column. The column is centrifuged at 500 to 1000 rpm for 1 to 2 minutes. The unbound PNA is filtered and retained in the column. The solution with the hybrids of PNA-DNA is passed through column and collected in a cuvette.

In fact, centrifugation can be avoided. The solution can flow through the column by gravity or washing using extra amounts of buffer. However, centrifugation is for the purpose of reducing the separation time and avoiding the sample being diluted.

Separation can be accomplished by centrifugation. After the hybridization, the sample (without transferring) is separated into two layers (gradient) by centrifugation at 1000 to 10000 rpm for 4 to 20 hours. The lighter unhybridized PNA is abundant in the upper layer, while the heavier hybridization complex is concentrated in the lower layer. The lower layer is collected in a cuvette for fluorescence measurement.

In certain embodiments, a filtration step is avoidable if an electrical method is used to concentrate hybridized PNA. In these embodiments, an electric field is applied to the liquid medium prior to or concurrently with detecting the desired nucleotide sequence, and a change in an intensity of fluorescent emission as a function of the electric field is detected as an indication of whether the PNA probe is hybridized to at least one of a completely complementary nucleotide sequence and an incompletely complementary nucleotide sequence.

The preferred markers for use in the invention are fluorophores. As will be appreciated by the skilled artisan, the wavelength preferably selected to induce fluorescence of the fluorescent marker is known in the art as the "excitation maximum," i.e., that wavelength which is absorbed by a molecule and excites that molecule to a higher electronic state. When the marker molecule passes from the higher to a lower electronic state, the molecule emits a type of visible radiation, i.e., fluorescence, at a wavelength referred to as the "emission maximum." It is this fluorescence that is detected in the present invention. The detectable signal emitted by the compound can be detected using techniques known in the art, for example by observation with the human eye, using electronic means for detecting a generated wavelength (e.g., cameras and CCDs), and the like. Advantageously, the wavelength of fluorescence is sufficiently removed from that of the exciting light to allow good separation of the two wavelengths by optical filters.

The excitation wavelength is selected (by routine experimentation and/or conventional knowledge) to correspond to this excitation maximum for the marker being used, and is preferably 400 to 1000 nm, more preferably 400 to 750 nm. For example, when the marker is fluoroscein, the preferred wavelength of excitation is about 488 nm.

In preferred embodiments, an argon ion laser is used to irradiate the marker with light having a wavelength in a range of 400 to 520 nm, and fluorescent emission is detected in a range of 500 to 750 nm. The duration of irradiation is preferably about 10 milliseconds to about 1 minute.

An apparatus for performing the inventive method can comprise a liquid medium container for containing the liquid medium; a laser for irradiating the nucleotide; a fluorescence detector for detecting fluorescence induced by the laser; a data analysis device for analyzing data generated by the fluorescence detector; and an output device which reports the data analysis generated by the data analysis device. See, e.g., FIG. 1, which shows a schematic diagram of a fluorescence detection system suitable for use with the method of the invention.

In certain embodiments, fluorescent emission generated by irradiating hybridized PNA probes with a light source is distinguished from fluorescent emission of unhybridized PNA probes, without separating hybridized and unhybridized PNA probes. In certain embodiments, the fluorescent emission of one type of PNA probe hybridized to one nucleotide sequence is distinguished from the fluorescent emission of another type of PNA probe hybridized to a nucleotide sequence other than the first nucleotide sequence. For example, the presence of either of two nucleotide sequences differing by as little as a single nucleotide can be detected on the basis that a fluorescent PNA probe precisely complementary to one of the two nucleotides will bond more effectively with the precise complement than with the imprecise complement, thus providing a higher concentration of hybridization complexes in solution and a higher fluorescent intensity after removal of unhybridized PNA probe.

A plurality of PNA probes can be employed simultaneously to achieve a variety of effects. Several probes targeted for different segments of a single nucleotide sequence can be employed to enhance the reliability of the detection method. Similarly, one probe can target one strand of dsDNA, while another probe can target the complementary strand of dsDNA.

A preferred method of detecting whether DNA is mutant type or the correspondng wild type comprises the simultaneous use of (a) a first type of PNA probe targeted to a sequence that occurs in both the wild type and mutant type DNA but is otherwise unique, and (b) a second type of PNA probe targeted to a sequence unique to the mutant type DNA, wherein the first and second types of PNA probe have different markers that produce distinguishable signals. Thus, detection of the first probe signal indicates that the test was run properly (i.e., the first probe functions as a positive control) and detection of the second probe signal indicates that the mutant type DNA is present. For example, one probe can have a fluorescein marker exhibiting a fluorescent emission intensity peak at 525 nm while the other probe can have a rhodamine marker exhibiting a fluorescent emission intensity peak at 580 nm.

In contrast to prior art detection methods, the present invention makes it possible to limit the total volume of the liquid medium (i.e., the sample to be analyzed) in certain embodiments to no more than about 200 microliters. It is also possible to limit the total volume in certain embodiments to no more than about 10 microliters.

When testing for mutant dsDNA using PNA, if a result is obtained for which there remains doubt, a further test may be immediately performed on the sample by adding the complementary PNA probe to test the complementary strand of DNA. If centrifuged as part of the first test, the sample would be removed to a new tube and hybridized with the complementary PNA. Alternatively, the PNA test can be done with both the PNA and complementary PNA probes hybridized to each of the denatured DNA strands in the first instance and at the same time.

For forensic applications, samples can be tested, stored and then retested because PNA is expelled from hybridization over a couple of days, and DNA recombines over time and does not degrade by this procedure. Accordingly, a sample frozen after testing can be subsequently retested in the same tube a number of times.

FIG. 2 shows DNA hybridization over time. A PNA probe was allowed to hybridize with wild type DNA (WT DNA) and mutant DNA (MT DNA). Hybridization between the probe and the DNA was followed over time by measuring fluorescent intensity. FIG. 2 shows that hybridization of the PNA probe with the DNA eventually decreases over time, suggesting that the DNA resumes its native structure over time by displacing PNA.

Clinical samples can be tested using at least 100 times less chemicals or genomic material (100 microliters vs. 10 milliliters) than is typical in conventional methods. Therefore, even using 10 or 20 times the concentration of PNA conventionally used, the tests still only consume 1/5th to 1/10th the amount of PNA, while obtaining a very decisive result.

The invention will be illustrated in more detail with reference to the following Examples, but it should be understood that the present invention is not deemed to be limited thereto.

EXAMPLE 1

A 150 bp (base pair) fragment of genomic DNA from wild type p53 gene (SEQ ID NO:1) was amplified by PCR. PCR was conducted using a GeneAmp PCR system 2400 from Perkin Elmer, with a hot start at 95° C. for 5 minutes. After adding Taq enzyme, 35 cycles were carried out as follows:

Denaturing: 94° C. for 30 mins.

Annealing: 45° C. for 45 mins. (45° C. is 5° C. lower than the primer Tm)

Extension: 72° C. for 30 mins. (1 kb/min.)×35.

PCR was conducted using a mixture comprising in 100 ml volume 10× reaction buffer (10 μl), 20 mM of $MgCl_2$ (10 μl), 10 mM of dNTP mixture (2), 25 pmol/μl of primer 1 (1 μl), 25 pmol/μl of primer 2 (1 μl), 100 μg/μl of DNA template (1 μl), dd $H_2O$ (74 μl) and Taq polymerase (1 μl) (5 unit/μl).

Similarly, a mutant fragment (SEQ ID NO:2) of the same genomic 150 bp fragment was also amplified by PCR. The mutant fragment was identical to the wild type fragment except for a point mutation at amino acid position 344 at which the DNA wild type sequence CTG was changed to CAG.

A 12-mer PNA probe was obtained from PerSeptive Biosystems, Inc. (Framingham, Mass., USA) and was designed to be complementary to a 12 nucleotide segment of the 150 bp p53 wild type fragment (SEQ ID NO:1). The probe had the following structure:

5' H-FluO CAT TCA GCT CTC Lys -$CONH_2$

The buffer solution for hybridization was 10 mM Tris-HCl, pH 7.1, 1% by weight BSA (bovine serum albumin), and 0.1% Triton X-100 (t-octylphenoxypolyethoxyethanol). 50 pmol of wild type genomic DNA was added to 300 pmol of PNA probe and mixed in 100 ml of buffer. 50 pmol of mutant genomic DNA was added to 300 pmol of PNA probe and mixed in 100 microliters of buffer.

Each sample was heated at 95° C. for 30 minutes. Each sample was then added to buffer preheated to 30° C. and allowed to hybridize for 1 hour.

Figure 3A:
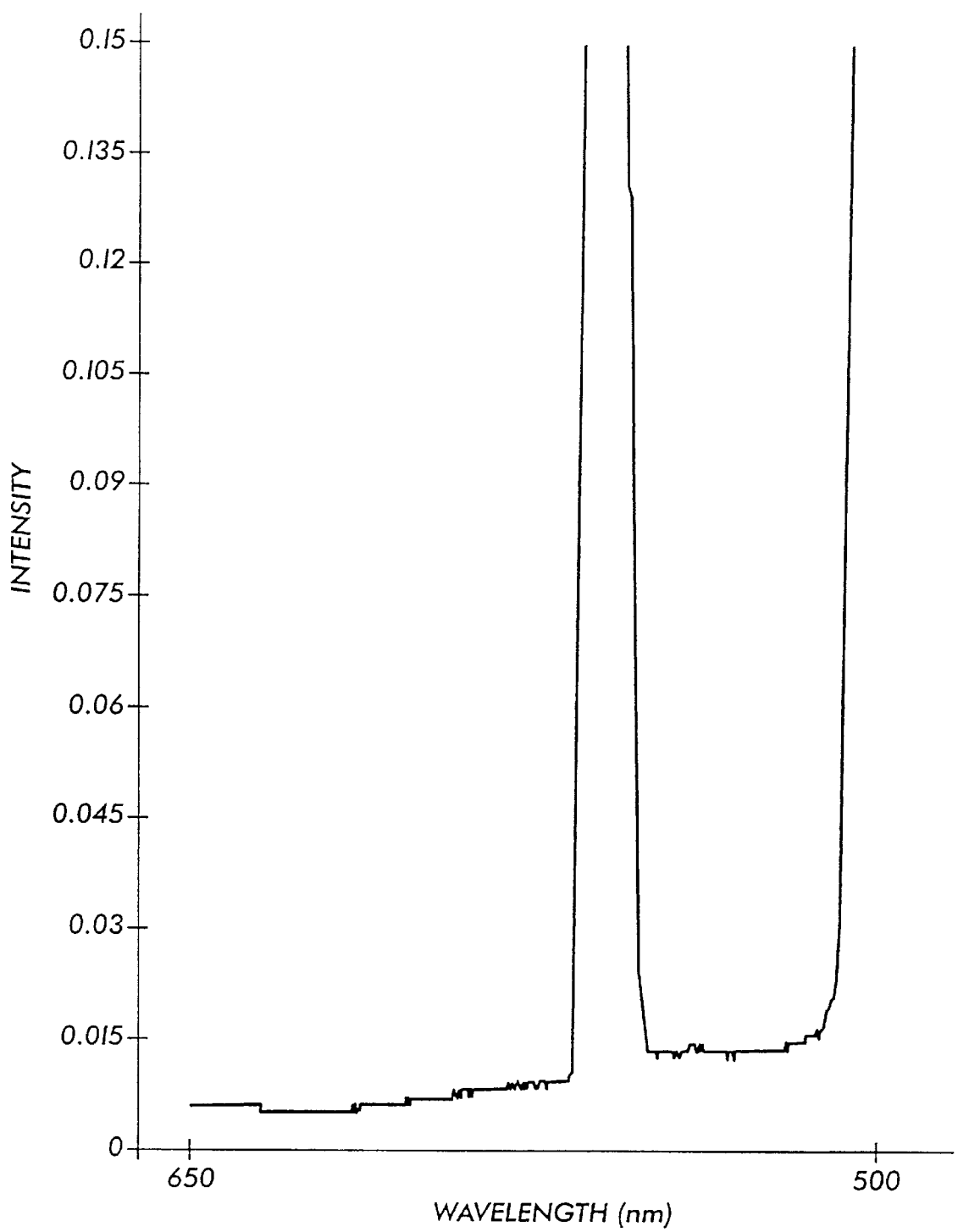
Figure 3B:
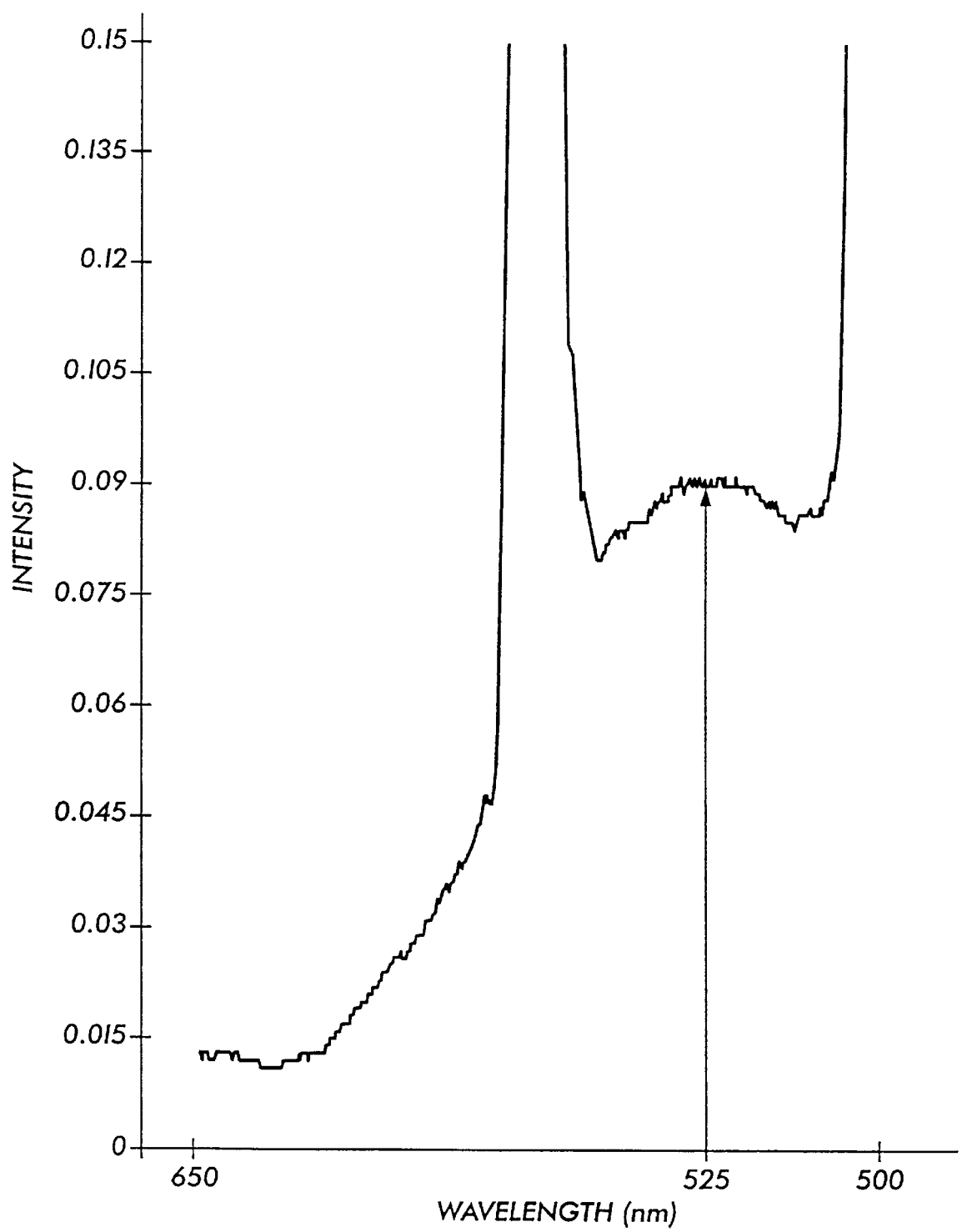
Figure 3C:
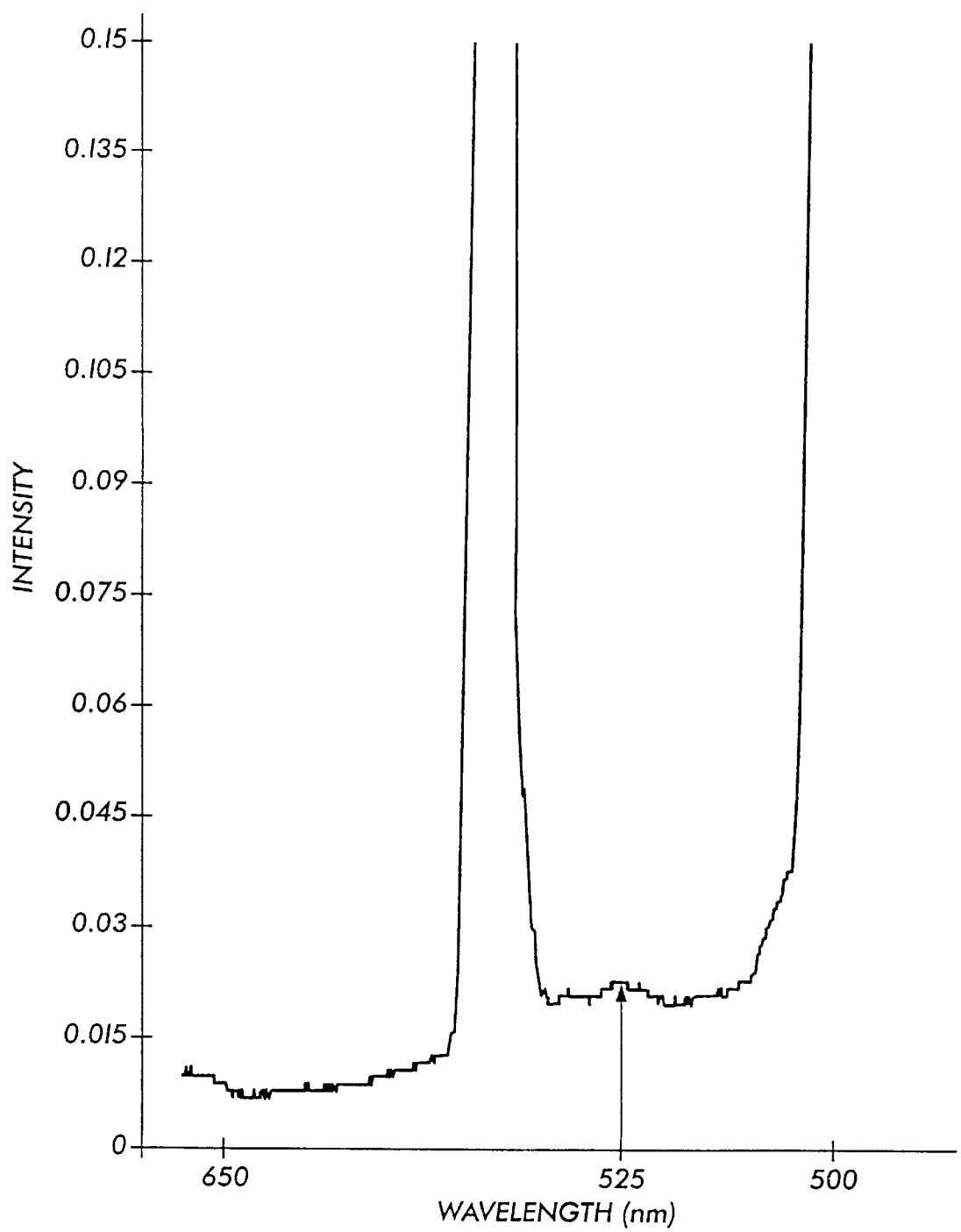

The components of each sample were separated by G50 spin columns (Pharmacia Biotech, Uppsala, Sweden) by spinning at 600g for 2 minutes. The unbound PNA was filtered and retained in the column. The solution with the hybrids of PNA-DNA passed through the column and was collected in a cuvette for fluorescent detection. The cuvette was then placed in a fluorescence spectrometer for laser induced fluorescence (irradiation wavelength of 488 nm in all of the Examples) and detection of the fluorescent probe attached to the target genomic DNA. As shown in FIGS. 3B and 3C, the relative fluorescence intensity at 525 nm of the wild type genomic DNA sample (FIG. 3B) was four times higher than that of the mutant sample (FIG. 3C), allowing the mutant genomic DNA sample to be distinguished from the wild type genomic DNA sample. FIG. 3A shows the fluorescent intensity of the probe alone.

EXAMPLE 2

Figure 4A:
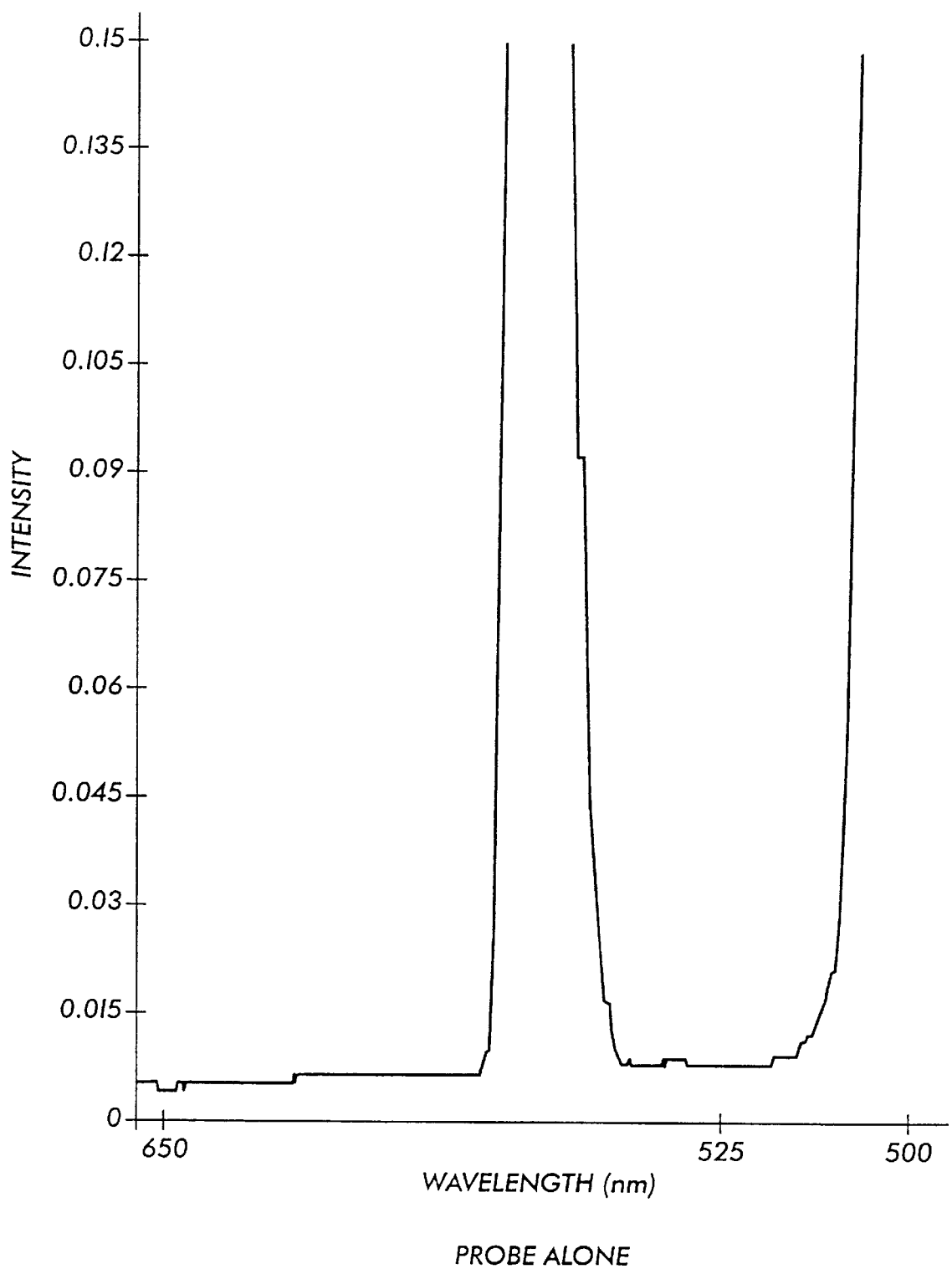
Figure 4B:
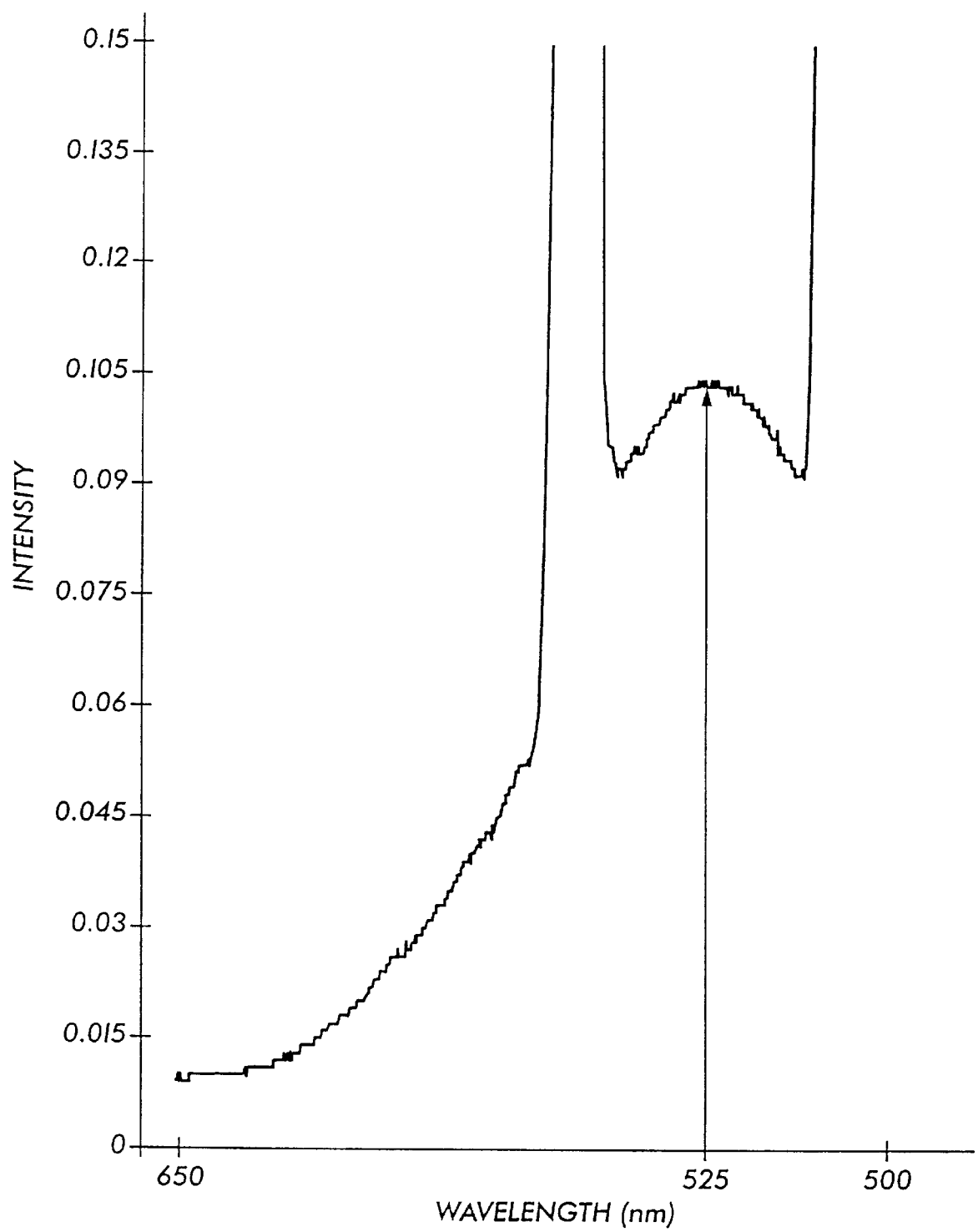
Figure 4C:
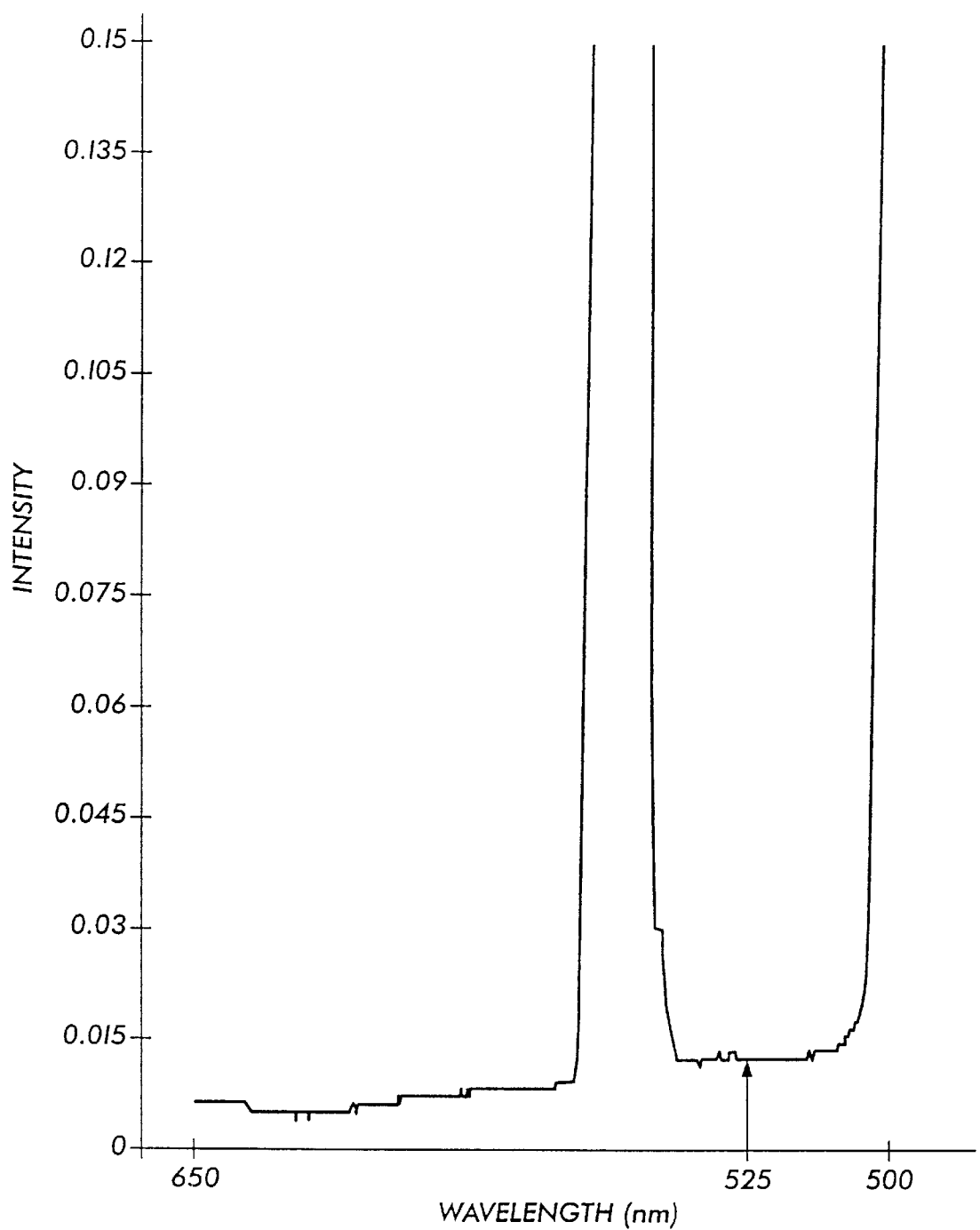

This Example was similar to Example 1 except for the following details. The mutant genomic DNA sample (SEQ ID NO:3) had the base sequence at amino acid position 344 changed from the wild type sequence CTG to CGG. Both samples were heated at 94° C. for 20 minutes. The buffer was preheated to 25° C. and the samples were allowed to hybrid for 30 minutes. The components of each sample were separated by using G50 spin columns and spinning at 800 rpm for 1.5 minutes. The relative intensity at 525 nm of the detected fluorescence from the wild type genomic DNA sample (FIG. 4B) was six times higher than that of the mutated genomic DNA sample (FIG. 4C), allowing the wild type genomic sample to be distinguished from the mutated genomic sample. FIG. 4A shows the fluorescent intensity of the probe alone in the solution.

EXAMPLE 3

Figure 5A:
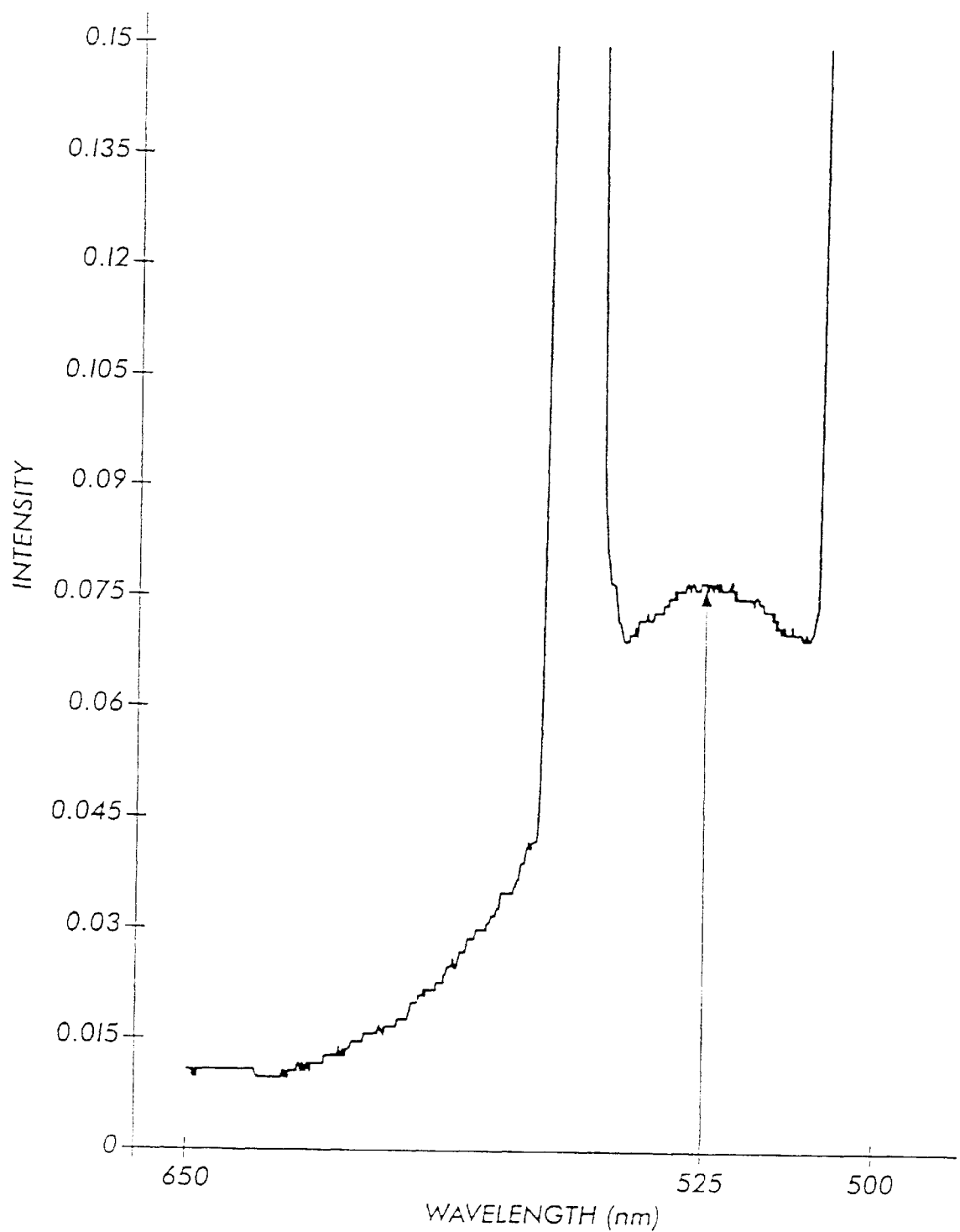
Figure 5B:
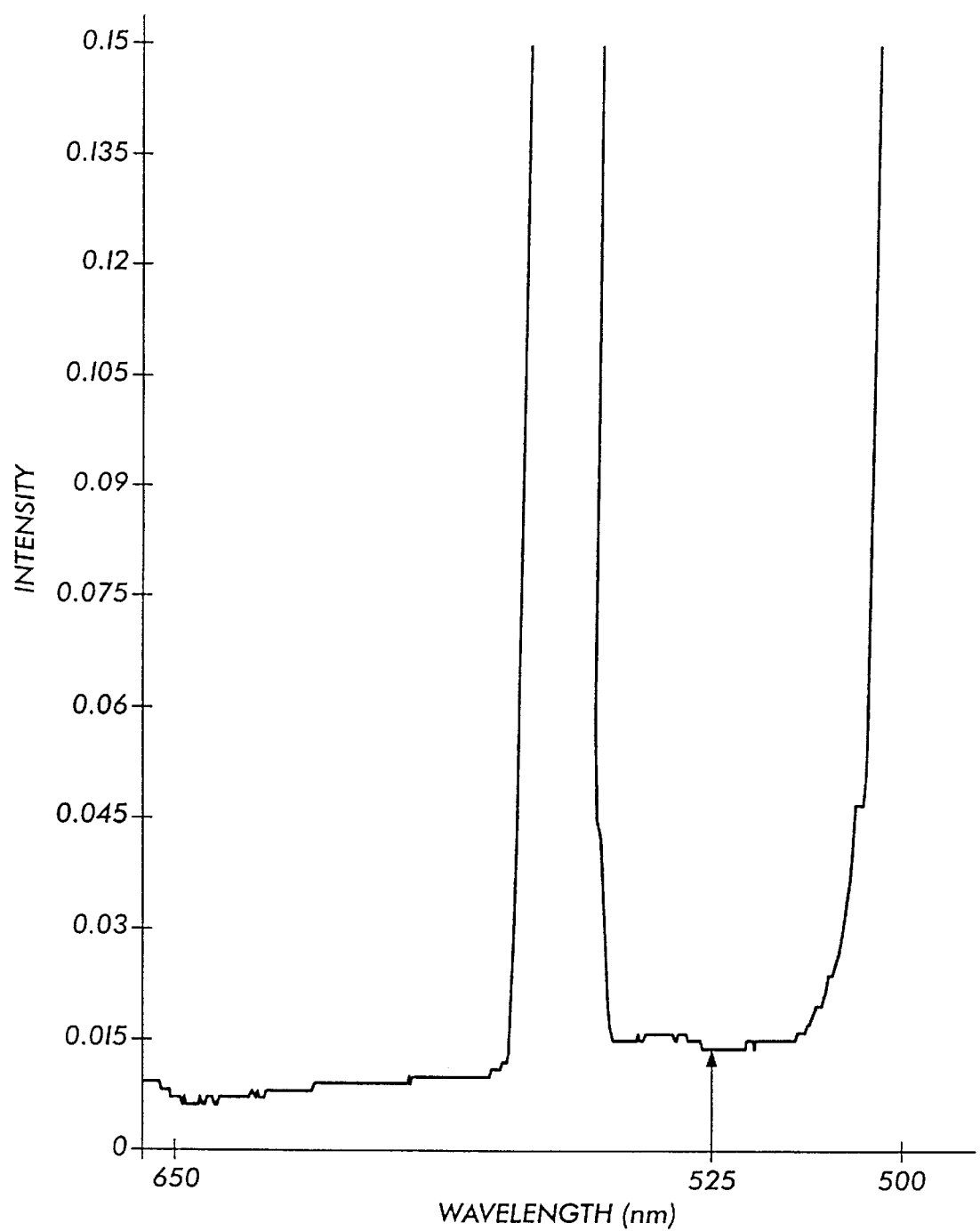

This Example was similar to Examples 1 and 2 except for the following details. The mutant genomic DNA sample (SEQ ID NO:4) had a 2 base change from the wild type genomic DNA at amino acid position 344, from CTG to AAG. Each sample was initially heated at 100° C. for 45 minutes. The buffer was preheated to 45° C. and each sample was allowed to hybridize for 20 minutes. The components of each sample were separated by using G75 spin columns and spinning at 1000 rpm for 1 minute. The relative intensity at 525 nm of the detached fluorescence from the wild type genomic DNA sample (FIG. 5A) was eight times higher than that of the mutated genomic sample (FIG. 5B), allowing the wild type genomic sample to be distinguished from the mutated genomic sample.

EXAMPLE 4

Figure 6A:
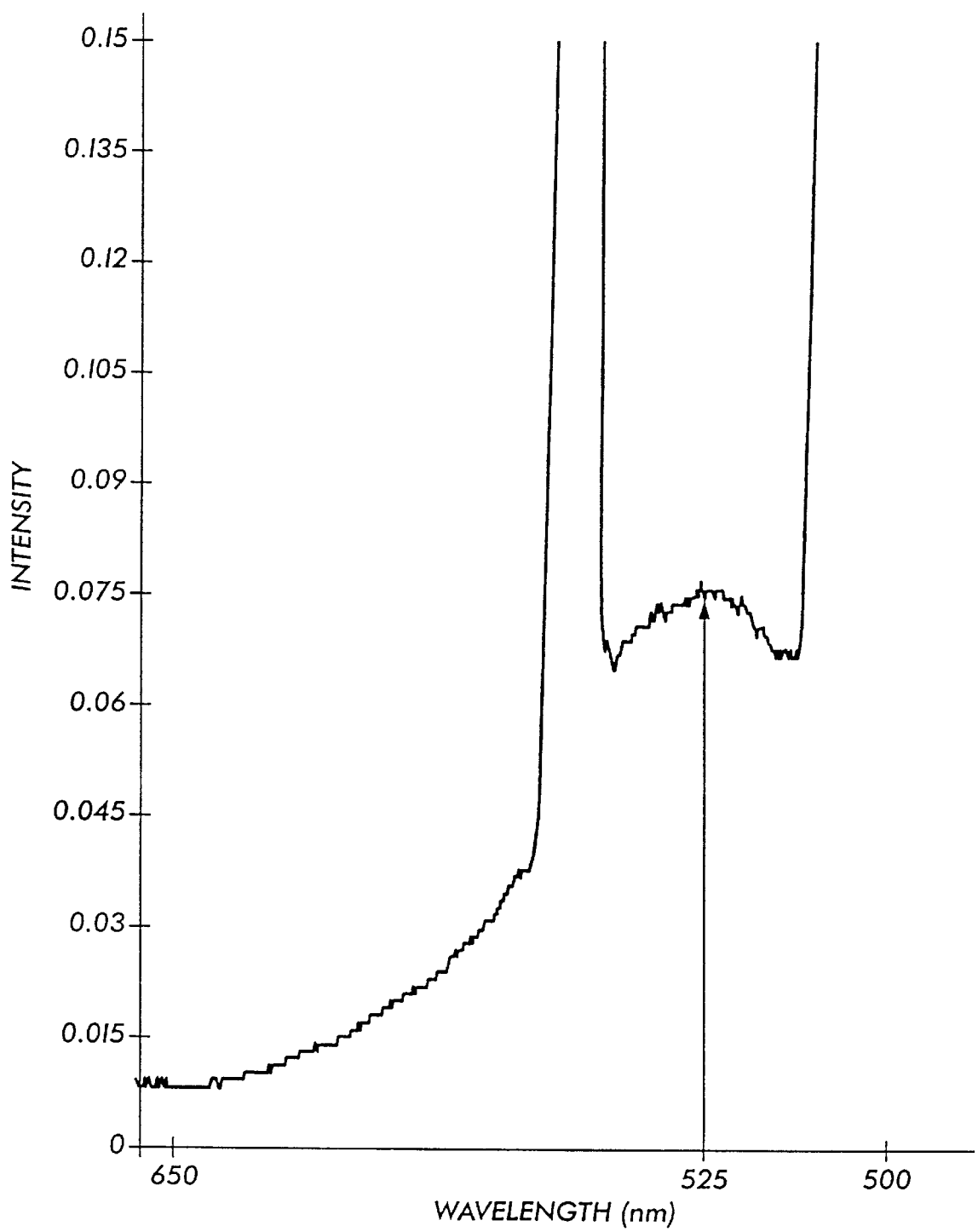
Figure 6B:
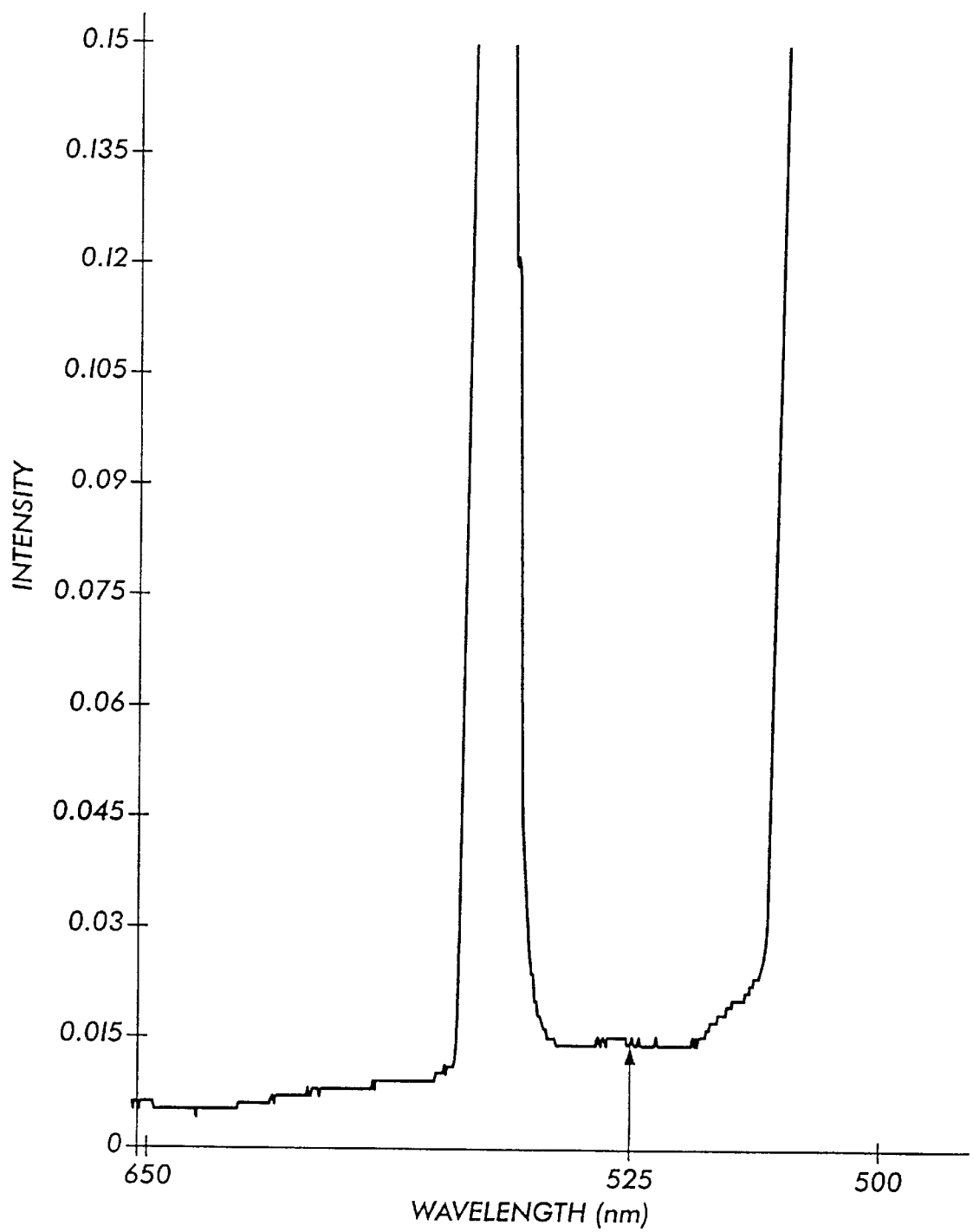

This Example was similar to Example 3 except for the following details. The mutant genomic DNA sample (SEQ ID NO:5) had a 2 base change from the wild type genomic DNA at amino acid position 344, from CTG to GCG. Each sample was initially heated at 100° C. for 15 minutes. The buffer was preheated 50° C. and each sample was allowed to hybridize for 2 hours. The components of each sample were separated using G50 spin columns and spinning at 1200 rpm for 1 minute. The relative intensity at 525 nm of the detected fluorescence from the wild type genomic DNA sample was seven times higher than that from the mutated genomic sample, allowing the wild type genomic sample (FIG. 6A) to be distinguished from the mutated genomic sample (FIG. 6B).

EXAMPLE 5

Figure 7A:
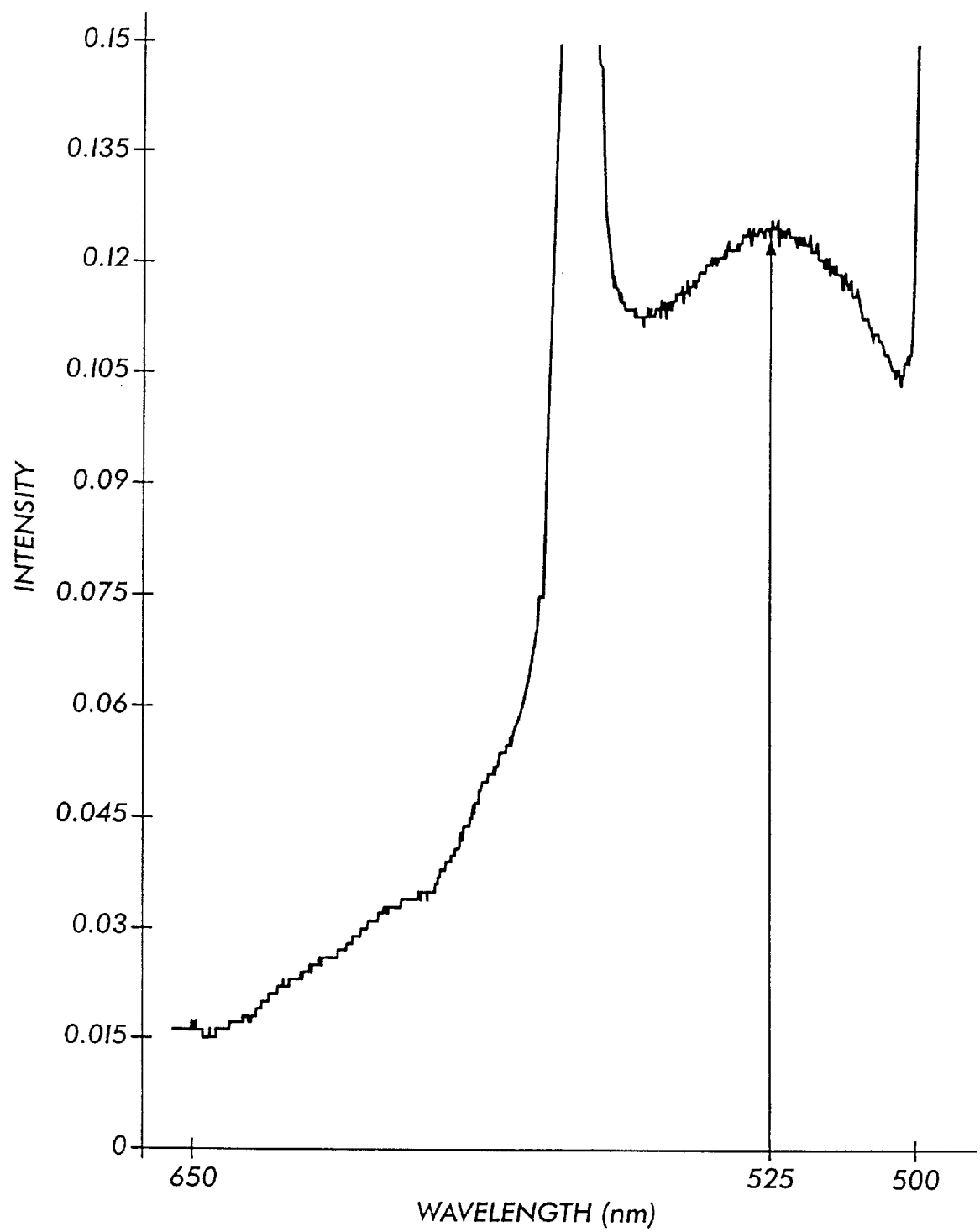
Figure 7B:
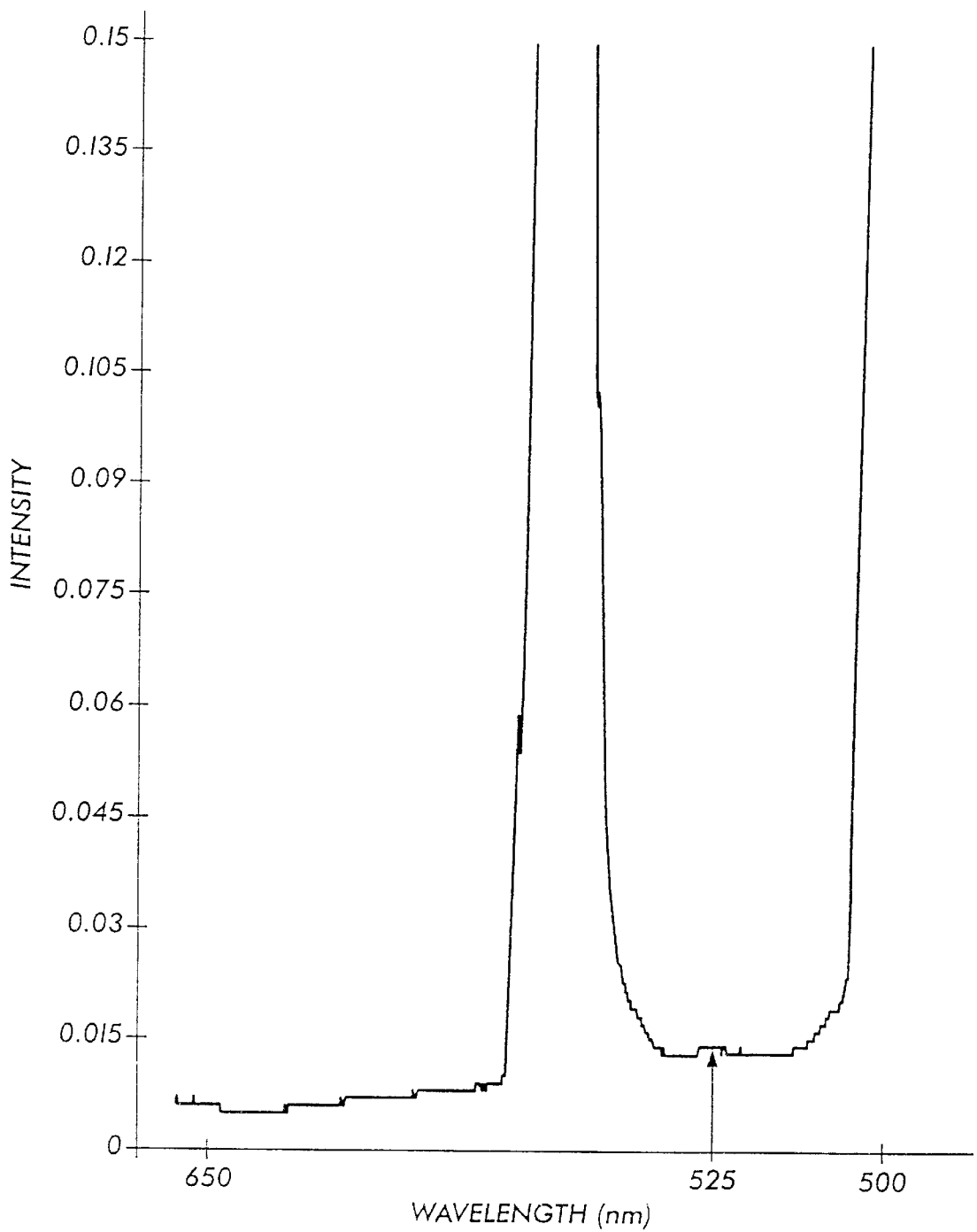

This Example was similar to the other Examples except for the following details. The mutant genomic DNA sample (SEQ ID NO:6) had a 3 base change from the wild type genomic DNA at amino acid position 344, from CTG to TAC. Each sample was initially heated at 95° C. for 30 minutes. The buffer was preheated to 25° C. and each sample was allowed to hybridize for 60 minutes. The components of each sample were separated using G50 spin columns and spinning at 750 rpm for 2 minutes. As shown in FIGS. 7A and 7B, the relative intensity at 525 nm of the detected fluorescence from the wild type genomic DNA sample (FIG. 7A) was ten times higher than that from the mutated genomic sample (FIG. 7B), allowing the wild type genomic sample to be distinguished from the mutated genomic sample.

EXAMPLE 6

This Example was similar to Example 1 except for the following details. 100 pmol of the 12 bp PNA of Example 1 labeled with fluorescein (PerSeptive Biosystems), 25 pmol of 150 bp PCR amplified dsDNA, including wild type (CTG) (SEQ ID NO:1) and one base mutated DNA (CAG, SEQ ID NO:2, and CGG, SEQ ID NO:3) and 115 microliters buffer (0.5×TBE working solution (0.0225M Trisborate/ 0.0005M EDTA), pH 6.5) were mixed at room temperature. The mixture was then heated for 30 minutes at 95° C. and hybridized at room temperature for about 1 hour.

Two metal wires serving as electrodes were placed into each sample. Fluorescent intensity was monitored at 525 nm while a voltage of 5 volts at a current of 10 mA was switched on and off, with an electrode separation of about 7 or 8 mm. When the voltage was applied, the DNA and DNA-PNA migrated to the anode, since the DNA is negative charged, while the unbound PNA did not migrate, since it is neutral.

Figure 8A:
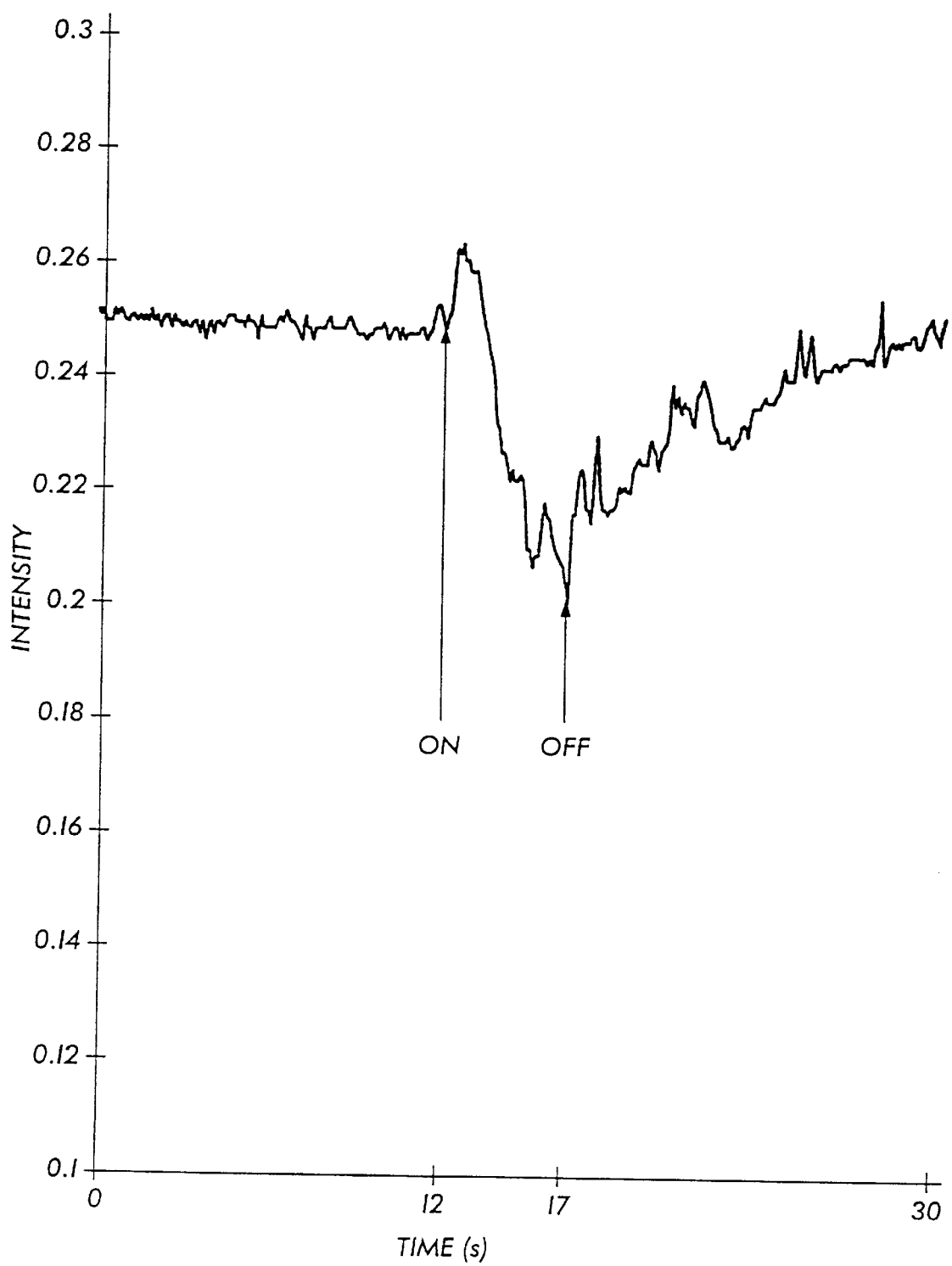

FIG. 8A shows the fluorescent spectrum of the wild type DNA. After hybridizing at 25° C. for 1 hour, the solution was transferred into a cuvette. The cuvette was placed in a fluorescence spectrometer and then two electrodes were put into the solution for detecting the change of fluorescent intensity at a wavelength of 525 nm with the applied electric field. The fluorescent intensity at 525 nm decreased with the application of the voltage and increased with the removal of the voltage.

Figure 8B:
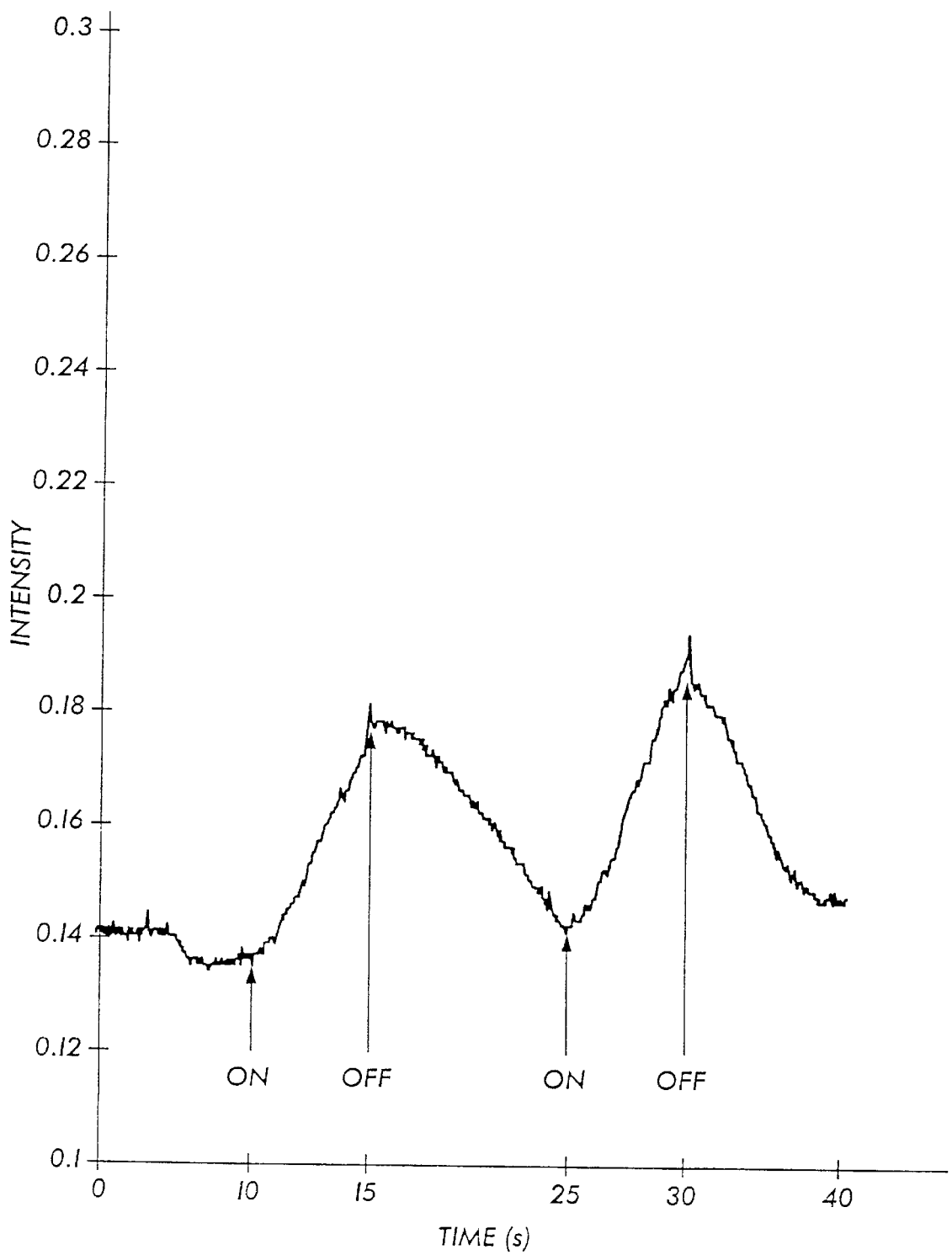
Figure 8C:
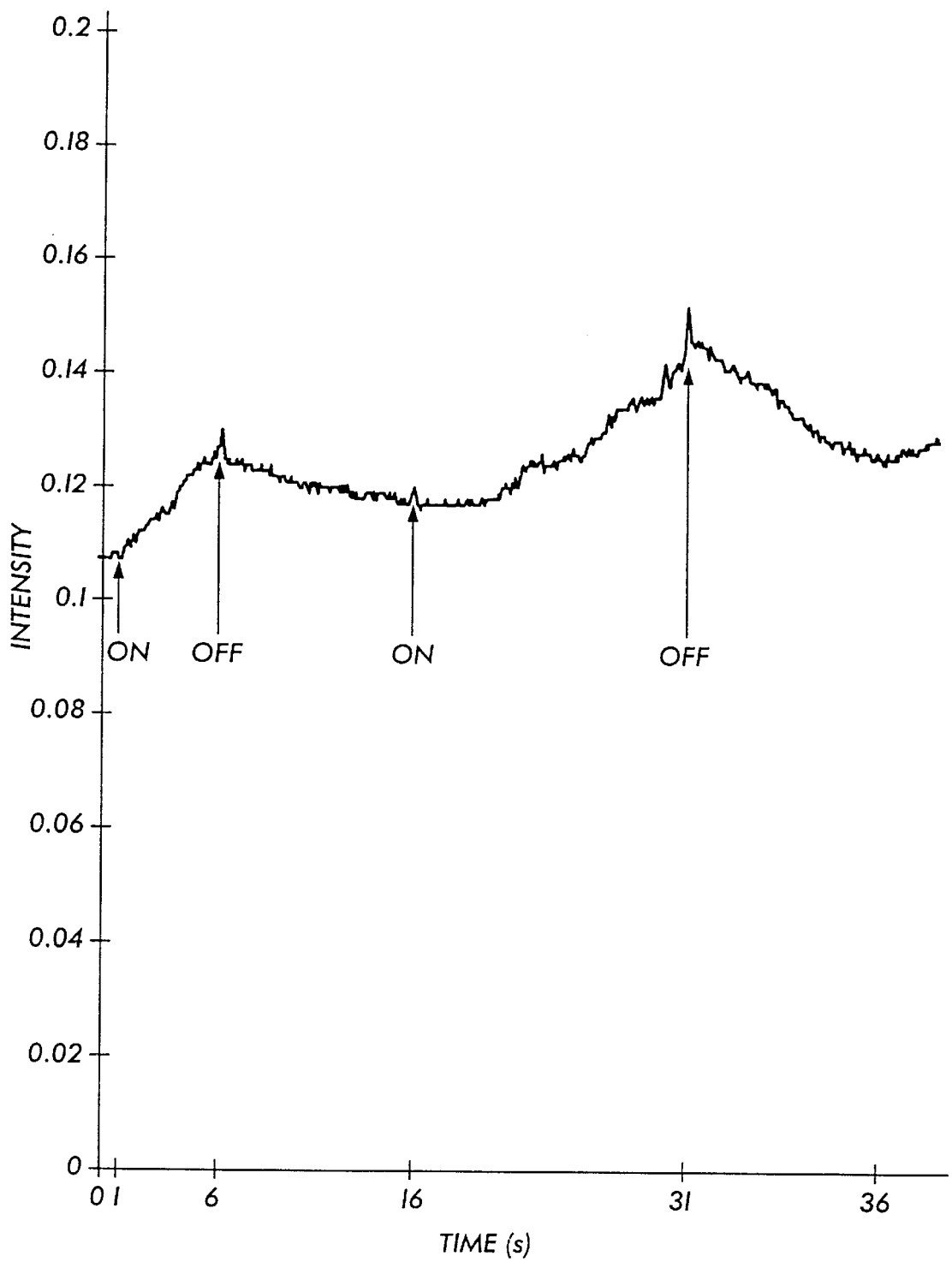

FIGS. 8B and 8C show the fluorescent spectra of one base pair mismatched DNA (SEQ ID NO: 2 and SEQ ID NO:3, respectively). After hybridizing at 25° C. for 1 hour, the fluorescent spectra of mutant DNA showed a difference from the spectrum of wild type DNA. When voltage was applied, the intensity quickly increased, and when voltage was removed, the intensity decreased.

EXAMPLE 7

This Example was similar to Example 1 except for the following details. A 375 bp fragment of p53 wild type DNA (SEQ ID NO:7), a corresponding 375 bp mutant type DNA fragment (SEQ ID NO:8), a corresponding 375 bp mutant type DNA fragment (SEQ ID NO:9) and a 633 bp DNA fragment (SEQ ID NO:10) were obtained by PCR. The 375 bp wild type DNA contained a target sequence of DNA complementary to the 12 base PNA from Example 1. The 633 bp DNA lacked such a target sequence and was used as a negative control in this example. SEQ ID NO:8 was identical to the wild type fragment (SEQ ID NO:7) except for a point mutation at amino acid position 344 at which the DNA wild type sequence CTG was changed to CAG. SEQ ID NO:9 was identical to the wild type fragment (SEQ ID NO:7) except for a point mutation at amino acid position 344 at which the DNA wild type sequence CTG was changed to CGG.

Each sample comprised 50 pmol of the respective DNA fragment, 200 pmol of PNA probe and 130 ml of buffer (0.5×TBE at pH 6.5). Each sample was heated at 95° C. for about 30 minutes. Each sample was then allowed to hybridize for 1 hour under ambient conditions (25° C.). Before fluorescence measurement, unbound probe was filtered from solution using a G50 column.

Figure 9A:
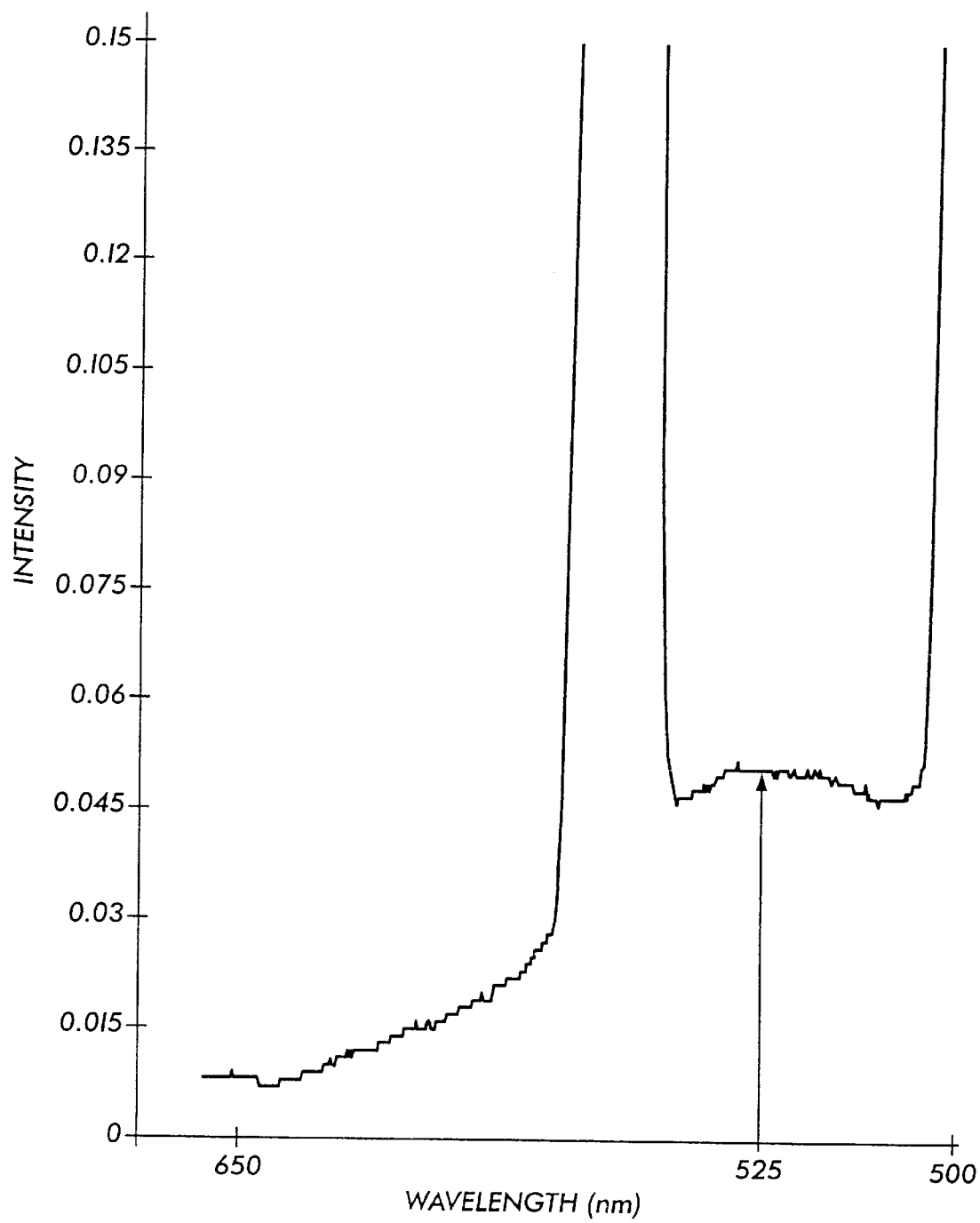
Figure 9B:
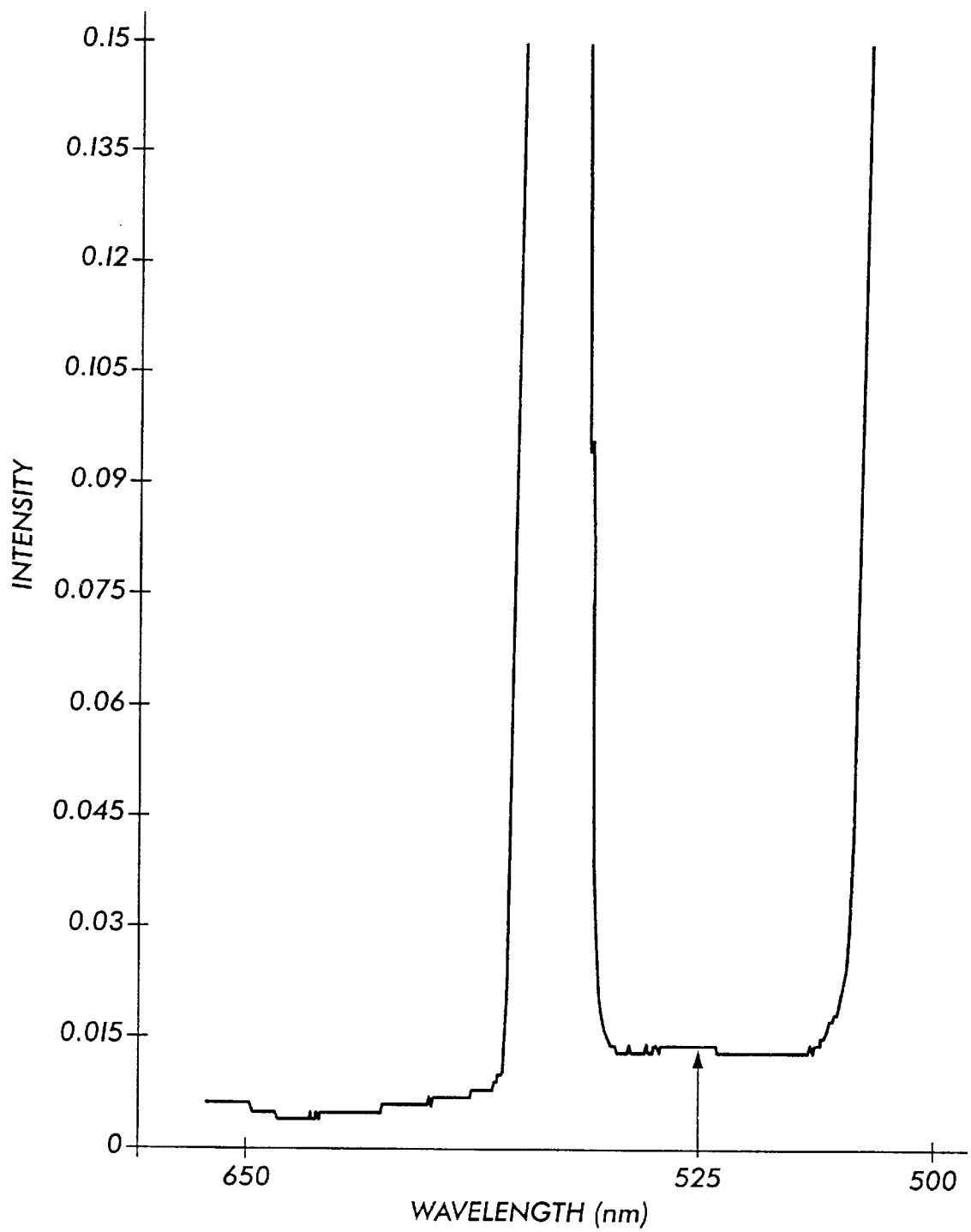
Figure 9C:
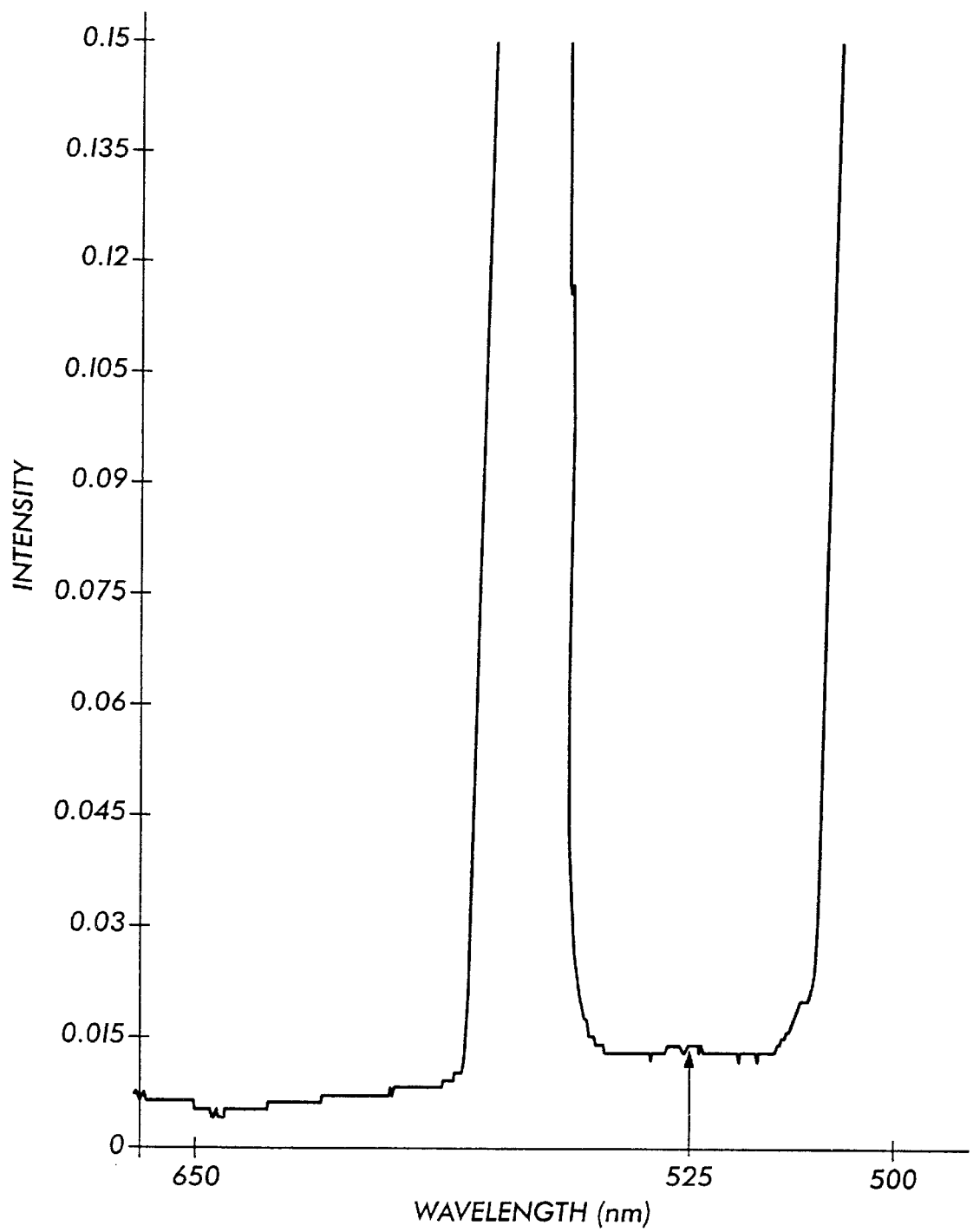

Each sample was placed in a fluorescence spectrometer for detection of the fluorescent probe attached to the target genomic DNA. As with the previous examples, the relative fluorescence intensity at 525 nm was highest for samples containing DNA fragments completely complementary to the probe, thus allowing the samples containing mutant DNA fragments (FIGS. 9B–9C) to be distinguished from the sample containing wild type DNA fragments (FIG. 9A). As expected, the negative control DNA fragment showed the lowest fluorescent intensity of all (FIG. 9D).

EXAMPLE 8

A clinical sample is obtained from an individual suspected of suffering from a disease which is known to be caused by a single nucleotide mutation within a known segment of the human genome. A fragment of this gene segment is amplified by PCR using a primer capable of amplifying the fragment regardless of whether it contains wild type DNA or mutant type DNA.

A PNA probe of 12 bases is provided which is complementary to a portion of the mutant type DNA fragment containing the mutant nucleotide, wherein the mutant nucleotide has a base complementary to a centrally located base of the probe. The probe is marked with fluorescein at its 5' end.

50 pmol of the DNA obtained from PCR and 300 pmol of PNA probe are added to 100 ml of buffer solution. The sample is heated at 95° C. for 30 minutes. The sample is then added to buffer preheated to 30° C. and allowed to hybridize for 1 hour.

The components of the sample are separated by G50 spin columns by spinning at 600 rpm for 2 minutes. The unhybridized PNA is filtered with a column, and the liquid medium containing hybrids and DNA passes through the column and is collected in a cuvette.

The cuvette is placed in a fluorescence spectrometer for detection of the fluorescent probe attached to the DNA. If the sample's fluorescent intensity at 525 nm exceeds a predetermined intensity value, then the mutant type DNA has been detected in the individual. If the sample's fluorescent intensity at 525 nm does not exceed a predetermined intensity value, then the mutant type DNA has not been detected in the individual. The predetermined intensity value is previously determined by calibrating the spectrometer using negative and positive control samples.

EXAMPLE 9

This Example is similar to Example 8, except for the following details. Two unlabeled DNA (one is wild type (SEQ ID NO:1), another is mutated type (SEQ ID NO:3)) need to be identified. A probe, which is complementary to the mutated DNA (SEQ ID NO:3), with the following sequence 5' CAT TCC GCT CTC (synthesized by PerSeptive Biosystems) was used to identify the two unknown DNA.

Each sample comprising 100 pmol probe, 25 pmol DNA (WT DNA or mutated DNA) and 115 μl buffer (0.5×TBE, pH 6.5) was heated at 95° C. for 30 minutes. Each sample was then allowed to hybridize for 1 hour at 25° C. Before fluorescent measurement, each sample was transferred into a G50 column and centrifuged at 750 rpm for 2 minutes. The hybrid flowed through the column and was collected in a cuvette, while the unhybridized probe was filtered and retained in the column. The cuvette was placed into a fluorescent spectrometer for fluorescence measurement.

Figure 10A:
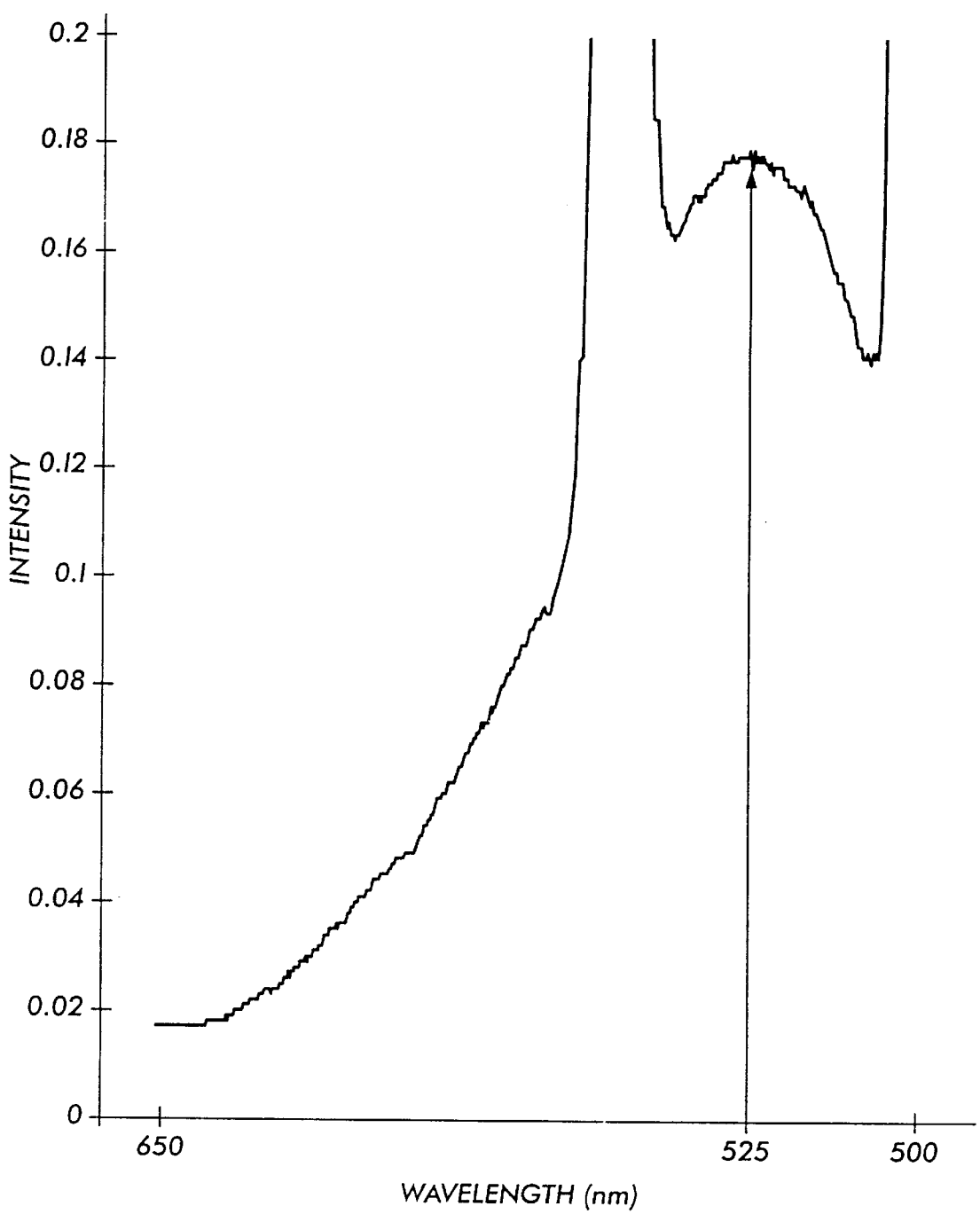
Figure 10B:
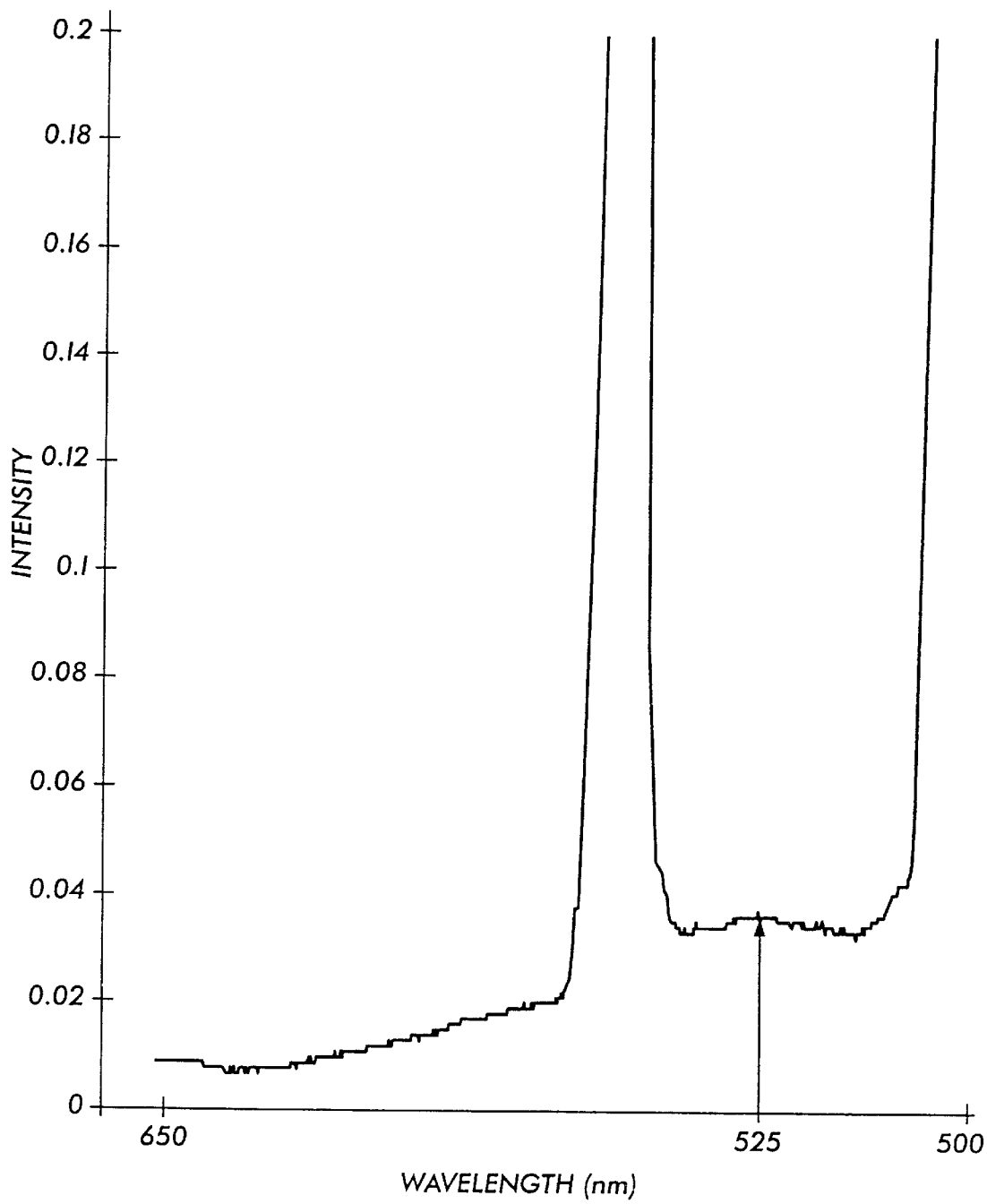

As shown in FIGS. 10A and 10B, the relative fluorescent intensity at 525 nm shows a large difference in spectra. The sample with a stronger fluorescent signal (FIG. 10A) is identified as the mutant DNA (SEQ ID NO:3). The other sample with weaker fluorescent intensity is wild type DNA (SEQ ID NO:1).

EXAMPLE 10

This Example is similar to Example 8 except for the following details. Rather than using a single probe as in Example 8, two probes are used in this example. The first probe is the probe of Example 8, which is completely complementary to a portion of the mutant type DNA fragment. The second probe is identical to the first probe, except that it has the wild type nucleobase sequence instead of the mutant type nucleobase sequence. A first portion of the sample is probed in accordance with Example 8 using the first probe. A second portion equivalent in size to the first portion is similarly probed using the second probe. After denaturation, hybridization and separation, the fluorescence of each portion is measured. If the fluorescent intensity of the first portion exceeds that of the second portion, then the mutant type DNA has been detected in the individual. If the fluorescent intensity of the second portion exceeds that of the first portion, then the mutant type DNA has not been detected in the individual.

The method of this example could be adapted for use with a diagnostic device comprising a solid support having the two contrasting type of PNA probes bonded to different areas of the support. The sample is not divided, but rather is uniformly dispersed onto the support so as to contact both probe types equally. The fluorescent intensity of the two areas of the device could be compared in the same way that the two separate samples are in Example 9.

EXAMPLE 11

Biotinylated double stranded DNA (SEQ ID NO:1 and SEQ ID NO:3) was amplified by PCR. Single stranded DNA was prepared using Dynabeads (from DYNAL company) as follows. 25 μl of 2× binding and washing buffer (from M-280 streptativin kit) and 25 μl (25 pmol) of biotinylated DNA (SEQ NO:1 and NO:2) were added into 2 mg of the prewashed dynabeads of M-280 streptativin. The mixture was incubated at room temperature for 15 minutes, keeping the beads suspended. The mixture was then placed onto a magnetic particle concentrator (MPC, Dynal, Inc.) at room temperature for 2 minutes, followed by removal of the supernatant with a pipette. 20 μl of freshly made 0.1N NaOH was added and the mixture was kept at room temperature for 5 minutes. The dynabeads were collected with the immobilized biotinylated strand on the side of the tube by using the MPC, and the NaOH supernatant was transferred with the non-biotinylated single stranded DNA to a clean tube. The NaOH supernatant was neutralized with 2.5 μl of freshly made 0.2N HCl.

Figure 11B:
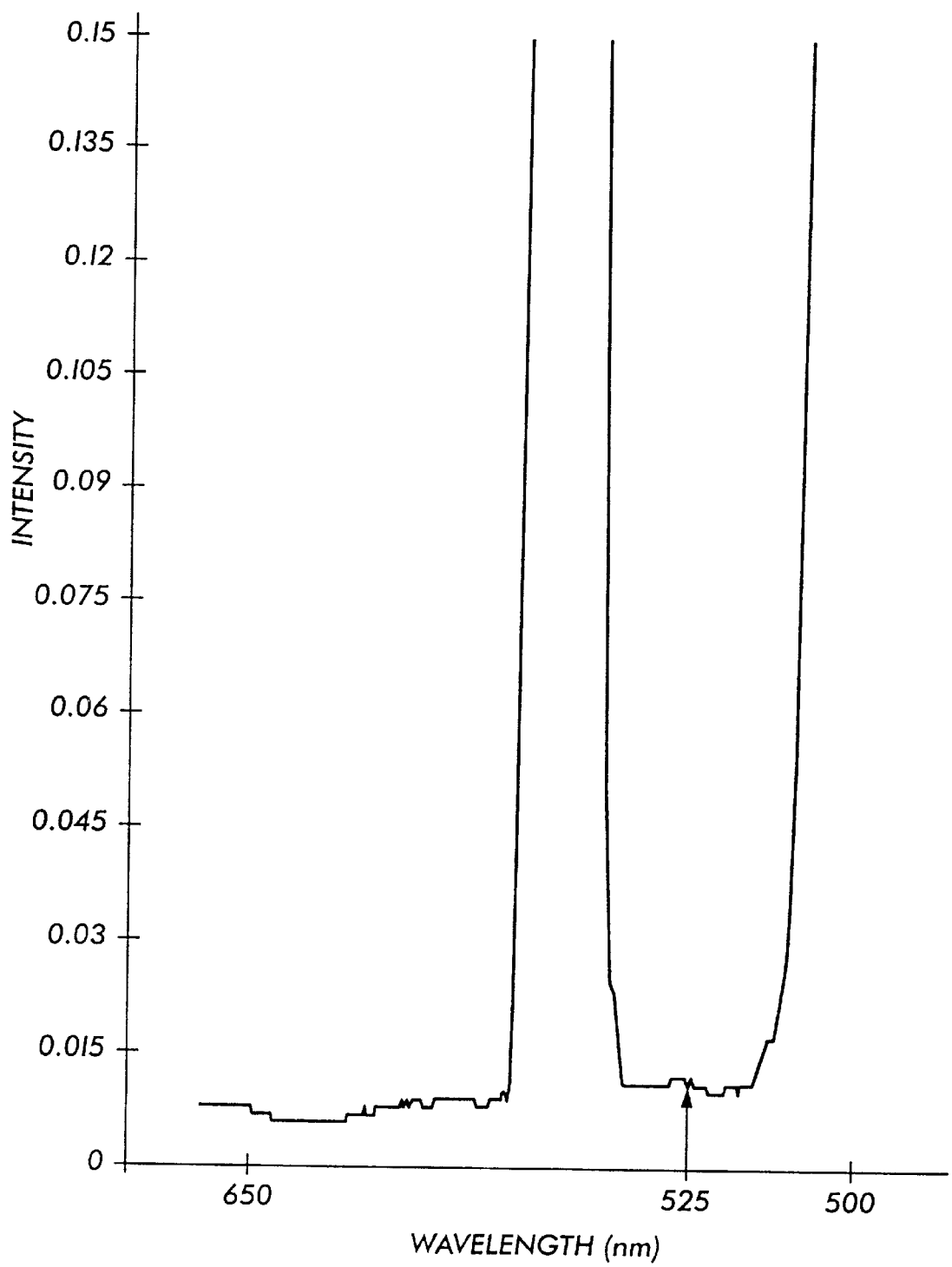

200 pmol of probe and 150 μl of 0.5×TBE buffer were added into the supernatant containing a single stranded DNA. The mixture was heated at 94° C. for 5 minutes and then incubated at room temperature for 1 hour. After separation by G50 column at 650 rpm for 2 minutes, the unbound PNA was filtered in the column and the hybrid passed through the column and collected in a cuvette. The sample was placed in a fluorescent spectrometer for fluorescence detection. As shown in FIGS. 11A and 11B, the relative fluorescent intensity at 525 nm of single stranded wild type DNA sample (FIG. 11A) was five times higher than that of mutant single stranded DNA (FIG. 11B).

EXAMPLE 12

Each sample comprising 400 pmol probe, 100 pmol DNA (SEQ ID NO.:1) and 100 μl buffer (0.5×TBE, pH 6.5) was heated at 95° C. for 30 minutes. Each sample was then allowed to hybridize for 1 hour at 25° C. Before fluorescent measurement, each sample was transferred into a G50 column and centrifuged at 720 rpm for 2 minutes. The hybrids flowed through the column and were collected in a cuvette, while the unhybridized probe was filtered and retained in the column. The cuvette was placed into a fluorescent spectrometer for fluorescence measurement.

Figure 12A:
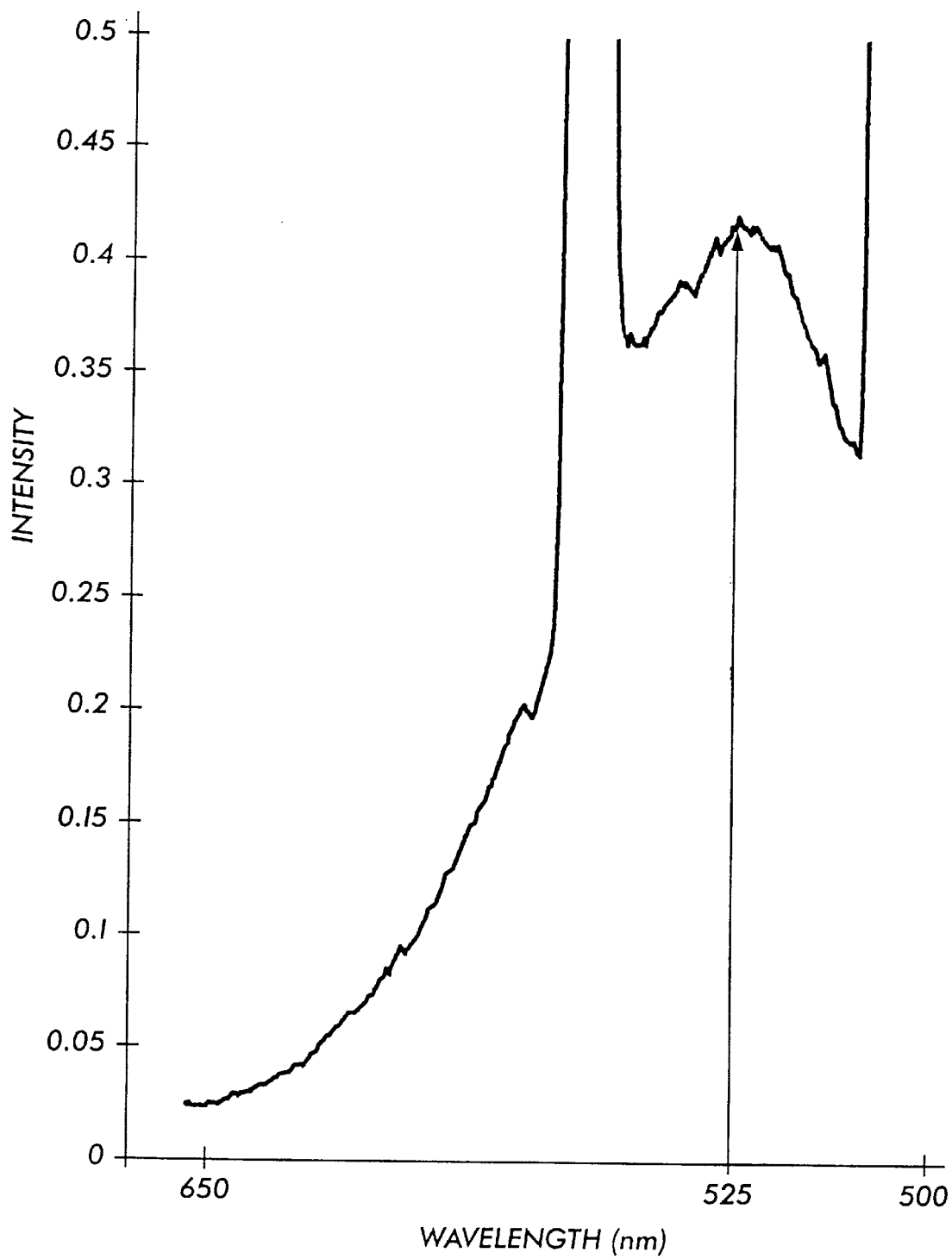
Figure 12B:
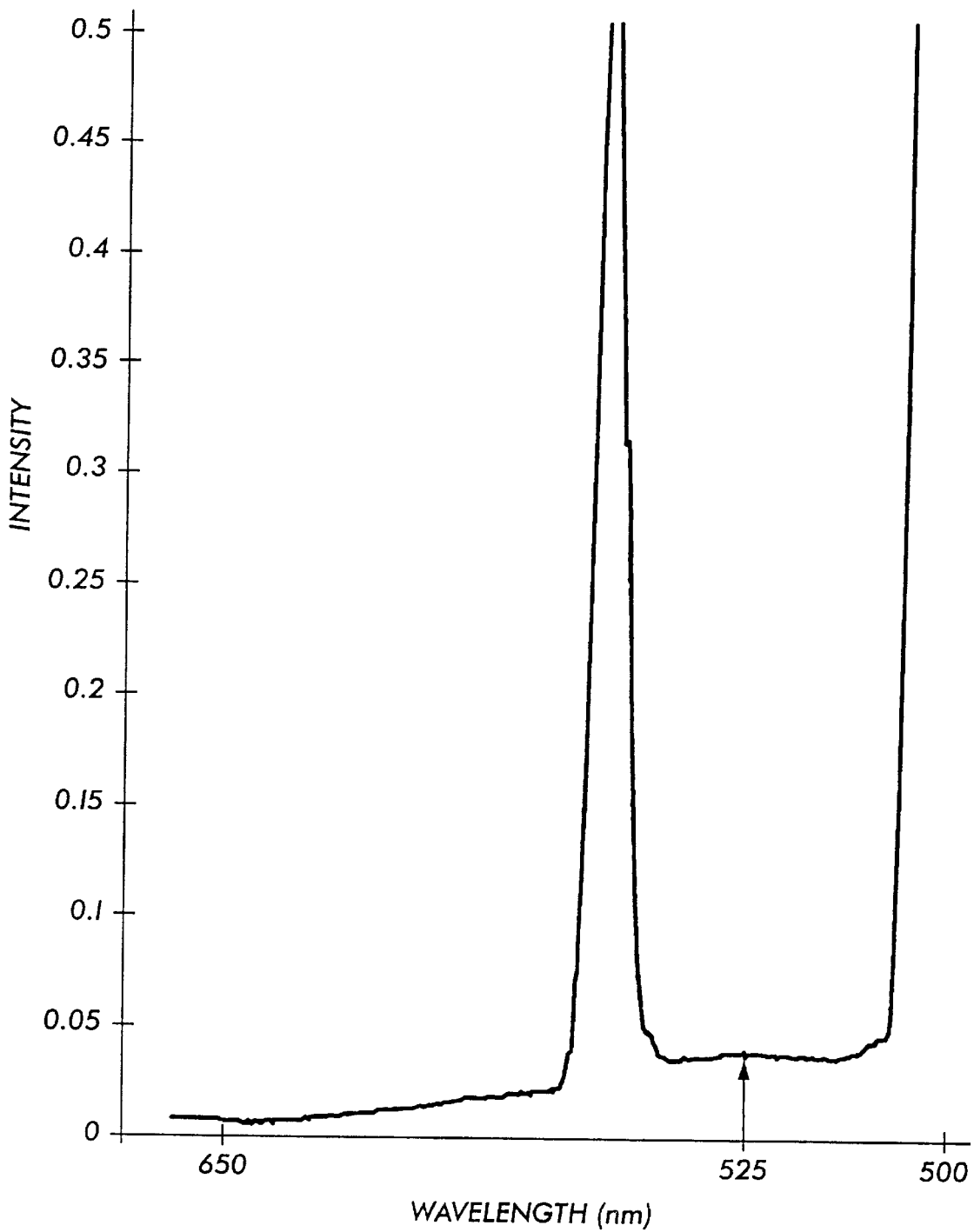

As shown in FIGS. 12A and 12B, the relative fluorescence intensity at 525 nm shows a large difference in the spectra. The spectrum with a stronger fluorescent signal (FIG. 12A) shows a perfect matched probe hybridization with WT DNA (SEQ ID NO:1). The other spectrum with weaker fluorescent intensity (FIG. 12B) shows a one bp mismatched probe hybridization with WT DNA (SEQ ID NO:1).

EXAMPLE 13

Two PNA probes having the same dye (fluorescein) hybridized with two perfectly matched targets in different strands.

Example 13a

One probe perfectly matching one target sequence.

A 150 bp fragment of genomic DNA from mutated type p53 DNA (SEQ ID NO:11) was amplified by PCR and purified using the QIAquick PCR Purification Kit (QIAGEN Inc., Chatsworth, Calif., USA). The mutated fragment was identical to the wild type fragment (SEQ ID NO:1) except for a two base mutation at amino acid position 340 (i.e., bases 88–90) at which the DNA wild type sequence ATG was changed to GAG.

A 12-mer PNA probe (Probe No. 1) was synthesized by PerSeptive Biosystems, Inc. of Framingham, Mass., USA. The probe, having the structure:

5' H-Fluo-O-CAT TCA GCT CTC Lys-CONH$_2$, was designed to be complementary to a 12 nucleotide segment of the 150 bp p53 ME DNA, starting at base pair position 95 and ending at base pair position 106 (see SEQ ID NO:11).

0.5×TBE solution (0.0225 M Tris-borate/0.0005 M EDTA, pH 6.5) was used as hybridization buffer. 5 pmol of DNA (SEQ ID NO:11) was added into 115 μl 0.5×TBE buffer. Then 2.5 pmol of Probe No. 1 was added into the solution. The sample was heated at 95° C. for 10 minutes and hybridized at 25° C. for 30 minutes.

Before fluorescence measurement, the unbound probe was filtered from the solution by G50 spin column (purchased from Pharmacia Biotech, AB, Uppsala, Sweden). The solution with the hybrids of PNA-DNA was placed into a cuvette and subjected to fluorescence measurement.

Figure 13A:
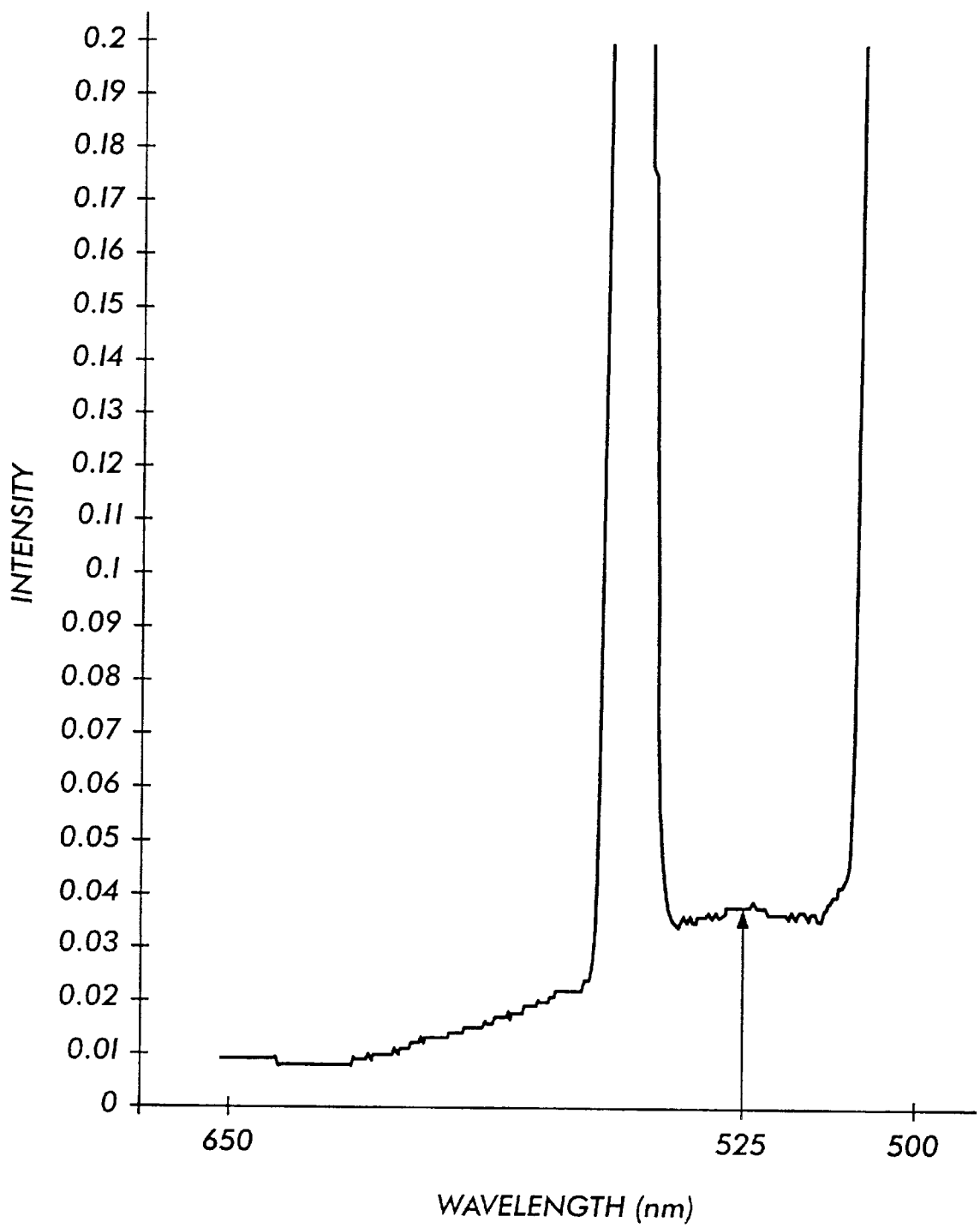

FIG. 13A shows the fluorescence spectrum of 5 pmol of DNA (SEQ ID NO:11) hybridized with 2.5 pmol of Probe No.1. A peak appears at 525 nm.

Example 13b

One probe perfectly matching one target sequence.

A 12-mer PNA probe (Probe No. 2) synthesized by PerSeptive Biosystems, Inc., having the structure:

5' H-Fluo-O-TCG AGG AGT TCC Lys-CONH$_2$, was prepared to be completely complementary to a target in the strand of ME DNA complementary to the strand targeted in Example 13a, starting at base pair position 83 and ending at base pair position 94 (see SEQ ID NO:11).

5 pmol of DNA (SEQ ID NO:11) was added into 115 μl 0.5×TBE buffer. Then the probe was added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 13B:
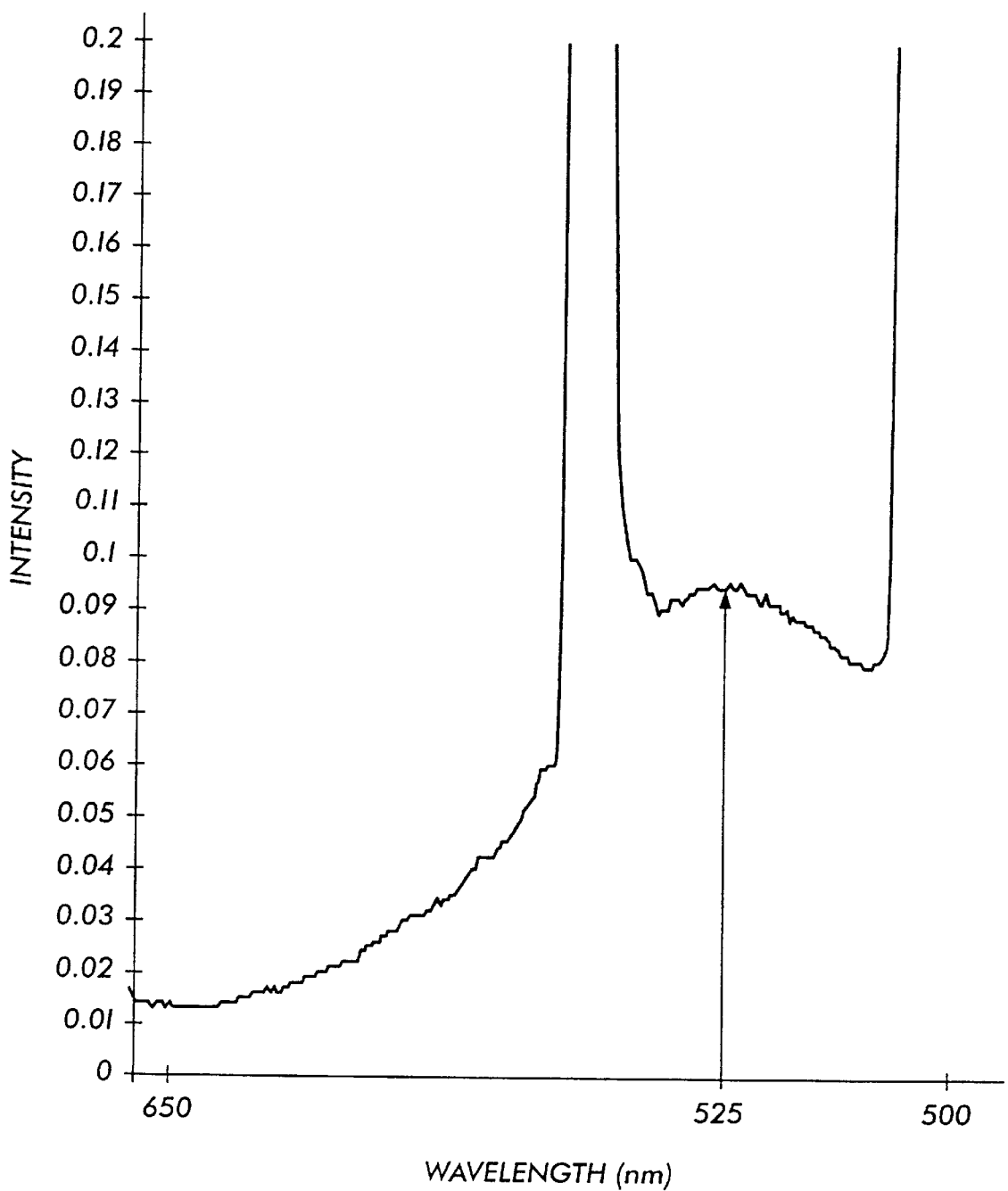

FIG. 13B shows the fluorescence spectrum of 5 pmol of DNA (SEQ ID NO:11) hybridized with 5 pmol of Probe No. 2.

Example 13c

Two probes perfectly matching two target sequences in different strands.

5 pmol of DNA (SEQ ID NO:11) was added into 115 μl 0.5×TBE buffer. Then 2.5 pmol of Probe No. 1 and 5 pmol of Probe No. 2 were added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 13C:
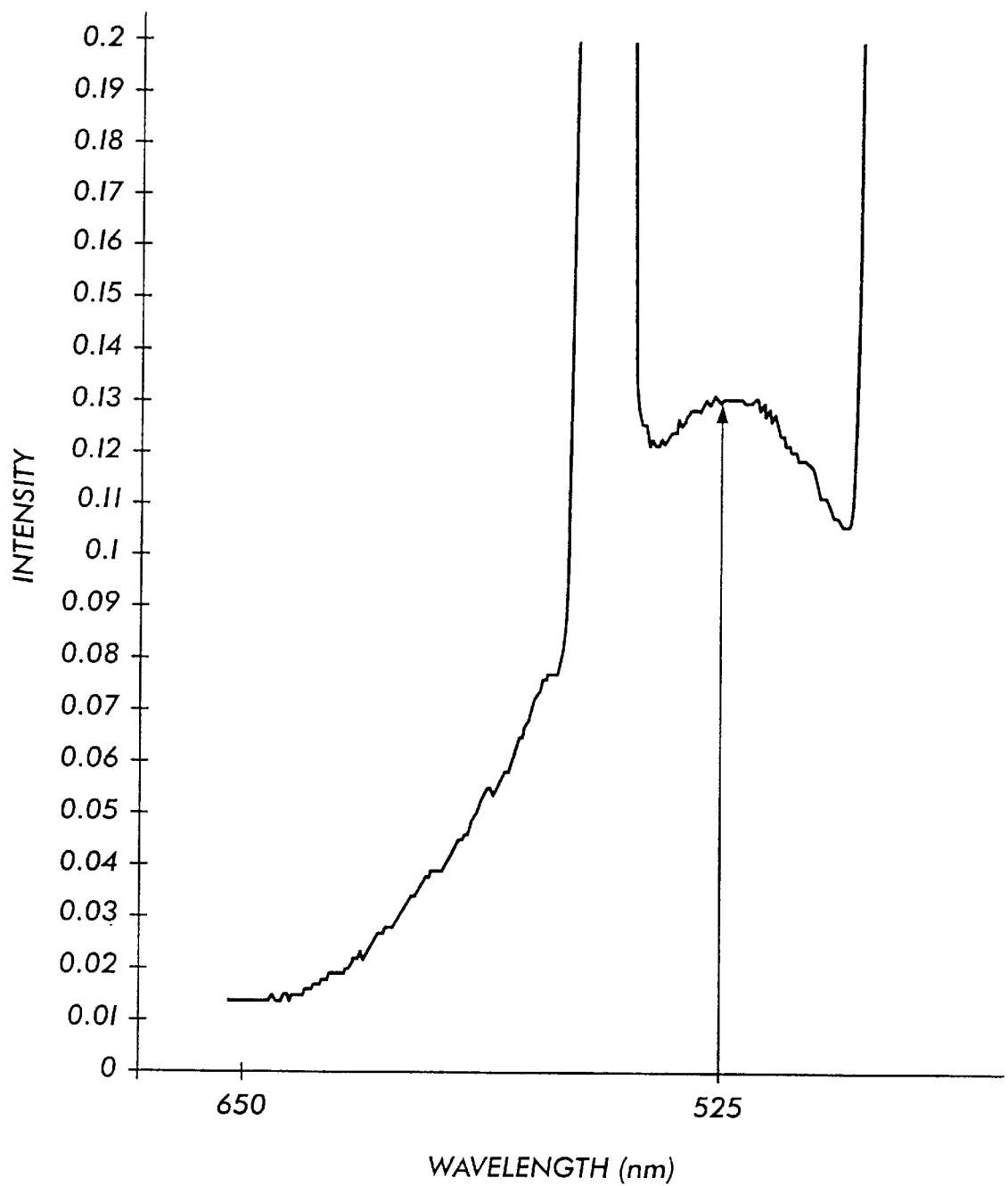

FIG. 13C shows the fluorescence spectrum of 5 pmol of DNA (SEQ ID NO:11) hybridized with 2.5 pmol of Probe No. 1 and 5 pmol of Probe No. 2. As shown in FIG. 13C, the fluorescent intensity at 525 nm is approximately about the sum of the intensities at 525 nm shown in FIGS. 13A and 13B.

EXAMPLE 14

Two PNA probes having different dyes (fluorescein and rhodamine) hybridized with one perfectly matched target.

Example 14a

A 150 bp fragment of genomic DNA from wild type p53 DNA (SEQ ID NO:1) was amplified by PCR and purified by using the QIAquick PCR Purification Kit.

A 12-mer rhodamine labeled PNA probe (Probe No. 3) synthesized by PerSeptive Biosystems, Inc., having the structure:

5'H-Rho-O-CAT TCA GCT CTC Lys-CONH$_2$, was designed to be complementary to a 12 nucleotide segment of the 150 bp p53 DNA, starting at base pair position 95 and ending at base pair position 106 (see SEQ ID NOS: 1, 11, and 12).

20 pmol of DNA (SEQ ID NO:1) was added into 50 μl 0.5×TBE buffer. Then 20 pmol of the Probe No. 3 was added into the solution. The sample was heated at 95° C. for 10 minutes and hybridized at 25° C. for 30 minutes.

Before fluorescence measurement, the unbound probe was filtered from the solution by G50 spin column. The solutions with the hybrids of PNA-DNA were placed into a cuvette and subjected to fluorescence measurement.

Figure 14A:
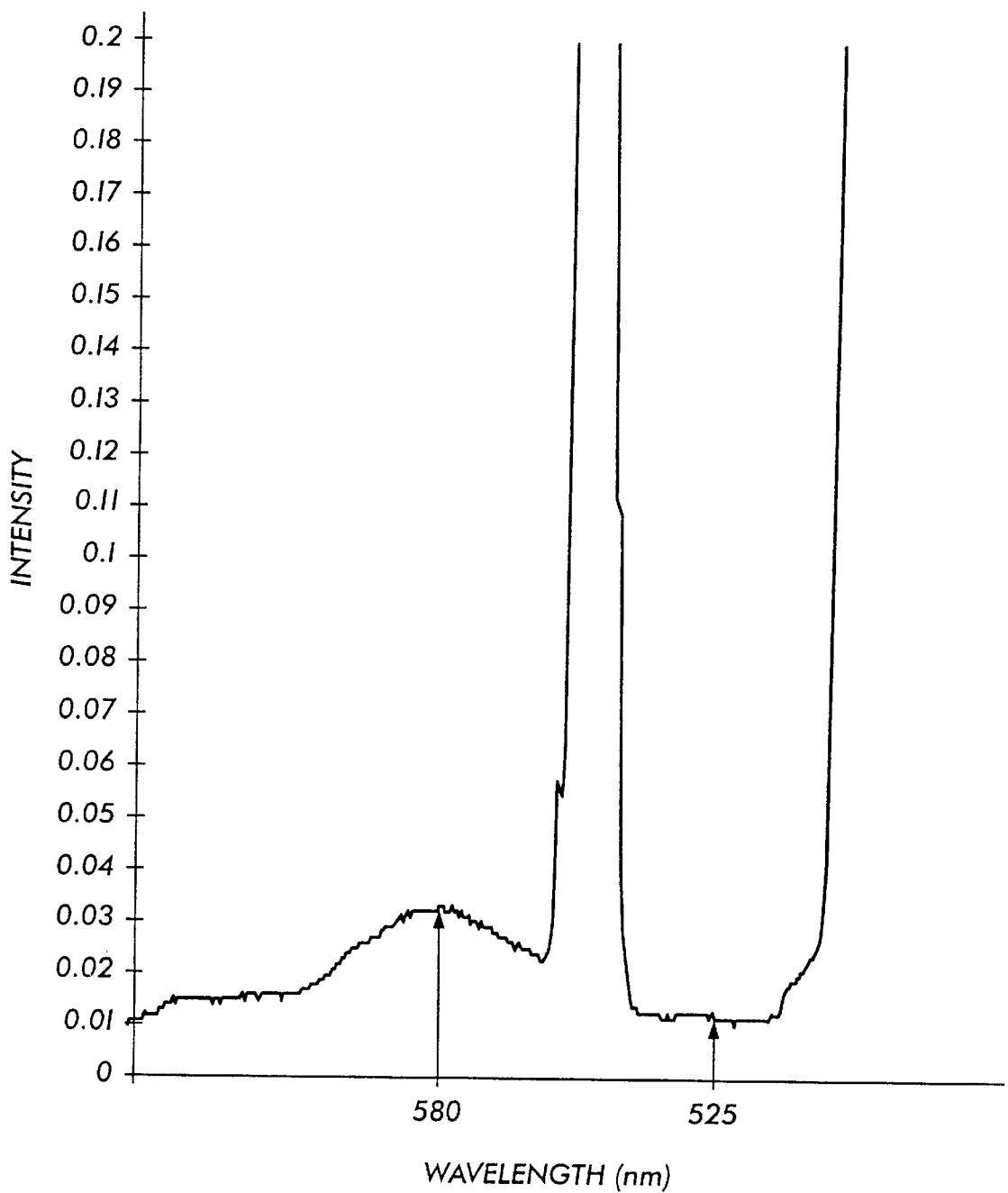

FIG. 14A shows a fluorescence spectrum of DNA hybridized with the rhodamine labeled PNA probe. The emission peak in the fluorescence spectrum emerges at about 580 nm.

Example 14b 20 pmol of DNA (SEQ ID NO:1) was added into 50 μl 0.5×TBE buffer. Then 15 pmol of rhodamine labeled probe (Probe No. 3) and 5 pmol of fluorescein labeled probe (Probe No. 1) were added into the solution. The sample was heated at 95° C. for 10 minutes and then the sample was hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 14B:
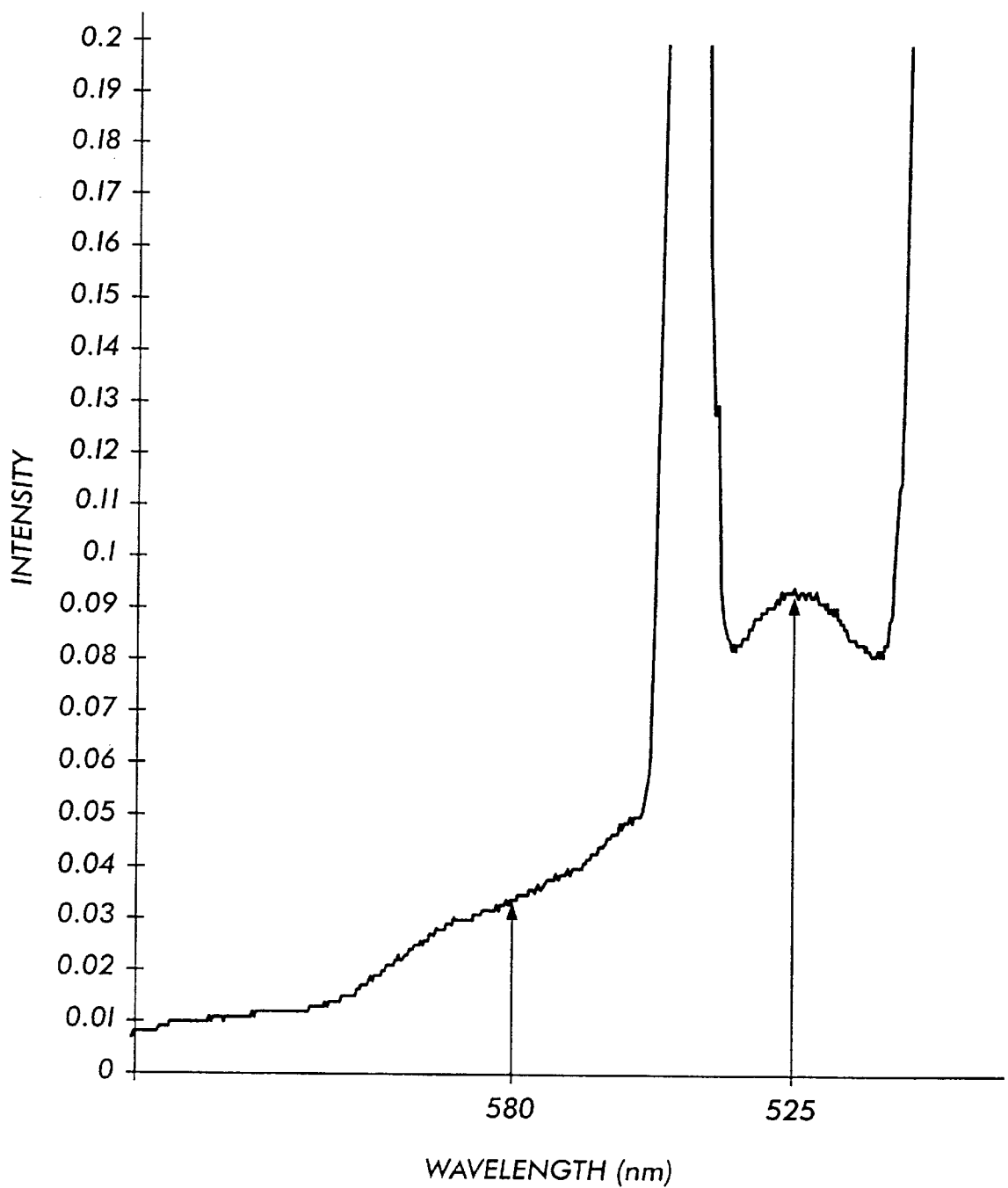

FIG. 14B shows a fluorescence spectrum of DNA hybridized with the mixed probes of rhodamine labeled PNA probe (Probe No. 3) and fluorescein labeled PNA probe(Probe No. 1). A shoulder emerged at 580 nm due at least in part to rhodamine labeled probe hybridized to the target sequence and a peak emerged at 525 nm partly contributed by the fluorescein labeled probe hybridized to the target sequence.

EXAMPLE 15

Two PNA probes having different dyes (fluorescein and rhodamine) hybridized with two perfectly matched targets on two strands.

Example 15a 20 pmol of DNA (SEQ ID NO:11) was added into 50 μl 0.5×TBE buffer. Then 20 pmol of rhodamine labeled probe (Probe No. 3) was added into the solution. The sample was heated at 95° C. for 10 minutes and then the sample was hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 15A:
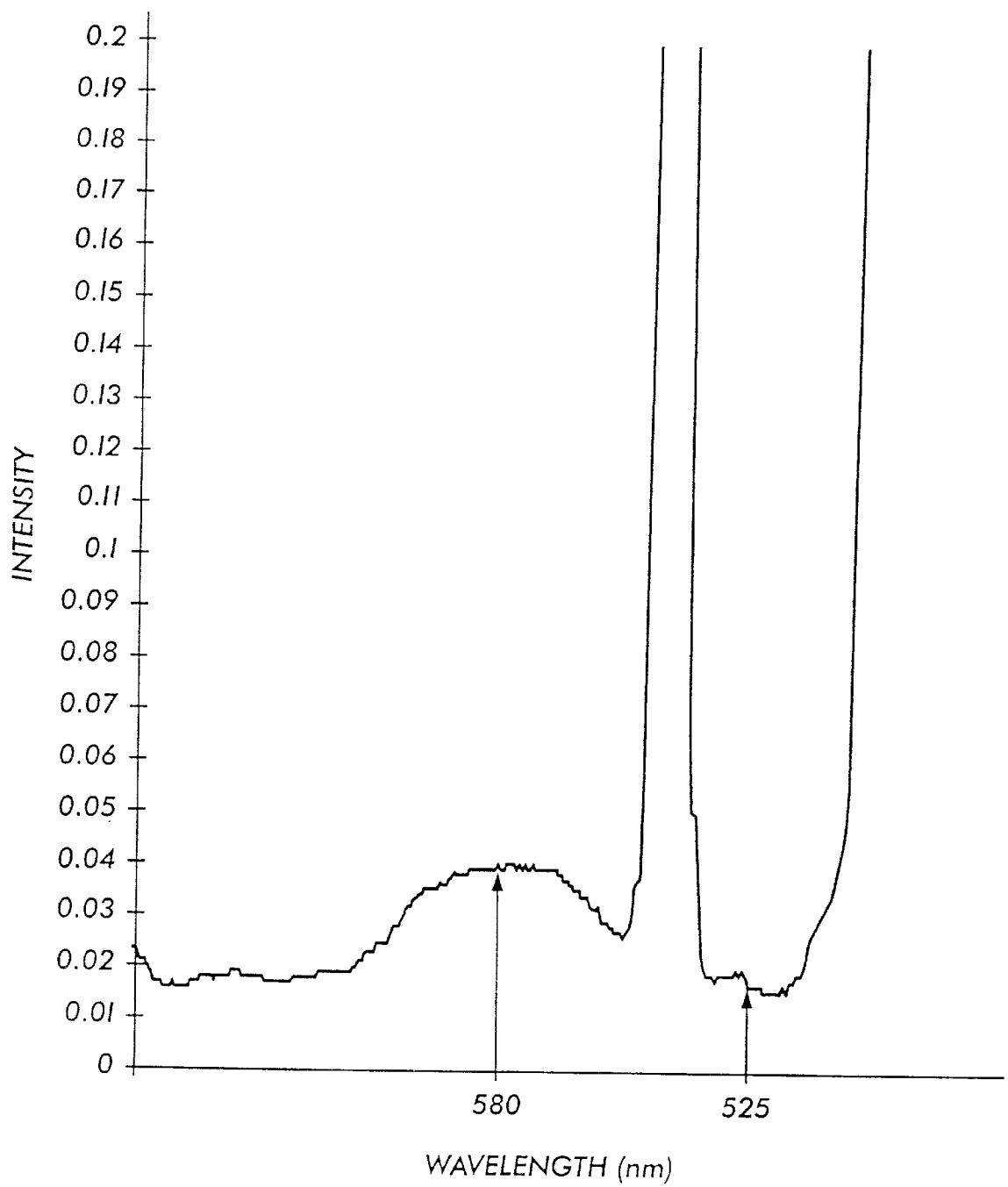

FIG. 15A shows a fluorescence spectrum of DNA hybridized with the rhodamine labeled PNA probe (Probe No. 3). A broad peak emerges at 580 nm contributed by hybridization complexes labeled with rhodamine.

Example 15b 20 pmol of DNA (SEQ ID NO:11) was added into 50 μl 0.5×TBE buffer. Then 20 pmol of rhodamine labeled probe (Probe No. 3) and 5 pmol of fluorescein labeled probe (Probe No. 2) were added into the solution. The sample was heated at 95° C. for 10 minutes and then the sample was hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 15B:
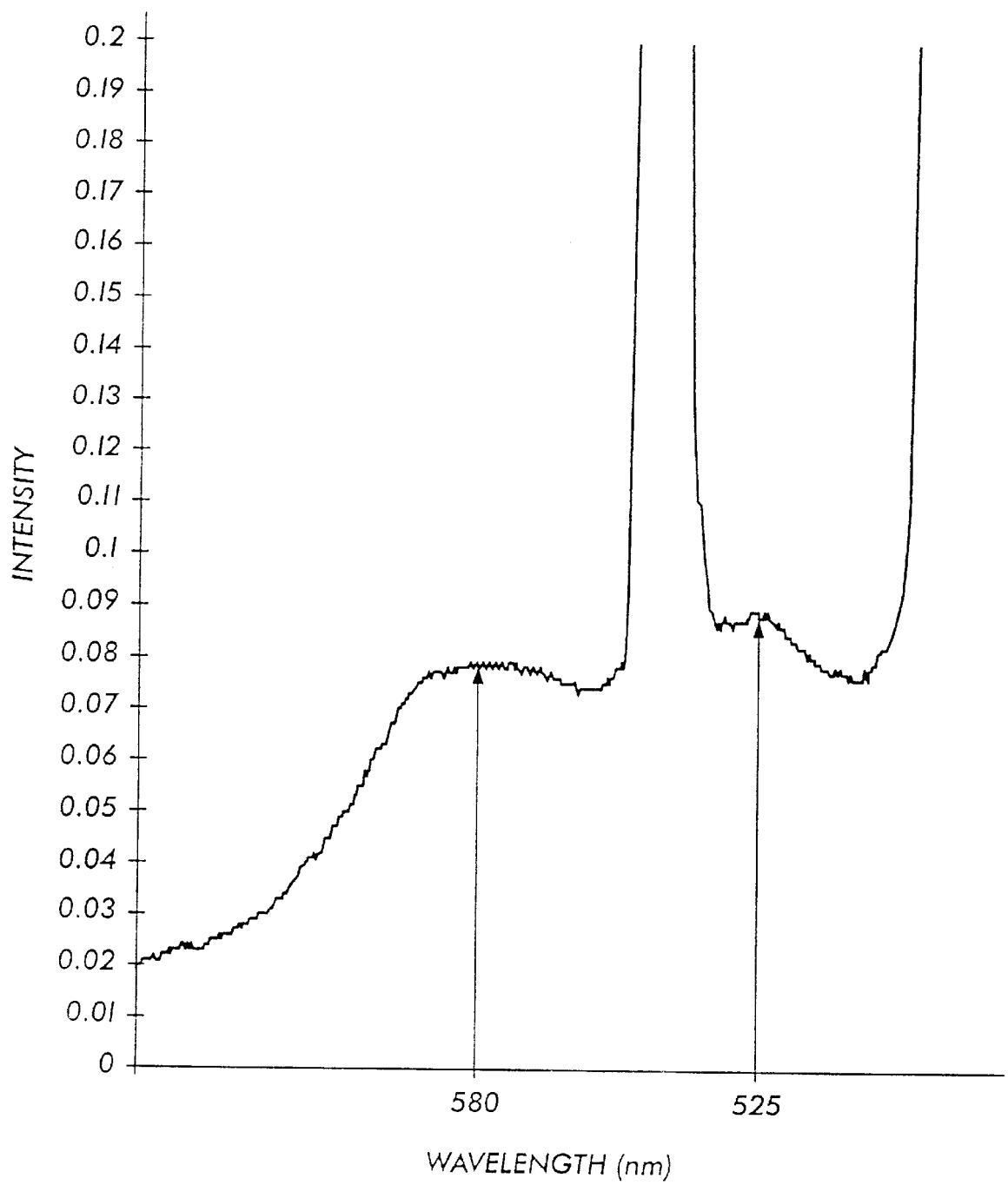

FIG. 15B shows a fluorescence spectrum of DNA hybridized with Probe Nos. 2 and 3. A broad peak emerges at 580 nm contributed by the rhodamine labeled probe and a peak rises at 525 nm contributed by the fluorescein labeled probe.

EXAMPLE 16

A PCR amplified and purified 633 bp DNA (SEQ ID NO:10) lacking a target sequence was used as a negative control for probes.

5 pmol DNA (SEQ ID NO:10) was added into 115 µl 0.5×TBE buffer and then Probe Nos. 1–3 were added into the solution. Each sample was heated at 95° C. for 10 minutes and then hybridized at 25° C. for 30 minutes.

Before the fluorescence measurement, the unbound probe was filtered from the solution by G50 spin column. The solution was placed into a cuvette and subjected to fluorescence measurement.

Figure 16A:
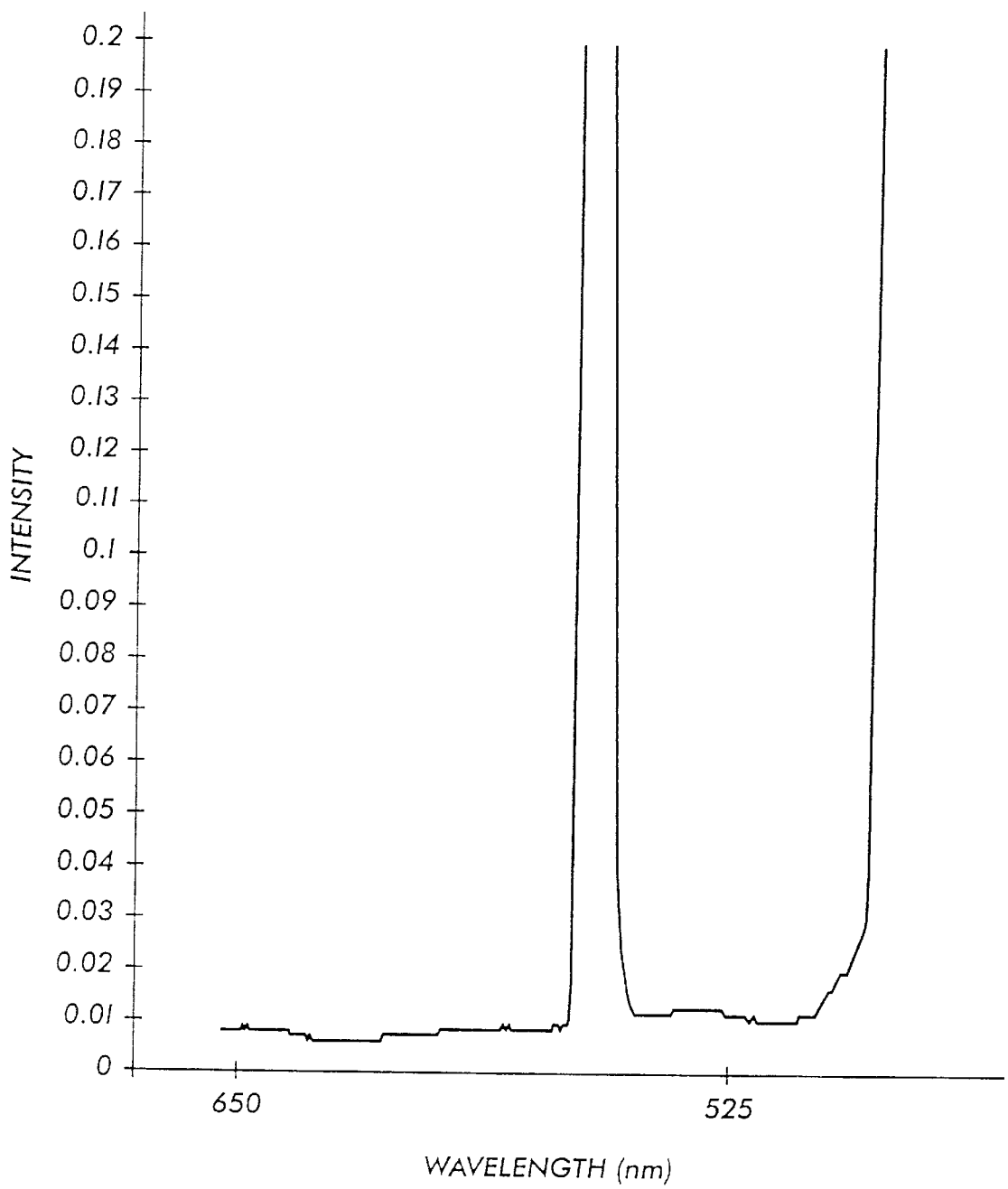

FIG. 16A shows a fluorescence spectrum of probe alone (i.e., no DNA was added to the sample, which included 15 pmol of the probes—5 pmol of each of Probe Nos. 1, 2 and 3).

Figure 16B:
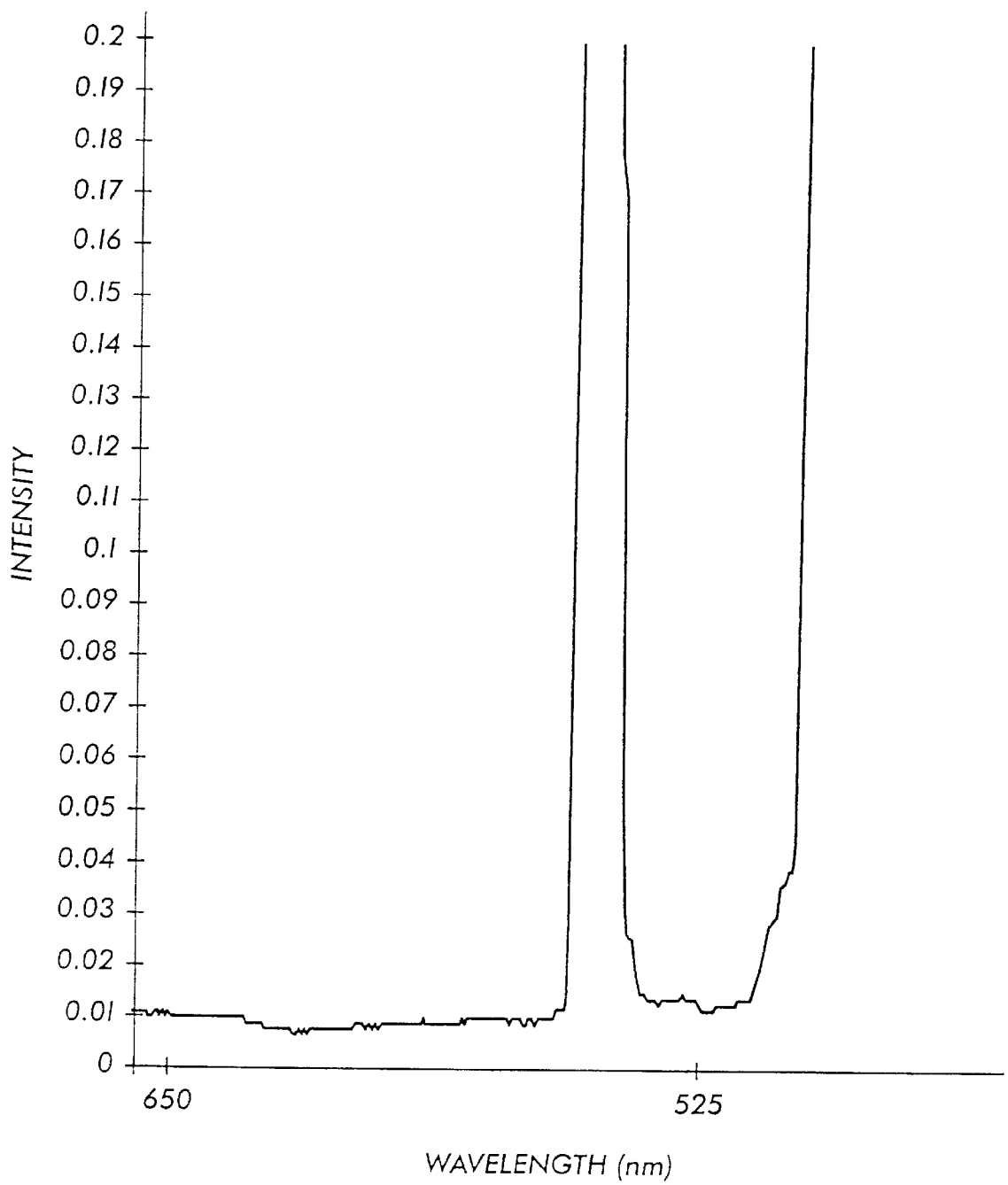

FIG. 16B shows a fluorescence spectrum of 5 pmol of Probe No. 1 and negative control DNA (SEQ ID NO:10).

Figure 16C:
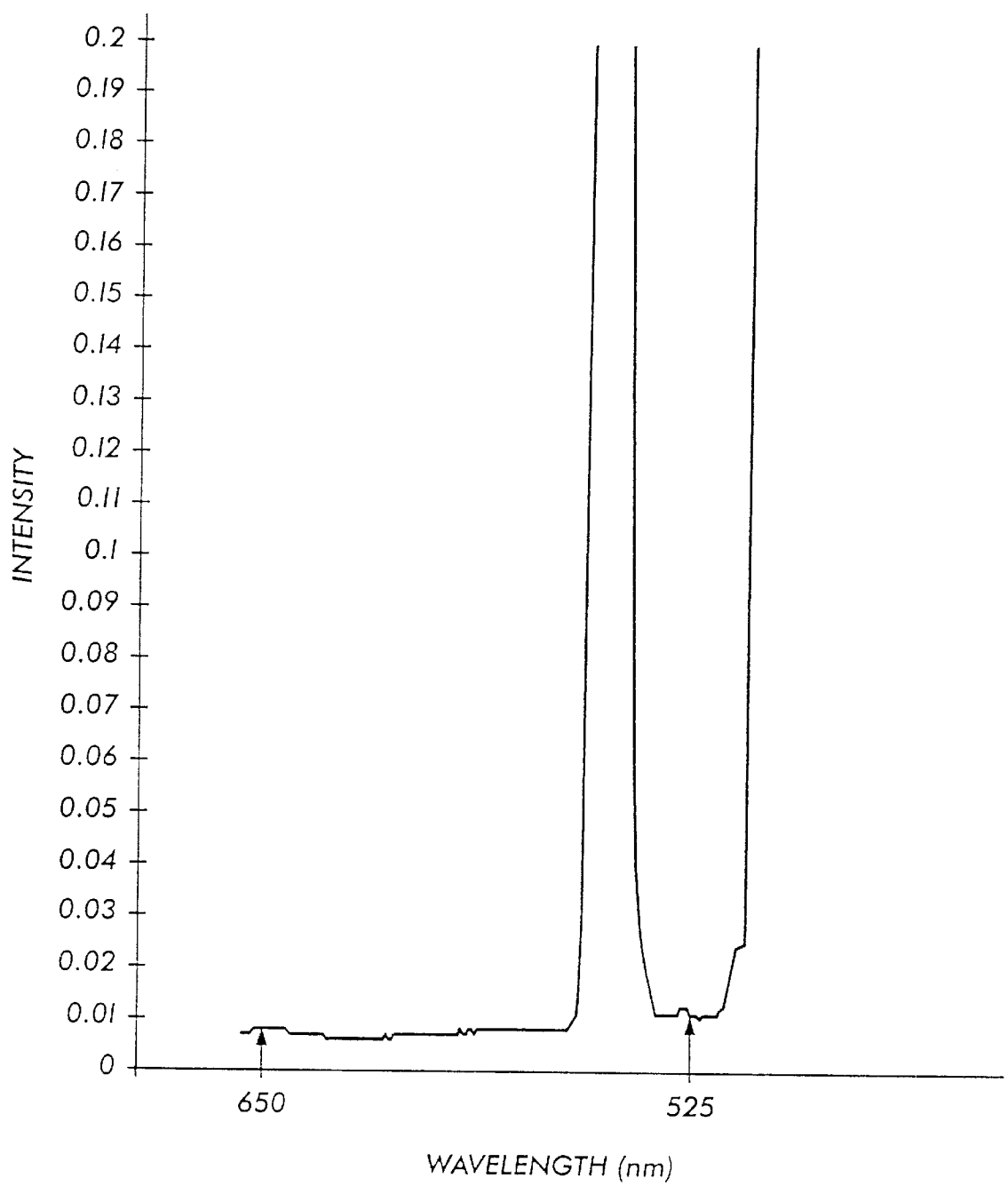

FIG. 16C shows a fluorescence spectrum of 5 pmol of Probe No. 2 and negative control DNA (SEQ ID NO:10).

Figure 16D:
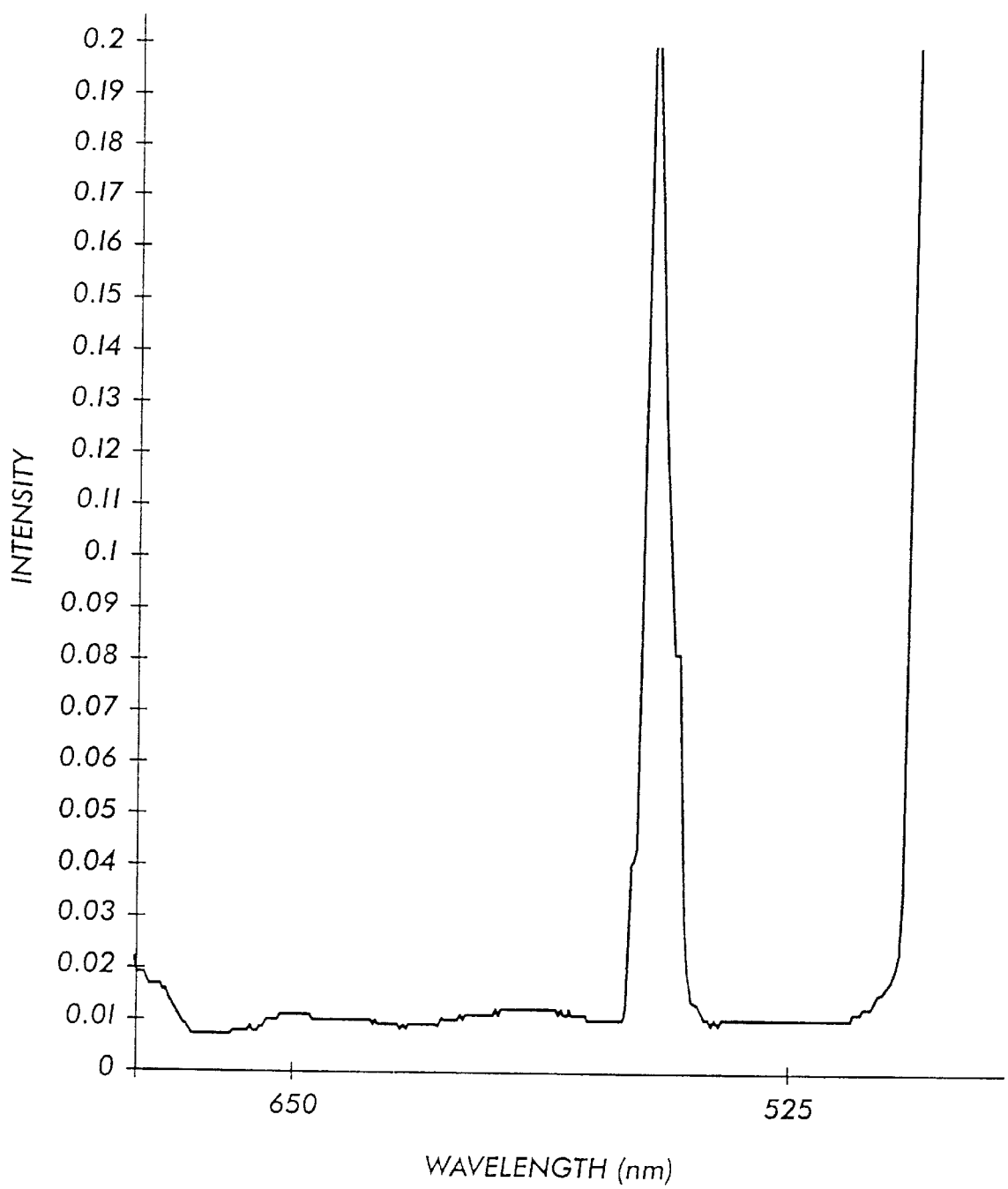

FIG. 16D shows a fluorescence spectrum of 5 pmol of Probe No. 3 and negative control DNA (SEQ ID NO:10).

All the spectra show the fluorescent intensity at background level at 525 nm and 580 nm.

EXAMPLE 17

Two PNA probes having the same dye (fluorescein) hybridized with a one base pair mismatched target sequence and a perfectly matched target sequence.

Example 17a

A 150 bp fragment of genomic DNA from p53 DNA gene MQ (SEQ ID NO:12) was amplified by PCR and purified by using the QIAquick PCR Purification Kit. The mutated fragment was identical to the ME DNA (SEQ ID NO:11) fragment except for a one base mutation at amino acid position 340 (bases 88–90) at which the DNA sequence CTC was changed to GTC.

5 pmol of DNA (SEQ ID NO:12) was added into 115 µl 0.5×TBE buffer. Then 5 pmol of Probe No. 2, which has a one base pair mismatch to the target sequence, was added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 17A:
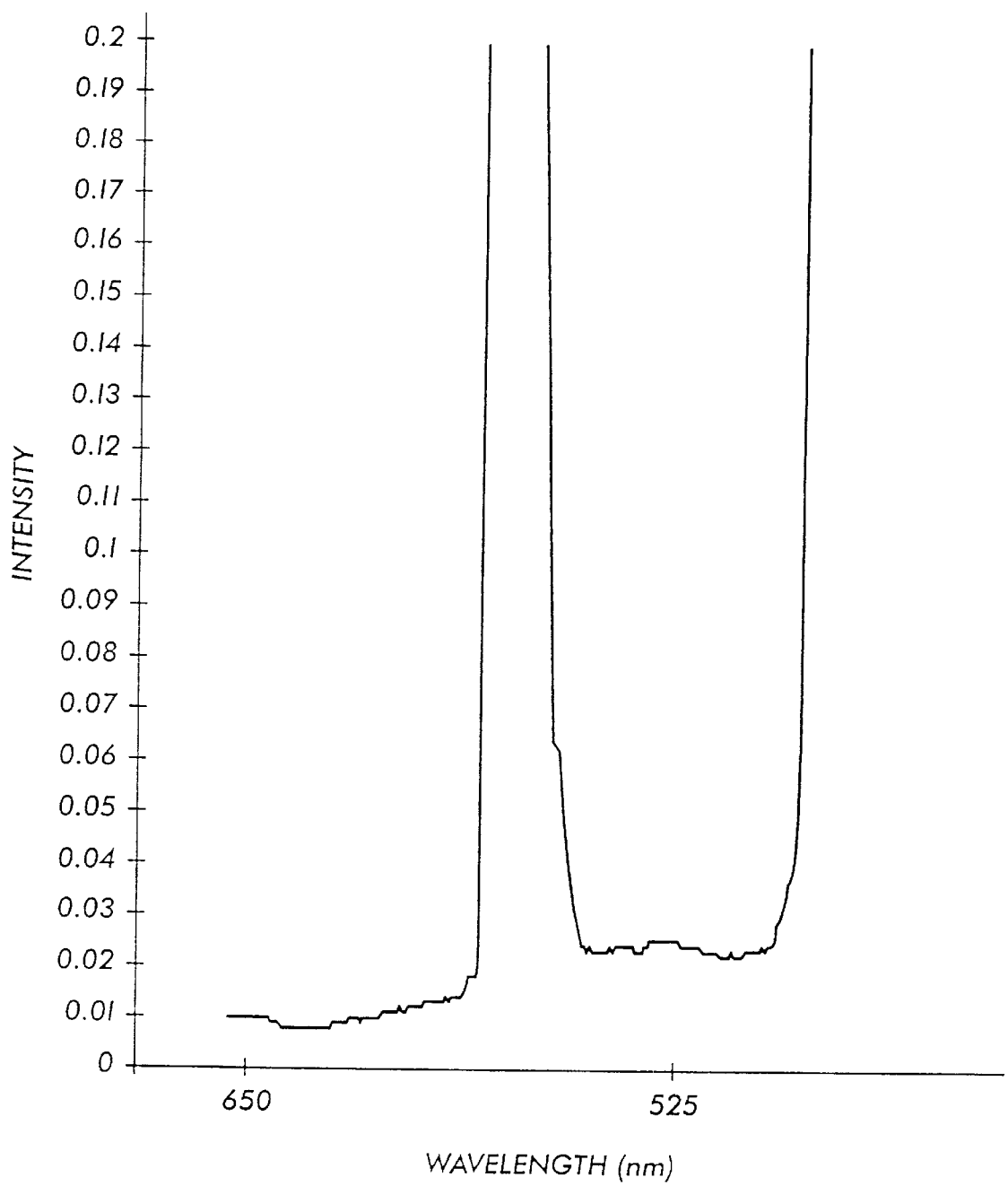

FIG. 17A shows the fluorescence spectrum of 5 pmol of DNA (SEQ ID NO: 12) hybridized with 5 pmol of Probe No. 2. The spectrum shows the fluorescent intensity at background level.

Example 17b 5 pmol of DNA (SEQ ID NO:12) was added into 115 µl 0.5×TBE buffer. Then Probe No. 1 was added into the solution. This probe was perfectly matched with the DNA target. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 17B:
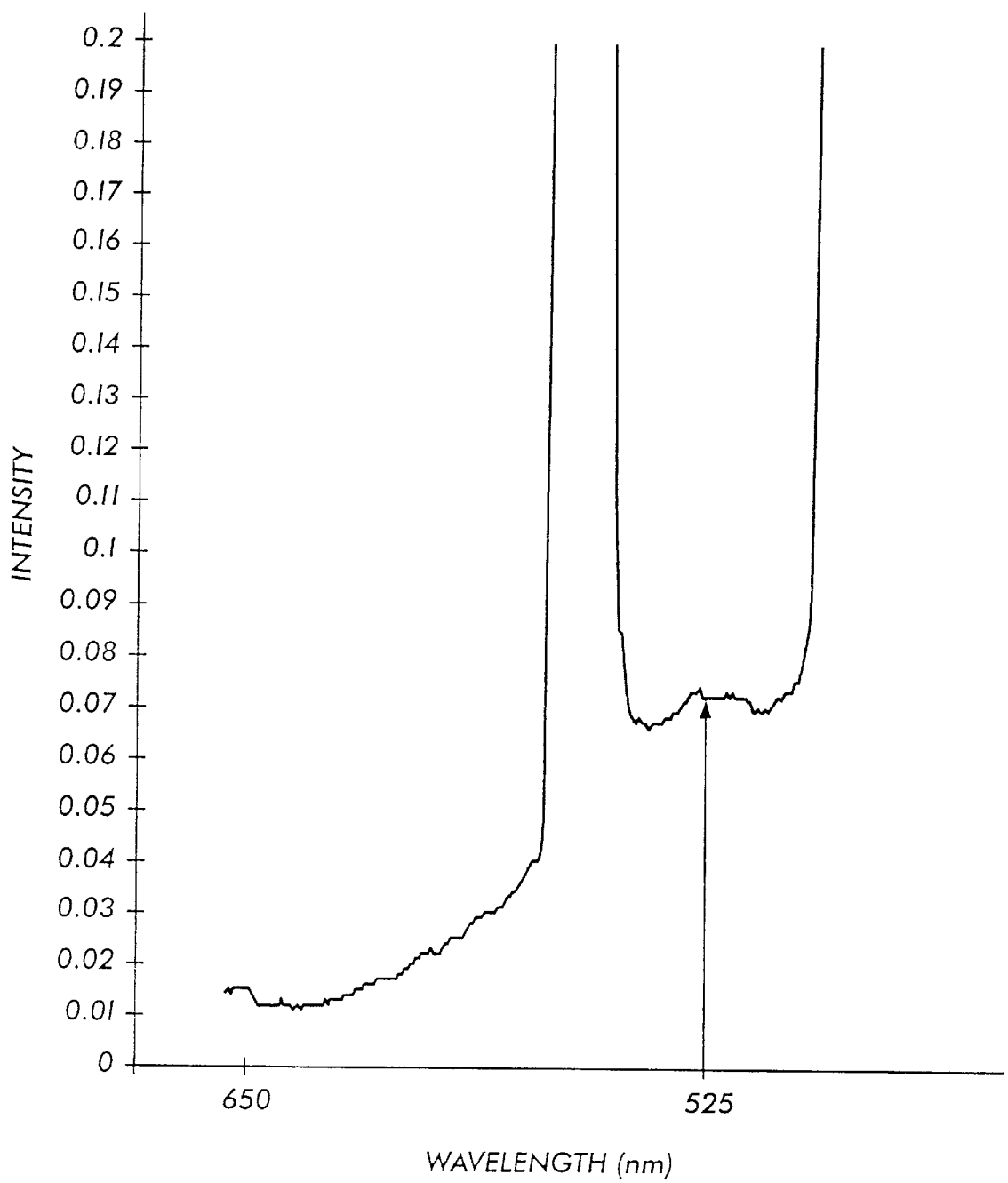

FIG. 17B gives the fluorescence spectrum of 5 pmol of DNA (SEQ ID NO:12) hybridized with 5 pmol of Probe No. 1. The positive signal at 525 nm is clearly shown in FIG. 17B.

Example 17c 5 pmol of DNA (SEQ ID NO:12) was added into 115 µl 0.5×TBE buffer. Then 5 pmol Probe No. 1 and 5 pmol Probe No. 2 were added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 17C:
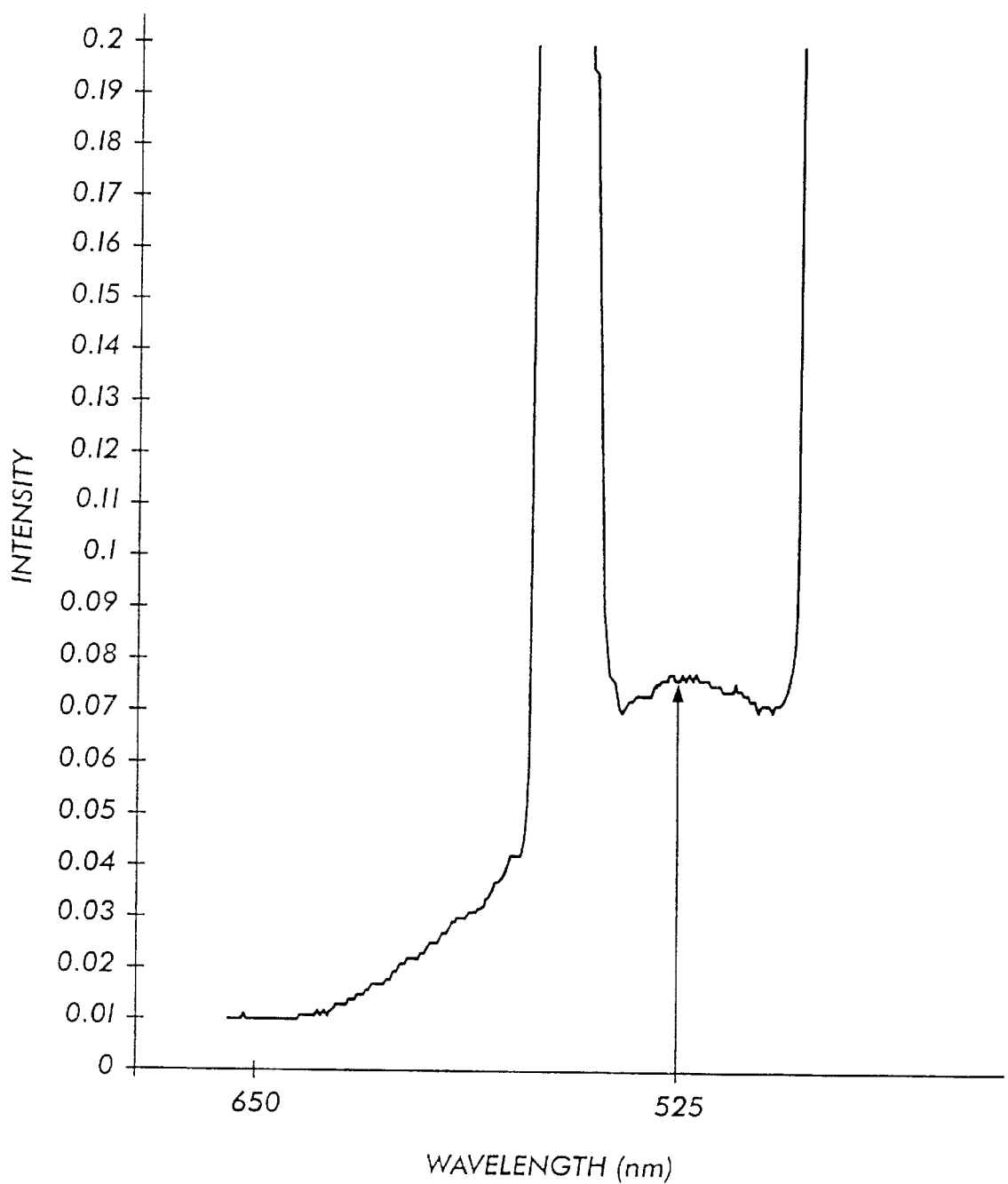

FIG. 17C shows the fluorescence spectrum of 5 pmol of DNA (SEQ ID NO:12) hybridized with 5 pmol of Probe No. 1 and 5 pmol of Probe No. 2. The fluorescent intensity at 525 nm is approximately equal to the intensity shown in FIG. 17B.

EXAMPLE 18

Two PNA probes having different dyes (fluorescein and rhodamine) hybridized with a one bp mismatched target and a perfectly matched target.

Example 18a 5 pmol of DNA (SEQ ID NO:12) was added into 115 µl 0.5×TBE buffer. Then 5 pmol of rhodamine labeled probe (Probe No. 3) was added into the solution. This probe was perfectly matched to the target sequence. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 18A:
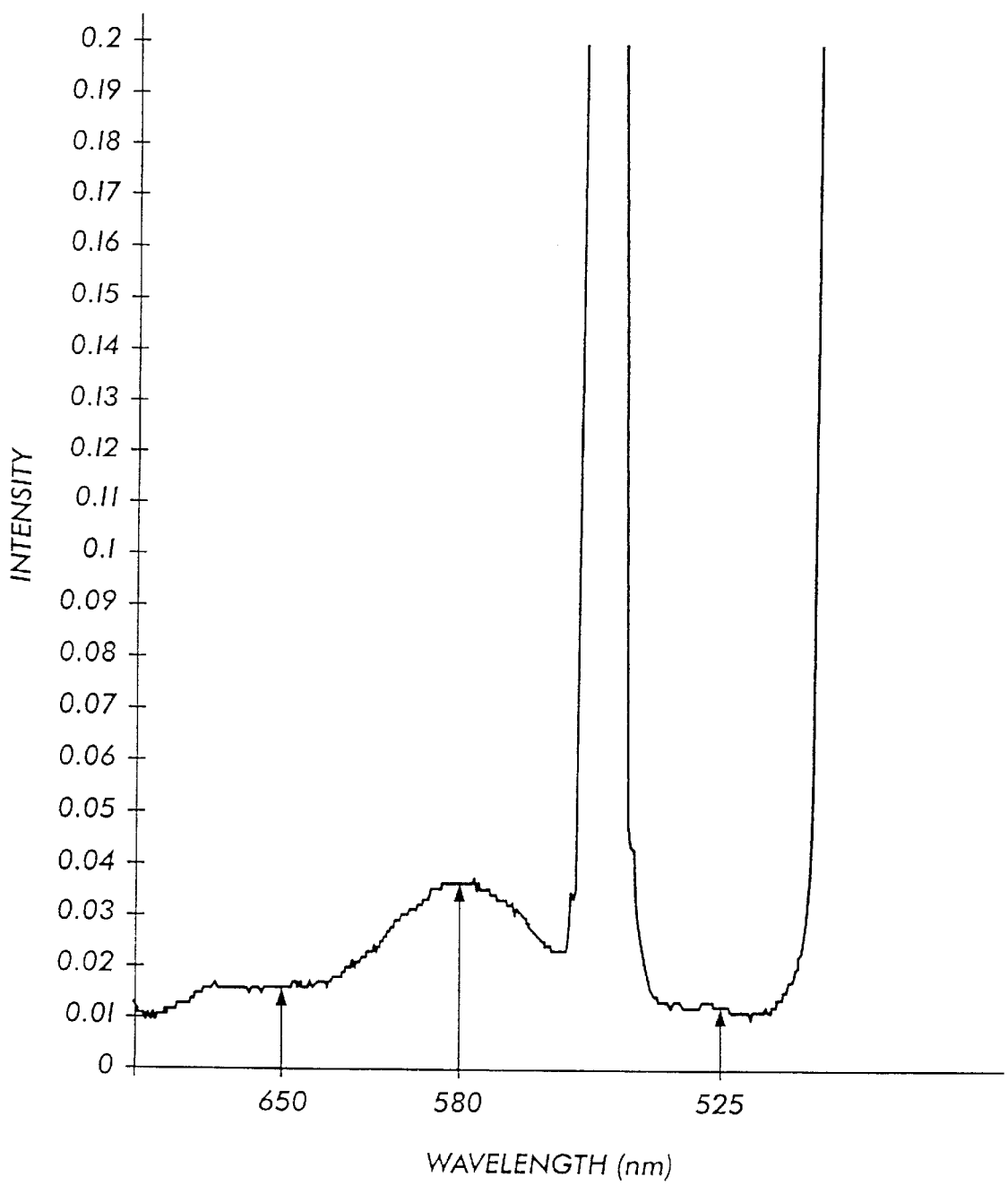

FIG. 18A shows the fluorescence spectrum of 5 pmol of DNA (SEQ ID NO:12) hybridized with 5 pmol of Probe No. 3. The positive signal at 580 nm is clearly shown in FIG. 18A.

Example 18b 5 pmol of DNA (SEQ ID NO:12) was added into 115 µl 0.5×TBE buffer. Then 5 pmol of Probe No. 3, which was perfectly matched to the target sequence, and 5 pmol of Probe No. 2, which has one base pair mismatched to the target sequence, were added to the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 18B:
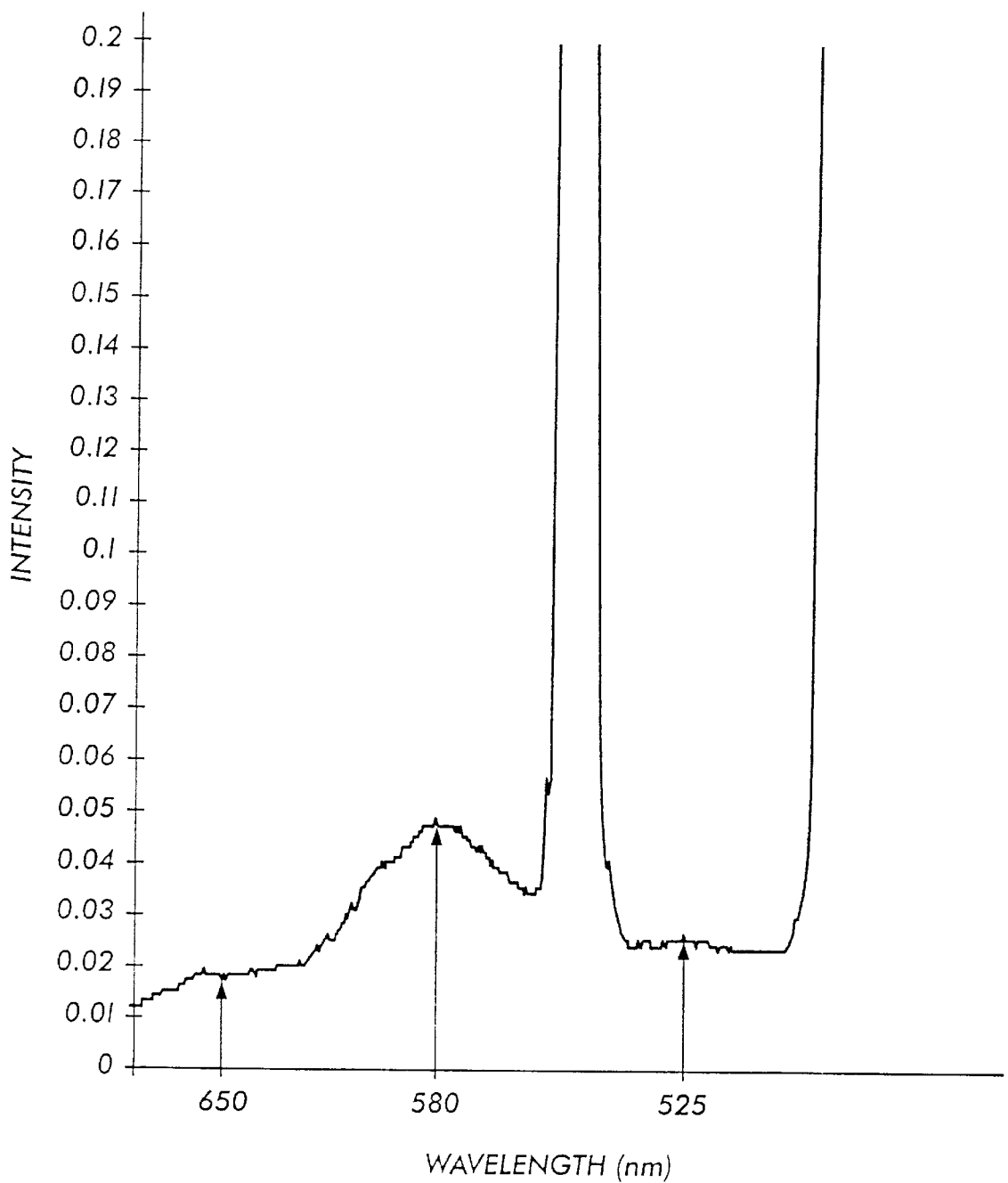

FIG. 18B shows the fluorescence spectrum of 5 pmol of DNA (SEQ ID NO:12) hybridized with 5 pmol of Probe No. 3 and 5 pmol of Probe No. 2. The fluorescent intensity at 525 nm is approximately equal to the intensity shown in FIG. 18A. The difference between the intensity at 580 nm and at 525 nm is approximately equal to that shown in FIG. 18A.

EXAMPLE 19

Three PNA probes having the same dye (fluorescein) hybridized with two one base pair mismatched target sequences and one perfectly matched target.

Example 19a

A 150 bp fragment of genomic DNA from p53 DNA gene QR (SEQ ID NO:13) was amplified by PCR and purified by using the QIAquick PCR Purification Kit. The mutated fragment was identical to the ME DNA (SEQ ID NO:11) fragment except for one base mutation at amino acid position 340 (bases 85–87) at which the DNA sequence CTC was changed to GTC and one base mismatch at amino acid position 344 (bases 100–102) at which the DNA sequence CTG was changed to CGG.

5 pmol of DNA (SEQ ID NO:13) was added into 115 µl 0.5×TBE buffer. Then 5 pmol of Probe No. 1, which has a one base pair mismatch to the target sequence at base pair position 101, was added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 19A:
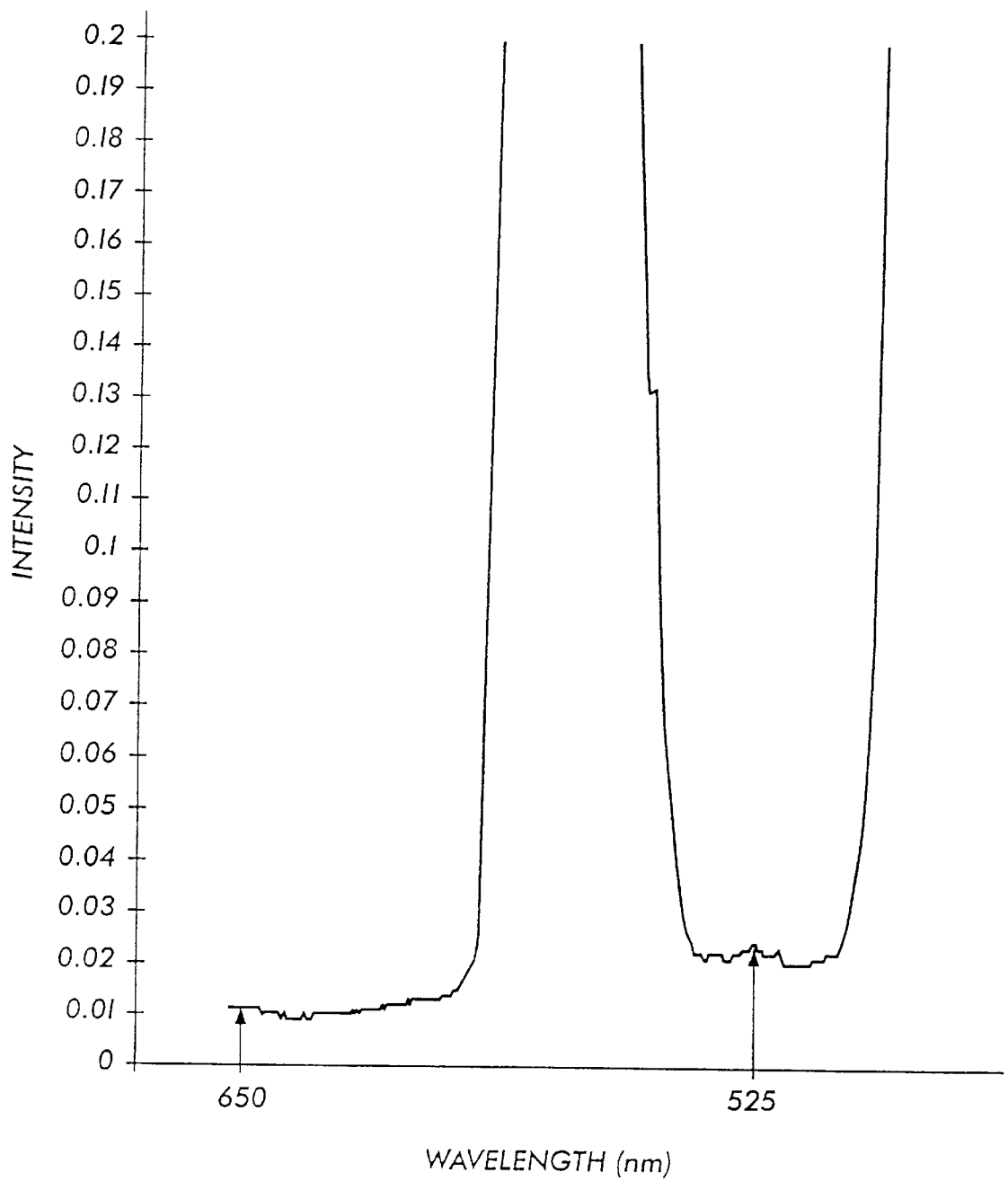

FIG. 19A shows the fluorescence spectrum of 5 pmol of DNA (SEQ ID NO: 13) hybridized with 5 pmol of Probe No. 1. The spectrum shows the fluorescent intensity at 525 nm at background level.

Example 19b 5 pmol of DNA (SEQ ID NO:13) was added into 115 μl 0.5×TBE buffer. Then Probe No. 2, which has a one base pair mismatch to the target sequence at base pair position 85, was added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 19B:
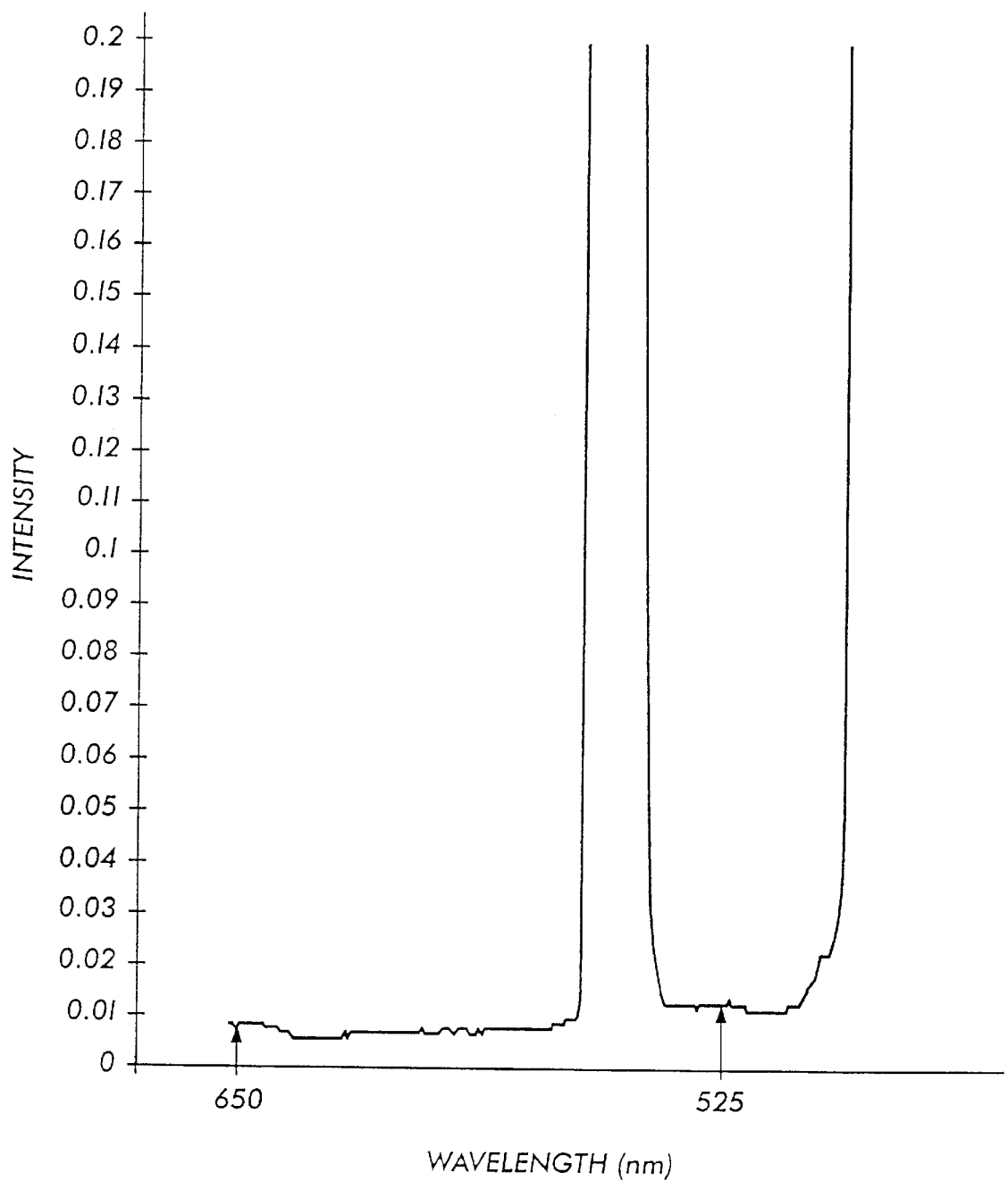

FIG. 19B shows the fluorescence spectrum of 5 pmol of DNA (SEQ ID NO: 13) hybridized with 5 pmol of Probe No. 2. The spectrum shows the fluorescent intensity at 525 nm at background level.

Example 19c 5 pmol of DNA (SEQ ID NO:13) was added into 115 μl 0.5×TBE buffer. A 12-mer fluorescein labeled PNA probe (Probe No. 4) synthesized by PerSeptive Biosystems, Inc., having the structure:

5'H-Fluo-O-CAT TCC GCT CTC Lys-CONH$_2$, was designed to be completely complementary to a 12 nucleotide segment of SEQ ID NO:13, starting at base pair position 95 and ending at base pair position 106. This probe was added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 19C:
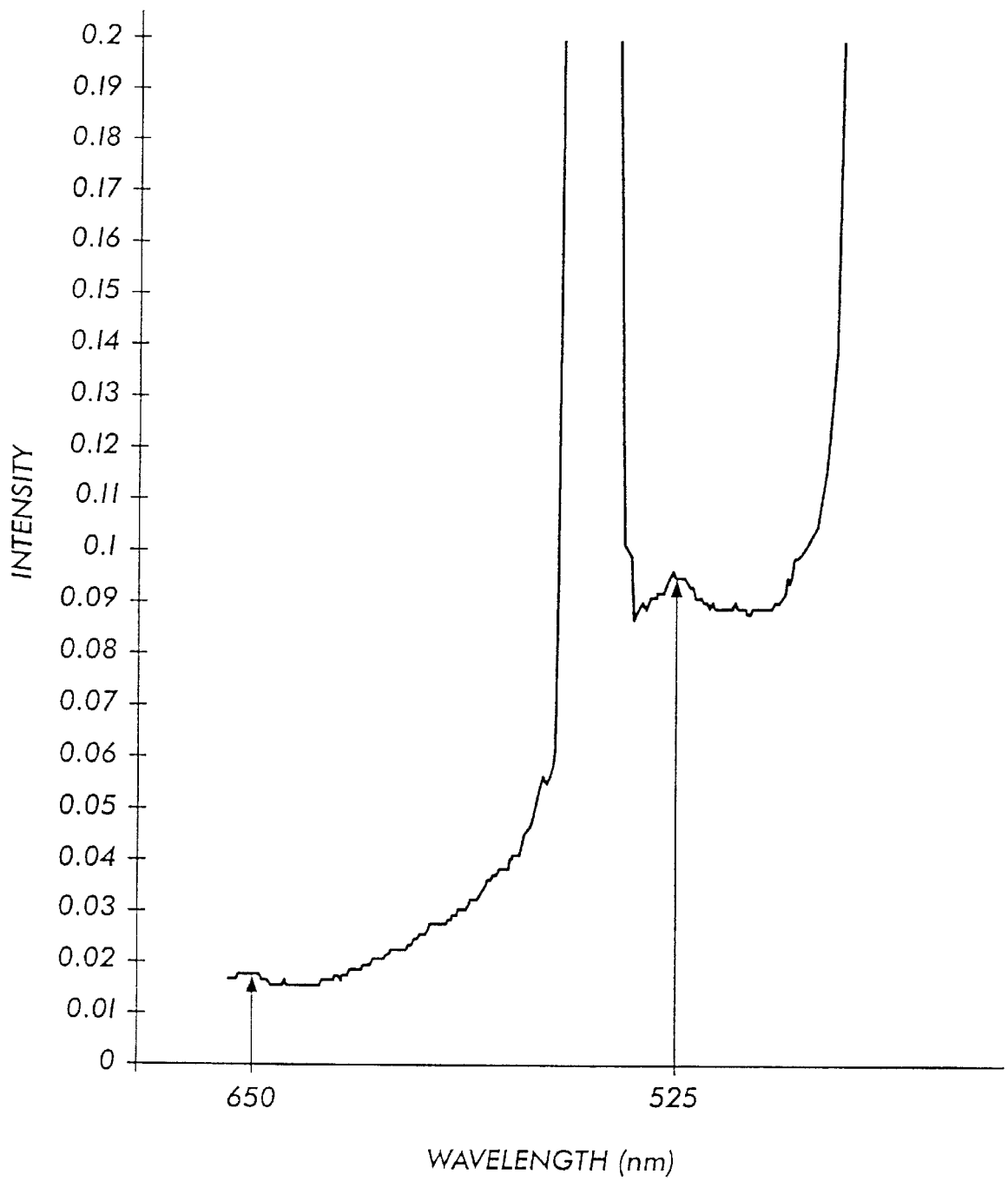

FIG. 19C shows the fluorescence spectrum of 5 pmol of DNA (SEQ ID NO:13) hybridized with 5 pmol of Probe No. 4. The positive signal at 525 nm is clearly shown in FIG. 19C.

Example 19d 5 pmol of DNA (SEQ ID NO:13) was added into 115 μl 0.5×TBE buffer. Then 5 pmol of Probe No. 1 and 5 pmol of Probe No. 2 were added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 19D:
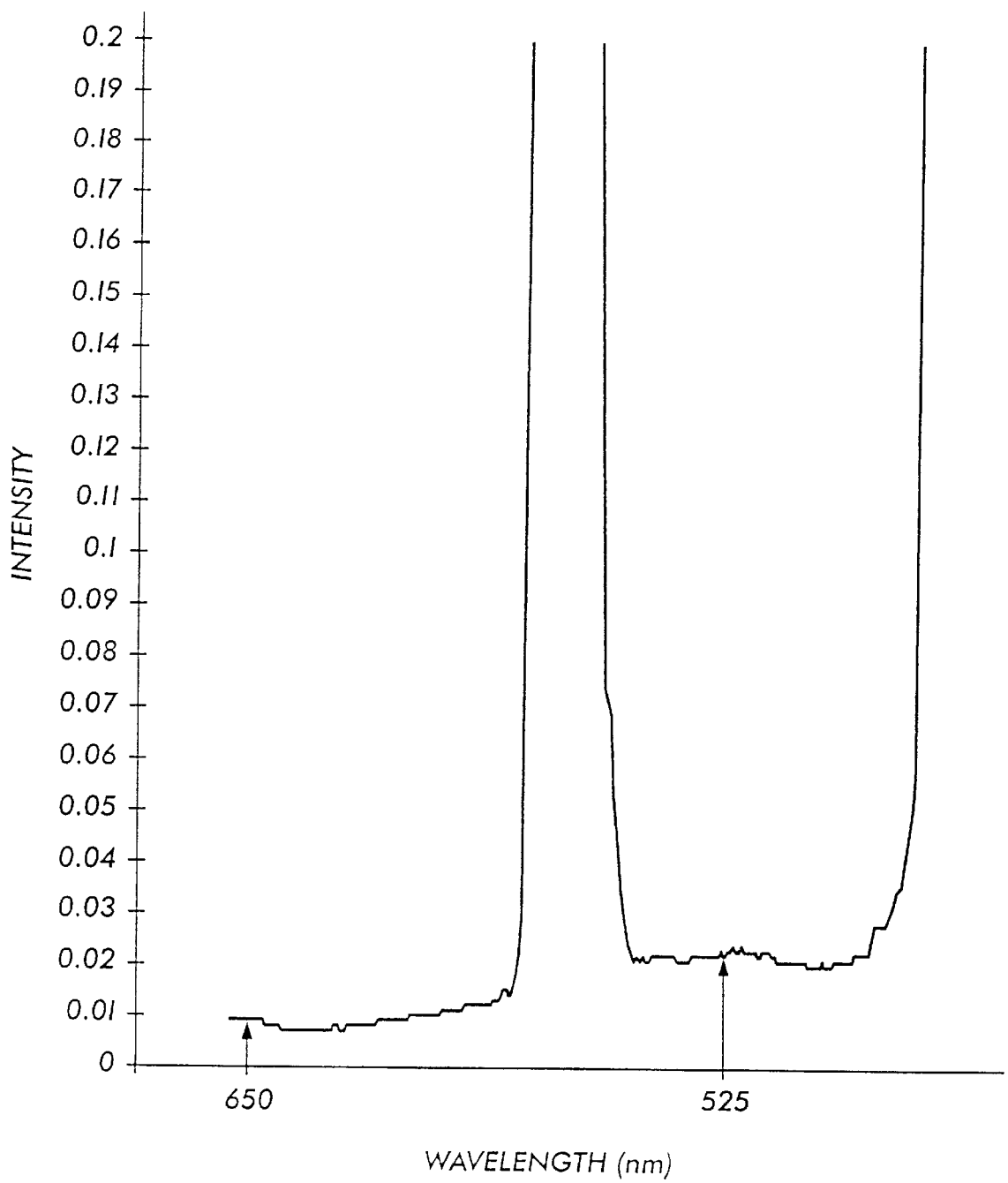

FIG. 19D gives the fluorescence spectrum of 5 pmol of DNA (SEQ ID NO:13) hybridized with 5 pmol of Probe No. 1 and 5 pmol of Probe No. 2. The spectrum shows the fluorescent intensity at 525 nm at background level.

Example 19e 5 pmol of DNA (SEQ ID NO:13) was added to 115 μl 0.5×TBE buffer. Then 5 pmol of Probe No. 1, 5 pmol of Probe No. 2 and 5 pmol of Probe No. 4 were added into the solution. The sample was heated at 95° C. for 10 minutes and hybridized at 25° C. for 30 minutes.

Before fluorescence measurement, the unbound probe was filtered from the solution by G50 spin column. The solution with the hybrids of PNA-DNA was placed into a cuvette and subjected to fluorescence measurement.

Figure 19E:
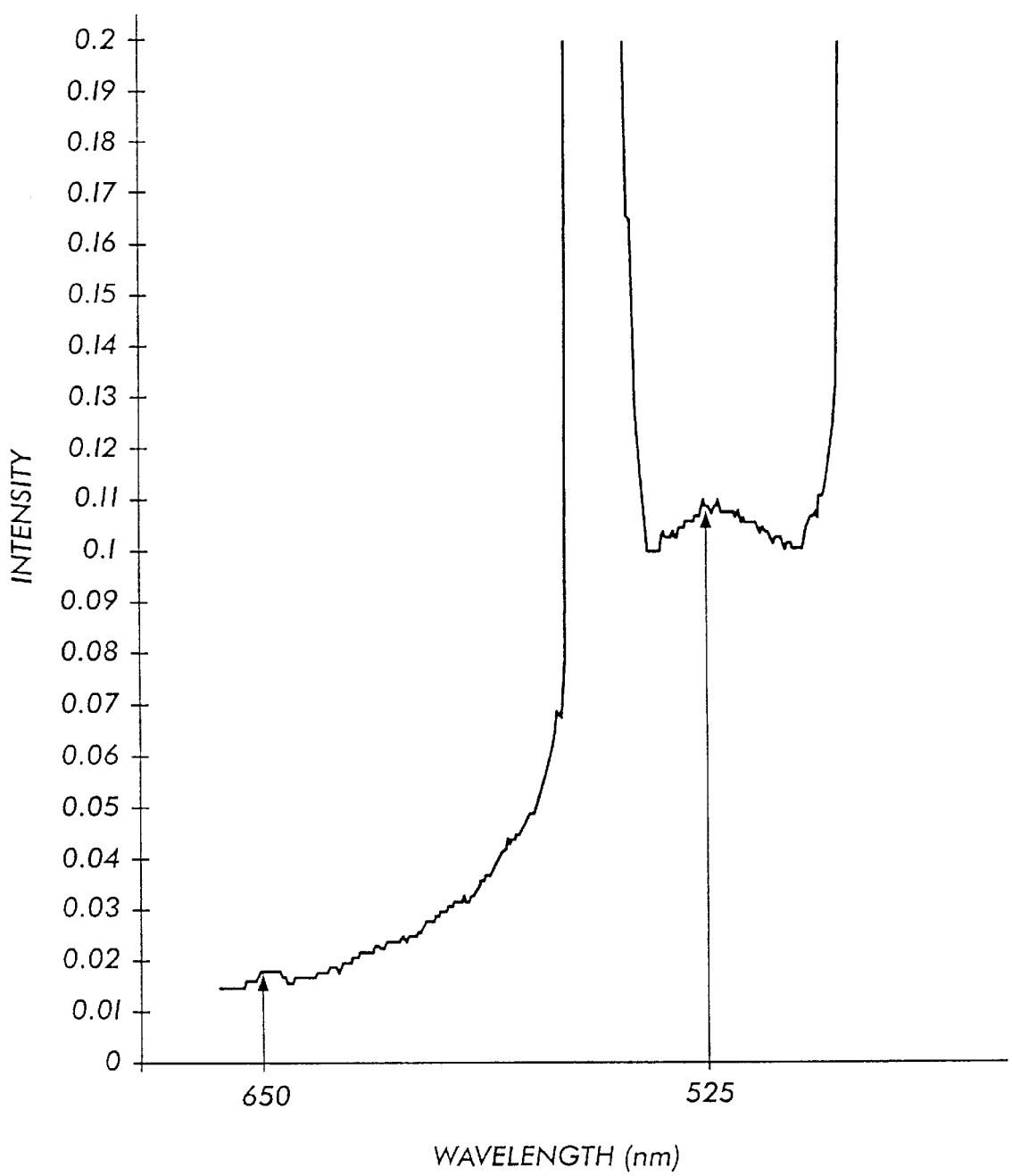

FIG. 19E gives the fluorescence spectrum of QR DNA (SEQ ID NO: 13) hybridized with PNA Probe Nos. 1, 2 and 4. The fluorescent intensity at 525 nm is approximately equal to the intensity shown in FIG. 19C.

While the invention has been described in detail and with reference to specific examples thereof, it will be apparent to one skilled in the art that various changes and modifications can be made therein without departing from the spirit and scope thereof.

---

What is claimed is:

1. A method for detecting at least one single stranded or double stranded nucleotide target sequence in a liquid medium, said method comprising:
adding to said liquid medium a PNA probe capable of forming a hybridization complex with said at least one target sequence, wherein said PNA probe comprises a fluorescent marker;
separating unhybridized PNA probe from said hybridization complex to form a test medium;
irradiating said test medium with a laser beam having a wavelength which excites said fluorescent marker and causes said fluorescent marker to emit fluorescent light;
measuring an intensity of said emitted fluorescent light; and
comparing said measured intensity with a reference intensity to detect whether said liquid medium contains said at least one target sequence,
wherein an inverse of said measured intensity is inversely proportional to a number of base mismatches between said at least one target sequence and said PNA probe, over a range inclusive of 0 base mismatches through at least 3 base mismatches, and wherein said method other than said separating step is entirely conducted without binding said PNA probe, said nucleotide sequence or said hybridization complex to a solid support or gel.

2. The method for detecting at least one nucleotide sequence according to claim 1, wherein said separation is accomplished by at least one of filtration, centrifugation, precipitation and free solution electrophoresis.

3. The method for detecting at least one nucleotide sequence according to claim 1, wherein said laser beam has a wavelength of about 450 to about 530 nm.

4. The method for detecting at least one nucleotide sequence according to claim 1, wherein said emitted fluorescent light is measured in a range of 400 to 1000 nm.

5. The method for detecting at least one nucleotide sequence according to claim 1, wherein at least two different PNA probes capable of forming a hybridization complex with said at least one target sequence are added to said liquid medium, a first of said at least two different PNA probes is complementary to a first segment of a first nucleotide target sequence, a second of said at least two different PNA probes is complementary to a second segment of a second nucleotide target sequence, and said first and second segments differ from each other.

6. The method for detecting at least one nucleotide sequence according to claim 5, wherein said first and second probes are completely complementary to said first and second segments, respectively.

7. The method for detecting at least one nucleotide sequence according to claim 6, wherein said first nucleotide sequence is complementary to said second nucleotide sequence.

8. The method for detecting at least one nucleotide sequence according to claim 7, wherein said first nucleotide sequence and said second nucleotide sequence are within opposing strands of double stranded DNA.

9. The method for detecting at least one nucleotide sequence according to claim 6, wherein said first nucleotide sequence and said second nucleotide sequence are in different genomes.

10. The method for detecting at least one nucleotide sequence according to claim 9, wherein said first probe has a first marker which has a first fluorescent emission intensity at a first wavelength, said second probe has a second marker which has a second fluorescent emission intensity at a second wavelength, said first and second wavelengths are different, said first nucleotide sequence is detected by monitoring fluorescent emission intensity at said first wavelength and said second nucleotide sequence is detected by monitoring fluorescent emission intensity at said second wavelength.

11. The method for detecting at least one nucleotide sequence according to claim 6, wherein said first probe has a first marker which has a first fluorescent emission intensity at a first wavelength, said second probe has a second marker which has a second fluorescent emission intensity at a second wavelength, said first and second wavelengths are different, said first nucleotide sequence is detected by monitoring fluorescent emission intensity at said first wavelength and said second nucleotide sequence is detected by monitoring fluorescent emission intensity at said second wavelength.

12. The method for detecting at least one nucleotide sequence according to claim 11, wherein said first nucleotide sequence is a positive control expected to be present in said liquid medium being analyzed, said first intensity is said reference intensity, said second intensity is said measured intensity, and said second nucleotide sequence is detected by comparing said first intensity and said second intensity.

13. The method for detecting at least one nucleotide sequence according to claim 12, wherein the second nucleotide sequence is found only in a mutant genome and the first nucleotide sequence is found in said mutant genome and in a corresponding wild type genome.

14. The method for detecting at least one nucleotide sequence according to claim 12, wherein the first and second markers are selected from the group consisting of fluorescein and rhodamine.

15. The method for detecting at least one nucleotide sequence according to claim 12, wherein a third PNA probe having a third marker which has a third fluorescent emission intensity at a third wavelength differing from the first and second wavelengths is added to said liquid medium as a negative control which is not expected to hybridize with any nucleotide sequence, and said second nucleotide sequence is detected by comparing the first, second and third intensities.

16. The method for detecting at least one nucleotide sequence according to claim 1, wherein at least two different PNA probes capable of forming a hybridization complex with said at least one target sequence are added to said liquid medium, a first of said at least two different PNA probes is complementary to a first segment of said at least one target sequence, a second of said at least two different PNA probes is complementary to a second segment of said at least one target sequence, and said first and second segments differ from each other.

17. The method for detecting at least one nucleotide sequence according to claim 16, wherein said first probe has a first marker which has a first fluorescent emission intensity at a first wavelength, said second probe has a second marker which has a second fluorescent emission intensity at a second wavelength, said first and second wavelengths are different, said first segment is detected by monitoring fluorescent emission intensity at said first wavelength and said second segment is detected by monitoring fluorescent emission intensity at said second wavelength.

18. The method for detecting at least one nucleotide sequence according to claim 17, wherein said first segment is a positive control expected to be present in said liquid medium being analyzed, said first intensity is said reference intensity, said second intensity is said measured intensity, and said second segment is detected by comparing said first intensity and said second intensity.

19. The method for detecting at least one nucleotide sequence according to claim 18, wherein a third PNA probe having a third marker which has a third fluorescent emission intensity at a third wavelength differing from the first and second wavelengths is added to said liquid medium as a negative control which is not expected to hybridize with any nucleotide segment, and said second segment is detected by comparing the first, second and third intensities.

20. The method for detecting at least one nucleotide sequence according to claim 1, wherein said hybridization complex consists essentially of one PNA sequence, one fluorophore and said nucleotide sequence.

21. The method for detecting at least one nucleotide sequence according to claim 1, wherein all probes employed in said method consist of the same sequence and marker, said marker being the only marker detected in said method.

22. The method for detecting at least one nucleotide sequence according to claim 1, wherein said emitted fluorescent light has a wavelength longer than said laser beam wavelength.

23. The method for detecting at least one nucleotide sequence according to claim 1, wherein said at least one nucleotide sequence is double stranded DNA.

24. A method for detecting a single stranded or double stranded nucleotide sequence in a first liquid medium, comprising:
providing said first liquid medium comprising sample nucleotide sequences;
adding to said first liquid medium a PNA probe capable of forming a hybridization complex with said nucleotide sequence, wherein said PNA probe comprises a fluorescent marker;
separating unhybridized PNA probe from said hybridization complex to form a first test medium;
irradiating said first test medium with a laser beam having a wavelength which excites said fluorescent marker and causes said fluorescent marker to emit fluorescent light;
detecting a first intensity of said fluorescent light in said first test medium; and
determining whether said first intensity is equal to a second intensity of a second liquid medium containing said nucleotide sequence hybridized with said PNA probe, to detect whether said nucleotide sequence is in said first liquid medium,
wherein (i) said method other than said separating step is entirely conducted without binding said PNA probe, said nucleotide sequence or said hybridization complex to a solid support or gel, (ii) an inverse of said first intensity is proportional to a number of base mismatches between said nucleotide sequence and said PNA probe, over a range inclusive of 0 base mismatches through at least 3 base mismatches, and (iii) said hybridization complex consists essentially of one PNA sequence, one fluorophore and said nucleotide sequence.

25. The method for detecting a nucleotide sequence according to claim 24, wherein said laser beam is produced by an argon ion laser which irradiates said marker with light having a wavelength of about 450 to about 530 nm.

26. The method for detecting a nucleotide sequence according to claim 24, wherein said fluorescent light is detected in a range of 400 to 1000 nm.

27. The method for detecting a nucleotide sequence according to claim 24, wherein (i) said nucleotide sequence is a mutant type DNA to be distinguished from a wild type DNA differing from said mutant type DNA, (ii) said PNA probe is completely complementary with a segment of said mutant type DNA and is not completely complementary with a segment of said wild type DNA, and (iii) said mutant type DNA is detected if said first intensity equals said second intensity.

28. The method for detecting a nucleotide sequence according to claim 24, wherein (i) said nucleotide sequence is a wild type DNA to be distinguished from a mutant type DNA differing from said wild type DNA, (ii) said PNA probe is completely complementary with a segment of said wild type DNA and is not completely complementary with a segment of said mutant type DNA, and (iii) said wild type DNA is detected if said first intensity equals said second intensity.

29. The method for detecting a nucleotide sequence according to claim 24, wherein said nucleotide sequence is denatured in said liquid medium prior to said detecting step, at a temperature of about 85° C. to about 100° C. for about 30 seconds to about 5 hours.

30. The method for detecting a nucleotide sequence according to claim 29, wherein said hybridization complex formation is conducted at a temperature of about 4° C. to about 75° C. for about 2 minutes to about 24 hours.

31. The method for detecting a nucleotide sequence according to claim 30, wherein said denaturing step is conducted for no more than 60 minutes, after which said temperature is passively cooled to room temperature without quenching.

32. The method for detecting a nucleotide sequence according to claim 24, wherein said PNA probe is added to said first liquid medium in a concentration 1 to 20 times a suspected concentration of said nucleotide sequence.

33. The method for detecting a nucleotide sequence according to claim 24, wherein a total volume of said first test medium in said detecting step is no more than about 5 milliliters.

34. The method for detecting a nucleotide sequence according to claim 33, wherein said total volume is no more than about 10 microliters.

35. The method for detecting a nucleotide sequence according to claim 24, wherein said nucleotide sequence is double stranded DNA.

36. The method for detecting a nucleotide sequence according to claim 29, wherein said PNA probe is added to said first liquid medium prior to completion of said denaturing step.

37. The method of claim 24, wherein all probes employed in said method consist of the same sequence and marker, said marker being the only marker detected in said method.

38. The method of claim 24, wherein said detected fluorescent light consists essentially of said fluorescent light emitted by said marker.

39. The method of claim 24, wherein said PNA probe is completely complementary to a segment of said nucleotide sequence.

40. The method of claim 24, wherein said PNA probe is a one-base mismatch of a segment of said nucleotide sequence.

41. The method of claim 24, wherein said PNA probe is a two-base mismatch of a segment of said nucleotide sequence.

42. The method of claim 24, wherein said PNA probe is a three-base mismatch of a segment of said nucleotide sequence.

43. The method of claim 24, wherein (i) said sample nucleotide sequences are identical to said nucleotide sequence or are analogs differing from said nucleotide sequence by at least one base, (ii) said PNA probe is completely complementary with a segment of said nucleotide sequence and is not complementary with a segment of said analogs, (iii) said nucleotide sequence is detected if said first intensity equals said second intensity, and (iv) said analogs are detected if said first intensity does not equal said second intensity.

44. The method of claim 43, wherein said analogs differ from said nucleotide sequence by one base.

45. The method of claim 43, wherein said analogs differ from said nucleotide sequence by two bases.

46. The method of claim 43, wherein said analogs differ from said nucleotide sequence by three bases.

47. The method of claim 43, wherein all probes employed in said method consist of the same sequence and marker, said marker being the only marker detected in said methods.

48. The method of claim 47, wherein said detected fluorescent light consists essentially of said fluorescent light emitted by said marker.

49. The method of claim 48, wherein said analogs differ from said nucleotide sequence by one base.

50. The method of claim 24, wherein (i) said sample nucleotide sequences are identical to said nucleotide sequence or are analogs differing from said nucleotide sequence by at least one base, (ii) said PNA probe is completely complementary with a segment of said analogs and is not completely complementary with a segment of said nucleotide sequence, (iii) said nucleotide sequence is detected if said first intensity equals said second intensity, and (iv) said analogs are detected if said first intensity does not equal said second intensity.

51. The method of claim 50, wherein said analogs differ from said nucleotide sequence by one base.

52. The method of claim 50, wherein said analogs differ from said nucleotide sequence by two bases.

53. The method of claim 50, wherein said analogs differ from said nucleotide sequence by three bases.

54. The method of claim 50, wherein all probes employed in said method consist of the same sequence and marker, said marker being the only marker detected in said method.

55. The method of claim 54, wherein said detected fluorescent light consists essentially of said fluorescent light emitted by said marker.

56. The method of claim 55, wherein said analogs differ from said nucleotide sequence by one base.

57. A method for detecting a single stranded or double stranded nucleotide sequence in a first liquid medium, comprising:
providing said first liquid medium comprising sample nucleotide sequences;
adding to said first liquid medium a PNA probe capable of forming a hybridization complex with said nucleotide sequence, wherein said PNA probe comprises a fluorescent marker;
separating unhybridized PNA probe from said hybridization complex to form a first test medium;
irradiating said first test medium with a laser beam having a wavelength which excites said fluorescent marker and causes said fluorescent marker to emit fluorescent light;
directly detecting a first intensity of said emitted fluorescent light in said first test medium; and
comparing said first intensity with a reference intensity produced by probing a positive control sequence and a baseline intensity produced by probing a negative control sequence,
wherein (i) said nucleotide sequence is detected when said first intensity equals said reference intensity, (ii) said nucleotide sequence is not detected when said first intensity equals said baseline intensity, (iii) a homologous sequence differing from said nucleotide sequence by at least one base is detected when said first intensity is between said baseline intensity and said reference intensity, (iv) said method other than said separating step is entirely conducted without binding said PNA probe, said nucleotide sequence or said hybridization complex to a solid support or gel, and (v) an inverse of said first intensity is proportional to a number of base mismatches between said nucleotide sequence and said PNA probe, over a range inclusive of 0 base mismatches through at least 3 base mismatches.

58. The method of claim 57, wherein said homologous sequence differs from said nucleotide sequence by one base.

59. The method of claim 57, wherein said hybridization complex consists essentially of one PNA sequence, one fluorophore and said nucleotide sequence.

60. The method of claim 57, wherein all probes employed in said method consist of the same sequence and marker, said marker being the only marker detected in said method.

61. The method of claim 57, wherein said detected fluorescent light consists essentially of said fluorescent light emitted by said marker.

62. The method of claim 57, wherein said detected fluorescent light has a wavelength longer than said laser beam wavelength.

63. The method of claim 24, wherein said detected fluorescent light has a wavelength longer than said laser beam wavelength.

64. A method for detecting a single stranded or double stranded nucleotide sequence in a first liquid medium, comprising:
providing said first liquid medium comprising sample nucleotide sequences;
adding to said first liquid medium a PNA probe capable of forming a hybridization complex with said nucleotide sequence, wherein said PNA probe comprises a fluorescent marker;
separating unhybridized PNA probe from said hybridization complex to form a first test medium;
irradiating said first test medium with a laser beam having a wavelength which excites said fluorescent marker and causes said fluorescent marker to emit fluorescent light;
detecting a first intensity of said fluorescent light in said first test medium; and
determining whether said first intensity is equal to a second intensity of a second liquid medium containing said nucleotide sequence hybridized with said PNA probe, to detect whether said nucleotide sequence is in said first liquid medium, wherein (i) said method other than said separating step is entirely conducted without binding said PNA probe, said nucleotide sequence or said hybridization complex to a solid support or gel, (ii) an inverse of said first intensity is proportional to a number of base mismatches between said nucleotide sequence and said PNA probe, up to at least 3 base mismatches, and (iii) said hybridization complex consists essentially of one PNA sequence, one fluorophore and said nucleotide sequence.

65. The method of claim 64, wherein said inverse of said first intensity is proportional over a range of at least 1 to 3 base mismatches.

66. A method for detecting a single stranded or double stranded nucleotide sequence in a liquid medium, comprising:

providing said liquid medium comprising first nucleotide sequences which are identical to said nucleotide sequence or second nucleotide sequences differing from said nucleotide sequence by at least one base;

adding to said liquid medium PNA probes completely complementary to a segment of said nucleotide sequence and not completely complementary to a segment of said second nucleotide sequences, wherein each of said PNA probes comprises a fluorescent marker;

hybridizing said PNA probes with said first or second nucleotide sequences;

irradiating said liquid medium to cause said fluorescent marker to emit fluorescent light having a wavelength of 400 to 1000 nm; and detecting an intensity of said fluorescent light, wherein an electric field is applied to said liquid medium prior to or concurrently with said detecting step, and a change in said intensity of said fluorescent light as a function of said electric field is detected as an indication of whether said PNA probes are hybridized to said first nucleotide sequences or to said second nucleotide sequences.

67. The method of claim 66, wherein said first and second nucleotide sequences differ by one base.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 150 bases
      (B) TYPE: nucleotide
      (C) STRANDEDNESS: double-stranded
      (D) TOPOLOGY: linear (ii) MOLECULE TYPE: genomic DNA (xi) SEQUENCE DESCRIPTION: SEQ ID NO:1:

AACACCAGCT CCTCTCCCCA GCCAAAGAAG AAACCACTGG ATGGAGAATA TTTCACCCTT    60

CAGATCCGTG GGCGTGAGCG CTTCGAGATG TTCCGAGAGC TGAATGAGGC CTTGGAACTC    120

AAGGATGCCC AGGCTGGGAA GGAGCCAGGG    150

(2) INFORMATION FOR SEQ ID NO:2:

(i) SEQUENCE CHARACTERISTICS:
            (A) LENGTH: 150 bases
            (B) TYPE: nucleotide
            (C) STRANDEDNESS: double-stranded
            (D) TOPOLOGY: linear (xi) SEQUENCE DESCRIPTION: SEQ ID NO:2:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGC AGAATGAGGC CTTGGAACTC     120

AAGGATGCCC AGGCTGGGAA GGAGCCAGGG                                      150

(2) INFORMATION FOR SEQ ID NO:3:

(i) SEQUENCE CHARACTERISTICS:
            (A) LENGTH: 150 bases
            (B) TYPE: nucleotide
            (C) STRANDEDNESS: double-stranded
            (D) TOPOLOGY: linear (xi) SEQUENCE DESCRIPTION: SEQ ID NO:3:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGC GGAATGAGGC CTTGGAACTC     120

AAGGATGCCC AGGCTGGGAA GGAGCCAGGG                                      150

(2) INFORMATION FOR SEQ ID NO:4:

(i) SEQUENCE CHARACTERISTICS:
            (A) LENGTH: 150 bases
            (B) TYPE: nucleotide
            (C) STRANDEDNESS: double-stranded
            (D) TOPOLOGY: linear (xi) SEQUENCE DESCRIPTION: SEQ ID NO:4:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGA AGAATGAGGC CTTGGAACTC     120

AAGGATGCCC AGGCTGGGAA GGAGCCAGGG                                      150

(2) INFORMATION FOR SEQ ID NO:5:

(i) SEQUENCE CHARACTERISTICS:
            (A) LENGTH: 150 bases
            (B) TYPE: nucleotide
            (C) STRANDEDNESS: double-stranded
            (D) TOPOLOGY: linear (xi) SEQUENCE DESCRIPTION: SEQ ID NO:5:

AACACCAGCT CCTCTCCCCA GCCAAAGAAG AAACCACTGG ATGGAGAATA TTTCACCCTT      60

CAGATCCGTG GGCGTGAGCG CTTCGAGATG TTCCGAGAGG CGAATGAGGC CTTGGAACTC     120

AAGGATGCCC AGGCTGGGAA GGAGCCAGGG                                      150

(2) INFORMATION FOR SEQ ID NO:6:

(i) SEQUENCE CHARACTERISTICS:
            (A) LENGTH: 150 bases
            (B) TYPE: nucleotide
            (C) STRANDEDNESS: double-stranded
            (D) TOPOLOGY: linear (xi) SEQUENCE DESCRIPTION: SEQ ID NO:6:

AACACCAGCT CCTCTCCCCA GCCAAAGAAG AAACCACTGG ATGGAGAATA TTTCACCCTT      60

```
CAGATCCGTG GGCGTGAGCG CTTCGAGATG TTCCGAGAGT ACAATGAGGC CTTGGAACTC    120

AAGGATGCCC AGGCTGGGAA GGAGCCAGGG                                    150

(2) INFORMATION FOR SEQ ID NO:7:

(i) SEQUENCE CHARACTERISTICS:
        (A) LENGTH: 375 bases
        (B) TYPE: nucleotide
        (C) STRANDEDNESS: double-stranded
        (D) TOPOLOGY: linear (xi) SEQUENCE DESCRIPTION: SEQ ID NO:7:

TTAATACGAC TCACTATAGG GGAATTGTGA GCGGATAACA ATTCCCCTCT AGAAATAATT     60

TTGTTTAACT TTAAGAAGGA GATATACCAT GGGCCATCAT CATCATCATC ATCATCATCA   120

TCACAGCAGC GGCCATATCG ACGACGACGA CAAGCAAACA CCAGCTCCTC TCCCCAGCCA   180

AAGAAGAAAC CACTGGATGG AGAATATTTC ACCCTTCAGA TCCGTGGGCG TGAGCGCTTC   240

GAGATGTTCC GAGAGCTGAA TGAGGCCTTG GAACTCAAGG ATGCCCAGGC TGGGAAGGAG   300

CCAGGGGATC CGGCTGCTAA CAAAGCCCGA AAGGAAGCTG AGTTGGCTGC TGCCACCGCT   360

GAGCAATAAC TAGCA                                                   375

(2) INFORMATION FOR SEQ ID NO:8:

(i) SEQUENCE CHARACTERISTICS:
        (A) LENGTH: 375 bases
        (B) TYPE: nucleotide
        (C) STRANDEDNESS: double-stranded
        (D) TOPOLOGY: linear (xi) SEQUENCE DESCRIPTION: SEQ ID NO:8:

TTAATACGAC TCACTATAGG GGAATTGTGA GCGGATAACA ATTCCCCTCT AGAAATAATT     60

TTGTTTAACT TTAAGAAGGA GATATACCAT GGGCCATCAT CATCATCATC ATCATCATCA   120

TCACAGCAGC GGCCATATCG ACGACGACGA CAAGCAAACA CCAGCTCCTC TCCCCAGCCA   180

AAGAAGAAAC CACTGGATGG AGAATATTTC ACCCTTCAGA TCCGTGGGCG TGAGCGCTTC   240

GAGATGTTCC GAGAGCAGAA TGAGGCCTTG GAACTCAAGG ATGCCCAGGC TGGGAAGGAG   300

CCAGGGGATC CGGCTGCTAA CAAAGCCCGA AAGGAAGCTG AGTTGGCTGC TGCCACCGCT   360

GAGCAATAAC TAGCA                                                   375

(2) INFORMATION FOR SEQ ID NO:9:

(i) SEQUENCE CHARACTERISTICS:
        (A) LENGTH: 375 bases
        (B) TYPE: nucleotide
        (C) STRANDEDNESS: double-stranded
        (D) TOPOLOGY: linear (xi) SEQUENCE DESCRIPTION: SEQ ID NO:9:

TTAATACGAC TCACTATAGG GGAATTGTGA GCGGATAACA ATTCCCCTCT AGAAATAATT     60

TTGTTTAACT TTAAGAAGGA GATATACCAT GGGCCATCAT CATCATCATC ATCATCATCA   120

TCACAGCAGC GGCCATATCG ACGACGACGA CAAGCAAACA CCAGCTCCTC TCCCCAGCCA   180

AAGAAGAAAC CACTGGATGG AGAATATTTC ACCCTTCAGA TCCGTGGGCG TGAGCGCTTC   240

GAGATGTTCC GAGAGCGGAA TGAGGCCTTG GAACTCAAGG ATGCCCAGGC TGGGAAGGAG   300

CCAGGGGATC CGGCTGCTAA CAAAGCCCGA AAGGAAGCTG AGTTGGCTGC TGCCACCGCT   360

GAGCAATAAC TAGCA                                                   375
```

(2) INFORMATION FOR SEQ ID NO:10:

(i) SEQUENCE CHARACTERISTICS:
        (A) LENGTH: 633 bases
        (B) TYPE: nucleotide
        (C) STRANDEDNESS: double-stranded
        (D) TOPOLOGY: linear (xi) SEQUENCE DESCRIPTION: SEQ ID NO:10:

```
CCGGCGGCCC CTGCACCAGC CCCCTCCTGG CCCCTGTCAT CTTCTGTCCC TTCCCAGAAA  60
ACCTACCAGG GCAGCTACGG TTTCCGTCTG GGCTTCTTGC ATTCTGGGAC AGCCAAGTCT 120
GTGACTTGCA CGTACTCCCC TGCCCTCAAC AAGATGTTTT GCCAACTGGC CAAGACCTGC 180
CCTGTGCAGC TGTGGGTTGA TTCCACACCC CCGCCCGGCA CCCGCGTCCG CGCCATGGCC 240
ATCTACAAGC AGTCACAGCA CATGACGGAG GTTGTGAGGC GCTGCCCCCA CCATGAGCGC 300
TGCTCAGATA GCGATGGTCT GGCCCCTCCT CAGCATCTTA TCCGAGTGGA AGGAAATTTG 360
CGTGTGGAGT ATTTGGATGA CAGAAACACT TTTCGACATA GTGTGGTGGT GCCCTATGAG 420
CCGCCTGAGG TTGGCTCTGA CTGTACCACC ATCCACTACA ACTACATGTG TAACAGTTCC 480
TGCATGGGCG GCATGAACCG GAGGCCCATC CTCACCATCA TCACACTGGA AGACTCCAGT 540
GGTAATCTAC TGGGACGGAA CAGCTTTGAG GTGCGTGTTT GTGCCTGTCC TGGGAGAGAC 600
CGGCGCACAG AGGAAGAGAA TCTCCGCAAG AAA                              633
```

(2) INFORMATION FOR SEQ ID NO:11:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (xi) SEQUENCE DESCRIPTION: SEQ ID NO:11:

```
AACACCAGCT CCTCTCCCCA GCCAAAGAAG AAACCACTGG ATGGAGAATA TTTCACCCTT  60
CAGATCCGTG GGCGTGAGCG CTTCGAGGAG TTCCGAGAGC TGAATGAGGC CTTGGAACTC 120
AAGGATGCCC AGGCTGGGAA GGAGCCAGGG                                  150
```

(2) INFORMATION FOR SEQ ID NO:12:

(i) SEQUENCE CHARACTERISTICS:
        (A) LENGTH: 150 bases
        (B) TYPE: nucleotide
        (C) STRANDEDNESS: double-stranded
        (D) TOPOLOGY: linear (xi) SEQUENCE DESCRIPTION: SEQ ID NO:12:

```
AACACCAGCT CCTCTCCCCA GCCAAAGAAG AAACCACTGG ATGGAGAATA TTTCACCCTT  60
CAGATCCGTG GGCGTGAGCG CTTCGAGCAG TTCCGAGAGC TGAATGAGGC CTTGGAACTC 120
AAGGATGCCC AGGCTGGGAA GGAGCCAGGG                                  150
```

(2) INFORMATION FOR SEQ ID NO:13:
    (i) SEQUENCE CHARACTERISTICS:
        (A) LENGTH: 150 bases
        (B) TYPE: nucleotide
        (C) STRANDEDNESS: double-stranded
        (D) TOPOLOGY: linear (xi) SEQUENCE DESCRIPTION: SEQ ID NO:13:

```
AACACCAGCT CCTCTCCCCA GCCAAAGAAG AAACCACTGG ATGGAGAATA TTTCACCCTT  60
```

-continued

```
CAGATCCGTG GGCGTGAGCG CTTCCAGGAG TTCCGAGAGC GGAATGAGGC CTTGGAACTC        120

AAGGATGCCC AGGCTGGGAA GGAGCCAGGG                                         150
```